(12) United States Patent
Kocár et al.

(10) Patent No.: US 12,417,645 B2
(45) Date of Patent: Sep. 16, 2025

(54) MULTIPLE IMAGE SEGMENTATION AND/OR MULTIPLE DYNAMIC SPECTRAL ACQUISITION FOR MATERIAL AND MINERAL CLASSIFICATION

(71) Applicant: FEI Company, Hillsboro, OR (US)

(72) Inventors: Darius Kocár, Portland, OR (US); Michael James Owen, Brisbane (AU)

(73) Assignee: FEI Company, Hillsboro, OR (US)

( * ) Notice: Subject to any disclaimer, the term of this patent is extended or adjusted under 35 U.S.C. 154(b) by 586 days.

(21) Appl. No.: 17/707,804

(22) Filed: Mar. 29, 2022

(65) Prior Publication Data
US 2022/0319206 A1    Oct. 6, 2022

(30) Foreign Application Priority Data

Mar. 31, 2021    (EP) .................................... 21166396

(51) Int. Cl.
*G06V 20/69*    (2022.01)
*G01N 23/203*    (2006.01)
(Continued)

(52) U.S. Cl.
CPC ......... *G06V 20/693* (2022.01); *G01N 23/203* (2013.01); *G01N 23/2206* (2013.01);
(Continued)

(58) Field of Classification Search
CPC .. G06V 20/693; G06V 10/143; G06V 10/267; G06V 20/695; G06V 20/698;
(Continued)

(56) References Cited

U.S. PATENT DOCUMENTS

| 2010/0191506 A1 | 7/2010 | Chyba et al. |
| 2013/0015351 A1* | 1/2013 | Kooijman ............... H01J 37/28 250/307 |

(Continued)

FOREIGN PATENT DOCUMENTS

| EP | 2546638 A2 | 1/2013 |
| EP | 3217420 A1 * | 9/2017 ........... G01N 23/225 |

(Continued)

OTHER PUBLICATIONS

Burdet P, Croxall SA, Midgley PA. Enhanced quantification for 3D SEM-EDS: using the full set of available X-ray lines. Ultramicroscopy. Jan. 2015; 148:158-167. doi: 10.1016/j.ultramic.2014.10.010. Epub Oct. 29, 2014. (Year: 2014).*

(Continued)

*Primary Examiner* — Wassim Mahrouka

(57) ABSTRACT

The invention relates to method and system configured for material analysis and mineralogy. At least one image based on first emission from a sample is provided. First spectra of the sample based on second emissions from the second scan locations of the image are provided. A confidence score is calculated for every first spectrum, and second scan location (s) with confidence score(s) below a threshold value are selected. Second emissions from the selected second scan location(s) are acquired to provide new image and determine new second scan locations within the respective new image.

20 Claims, 9 Drawing Sheets

(51) Int. Cl.
*G01N 23/2206* (2018.01)
*G01N 23/223* (2006.01)
*G06V 10/143* (2022.01)
*G06V 10/26* (2022.01)

(52) U.S. Cl.
CPC ......... *G01N 23/223* (2013.01); *G06V 10/143* (2022.01); *G06V 10/267* (2022.01); *G06V 20/695* (2022.01); *G06V 20/698* (2022.01)

(58) Field of Classification Search
CPC .. G06V 20/69; G01N 23/203; G01N 23/2206; G01N 23/223; G01N 33/24; G01N 2223/053; G01N 2223/606; G01N 2223/641; G01N 2223/66; G01N 23/2252; G01N 23/2251; H01J 2237/24415; H01J 2237/24495; H01J 2237/28
See application file for complete search history.

(56) References Cited

U.S. PATENT DOCUMENTS

| | | | |
|---|---|---|---|
| 2013/0054153 A1 | 2/2013 | Motl et al. | |
| 2014/0001356 A1 | 1/2014 | Buhot et al. | |
| 2014/0220712 A1 | 8/2014 | Okabe et al. | |
| 2014/0247379 A1* | 9/2014 | Najmabadi | G01N 21/6458 |
| | | | 348/295 |
| 2016/0372304 A1* | 12/2016 | Masnaghetti | G01N 23/203 |
| 2018/0003651 A1* | 1/2018 | Patel | G01N 23/20058 |
| 2019/0095678 A1* | 3/2019 | Aragaki | G06T 7/50 |
| 2021/0102907 A1* | 4/2021 | Couture | G01N 23/203 |
| 2022/0221412 A1* | 7/2022 | Goran | G01N 23/2055 |
| 2023/0296540 A1* | 9/2023 | Osterreicher | G01N 23/2252 |
| | | | 250/307 |

FOREIGN PATENT DOCUMENTS

| | | |
|---|---|---|
| EP | 2546638 | 8/2019 |
| GB | 2223842 | 4/1990 |
| JP | 2003254920 A | 9/2003 |
| JP | 2013019900 A | 1/2013 |

OTHER PUBLICATIONS

Lorenz, S.; Seidel, P.; Ghamisi, P.; Zimmermann, R.; Tusa, L.; Khodadadzadeh, M.; Contreras, I.C.; Gloaguen, R. Multi-Sensor Spectral Imaging of Geological Samples: A Data Fusion Approach Using Spatio-Spectral Feature Extraction. Sensors 2019, 19, 2787. https://doi.org/10.3390/s19122787 (Year: 2019).*

Reehl, Sarah M., et al. Mirostructure Characterization of Friction Consolidated Copper-Nickel using a Machine Learning Approach: Developing Process to Microstructure Associations. No. PNNL-30565. Pacific Northwest National Laboratory (PNNL), Richland, WA (United States), 2020. (Year: 2020).*

Guntoro Pratama Istiadi et al., Application of machine learning techniques in mineral phase segmentation for X-ray microcomputed tomography (CT) data, Minerals Engineering, Aug. 23, 2019, vol. 42, Elsevier, Amsterdam, NL.

Extended European Search Report for Application No. 21166396.8, issued Sep. 9, 2021.

* cited by examiner

MULTIPLE IMAGE SEGMENTATION AND/OR MULTIPLE DYNAMIC SPECTRAL ACQUISITION FOR MATERIAL AND MINERAL CLASSIFICATION

FIELD

The present invention relates to the field of spectroscopy and image analysis. The present invention further relates to determining the properties of a sample or sections thereof, e.g. by means of a multiple image segmentation and/or a multiple dynamic spectral acquisition.

BACKGROUND

Material studies that involve characterizing the properties (e.g., structure, topography and chemical composition) of probes in the micro- and nanoscopic regime, can be performed through the implementation of scanning microscope systems, such as scanning electron microscopes (SEMs). A SEM is configured to scan the surface of the sample with a primary beam (i.e., an electron beam) and acquire an image of the sample based on various types of emissions e.g., emissions of backscattered, transmitted or secondary electrons. These emissions result from the interaction of the electron beam with the particles of the sample (such as atoms). In case of mineral studies, the sample consists of many thousands of mineral grains in particles embedded in an epoxy matrix.

Backscattered electrons (BSE) originate from the primary electron beam, which, as the name suggests, are reflected back (i.e., out of the sample) via elastic scattering on the sample atoms. The number of backscattered electrons at each scan location on the sample depends on the atomic number of the chemical elements (e.g., mineral elements) located in the corresponding scan location. Thus, the intensity variations (e.g., gray-level variations) within a BSE image are indicative of the compositional variations within the sample.

Along with the emissions of backscattered electrons, emissions of X-rays can also emerge from the interaction of the primary beam with the sample. In particular, characteristic X-rays are emitted when primary electrons cause the ejection of an electron in an inner shell of a sample atom, creating an electron hole. This electron hole is then filled by another electron from an outer atomic shell through the emission of an X-ray photon. The energy of that X-ray photon corresponds to the energy difference between the outer and inner shell. Thus, the emitted X-rays have energies that are unique for the corresponding chemical elements and their detection can therefore reveal the chemical composition of the sample. For the detection of X-ray emissions, SEMs are equipped with X-ray spectrometers that are configured to measure the number of detected X-rays with respect to their energies (energy-dispersive spectrometers, EDS) or their wavelengths (wavelength-dispersive spectrometers, WDS).

Material analysis (e.g., mineralogy classification) commonly involves coupling the backscattered electron imaging process with the application of X-ray spectroscopy. However, the X-ray acquisition takes a few milliseconds per scan location, while the BSE acquisition at each scan location can be three to four orders of magnitude faster. Thus, obtaining the compositional information of the entire sample based on the X-ray detection from tens or hundreds of thousands of scan locations can be highly time-consuming, lasting from several minutes to a few hours.

SUMMARY

In one embodiment, a system configured for material analysis and mineralogy, comprises a scanning microscope system, the scanning microscope system comprises a first detector and a second detector, and further comprising a data-processing system, the data-processing system comprising a data-storage component, and a first spectral analysis component; wherein the data-storage component is configured for providing at least one or a plurality of images of a sample or sections thereof based on first emissions detected by the first detector within a first dwell period from a plurality of first scan locations; wherein the second detector is configured for detecting second emissions for a second dwell period from at least one or a plurality of second scan locations of at least one region of the at least one image, each second scan location relating to a part of the corresponding region; wherein the data-storage component is configured for providing at least one or a plurality of first spectra, wherein each first spectrum is based on the second emissions detected at each of the second scan location(s) of the at least one region; wherein the first spectral analysis component is configured for calculating a confidence score for every first spectrum and selecting the second scan location(s) relating to the first spectrum(-a) with confidence score(s) below a threshold value; wherein the second detector is configured for detecting second emissions for a third dwell period from at least one of the selected second scan location(s) and/or wherein the data-storage component is configured for providing at least one or a plurality of new image(s) delimiting part(s) relating to the selected second scan location(s) and determining new second scan locations within the respective new image(s) through modified contrast and brightness values thereof with respect to the at least one image.

In another embodiment, a method for determining the properties of a sample or sections thereof, comprises: providing at least one or a plurality of images of the sample or sections thereof based on first emissions detected within a first dwell period from a plurality of first scan locations; performing a first detection step, comprising detecting second emissions for a second dwell period from at least one or a plurality of second scan locations of at least one region of the at least one image, each second scan location relating to a part of the corresponding region; performing a first spectrum providing step, comprising providing at least one or a plurality of first spectra, wherein each first spectrum is based on the second emissions detected at each of the second scan location(s) of the at least one region; performing a first spectral analysis step, comprising calculating a confidence score for every first spectrum and selecting the second scan location(s) relating to the first spectrum(-a) with confidence score(s) below a threshold value; performing a classification step, comprising detecting the second emissions for a third dwell period from at least one of the selected second scan location(s) and/or providing at least one or a plurality of new image(s) delimiting part(s) relating to the selected second scan location(s) and determining new second scan locations within the corresponding new image(s) through modified contrast and brightness values thereof with respect to the at least one image.

DETAILED DESCRIPTION

Figure 1:
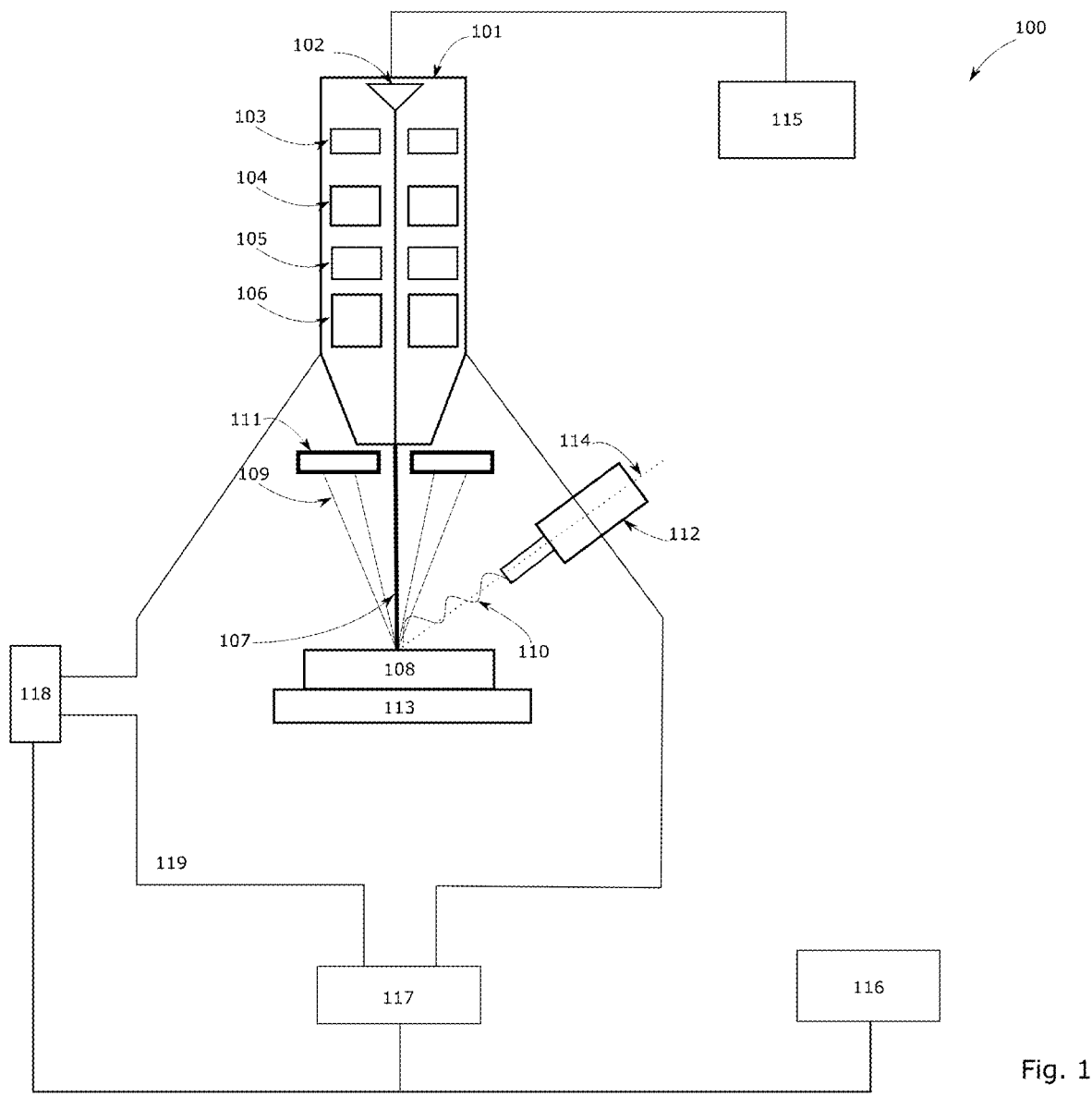
FIG. 1 shows a scanning microscope system.

A common measurement mode for material studies (e.g., mineralogy classification) that has been disclosed in the EP 2 546 638 B1, is to reduce the number of scan locations for the X-ray detection. This is done by acquiring a high-resolution BSE image and segmenting the image in order to identify parts (e.g., mineral grains) of the same intensity and thus the same chemical composition (e.g., mineral composition). For each identified mineral grain only one scan location is determined. The primary beam is then positioned at the scan location of each identified grain in order to detect the corresponding X-ray emissions and obtain the respective X-ray spectrum. Thus, mineral grains are initially distinguished based on their different intensities (e.g. gray level intensities) on the BSE image and their chemical composition is subsequently classified in the respective X-ray spectra.

In order to achieve a fast acquisition and maximize the acquisition throughput, a current solution is to perform the BSE image segmentation in parallel to the X-ray acquisition. This solution has been disclosed in another EP 2 021 792 8 A1, recently submitted by the FEI company. It is herewith incorporated by reference.

Even though most of the parts (e.g., mineral grains) in a sample are reliably identifiable (distinguishable) based on the X-ray spectra acquired within a few milliseconds (5-10 ms), Applicant recognizes that there is a small subset of minerals that produce similar X-ray spectra with other minerals. For example, various smectites might easily be confused with the illite mineral. Despite the fact that the illite mineral has a unique spectral line of potassium at an energy of 3.2 keV, structural rearrangements within the crystal structure (exchange of K with $H_3O$), can lead to a variable height of the potassium line. That way, the illite spectrum is losing its "uniqueness" and becomes indistinguishable from the smectite spectrum. Other examples of not easily identifiable mineral grains are the iron oxide minerals, hematite and magnetite ($Fe_2O_3$ and $Fe_3O_4$), as well as various copper sulfides (CuS, $Cu_2S$, etc.). The proper identification of these particular minerals can be of great economic importance in the industry. Mining companies for example are getting paid by a certain grade of iron and/or copper in the extracted minerals. Thus, knowing which iron oxide or copper sulfide is present in the ore deposits, can have a considerable impact on a company's profits.

Consequently, a reliable discrimination of chemically similar parts (e.g. mineral grains) requires an enhancement of the spectral quality (e.g. spectral resolution) of the corresponding X-ray spectra. An example of a current solution is to apply an automated X-ray acquisition on all parts (e.g. minerals) within a sample, with an increased integration time (i.e. dwell time) by a factor of ca. ten or higher (~100 ms). This leads to a high photon count detected for each mineral grain (up to 20.000 photons per spectrum), which subsequently improves the spectral quality and thus helps to resolve all minerals. However, this approach is a slow process with a low system throughput as it leads to an over acquisition of easily identifiable minerals that would otherwise require a much shorter dwell time to be identified (~5 ms). Thus, the current approach is commercially not feasible as companies would typically need to run multiple measurements to retrieve all the needed information from the targeted sample.

Material analysis (e.g. mineral classification) becomes particularly difficult when different parts (e.g. mineral grains) of a similar composition relate to a similar intensity on the BSE image, thus being segmented into a single part (i.e. single mineral phase). A current solution for this problem, is to manually find the not easily identifiable parts (e.g. minerals) in a high contrast and brightness mode, thus stretching the contrast and increasing the brightness of the selected part until two or more parts become visible. Re-acquiring the image of the sample with these modified contrast and brightness values and applying an image segmentation and X-ray acquisition on the newly revealed parts (e.g. mineral grains) helps determine their corresponding chemical composition (e.g. $Fe_2O_4$ and $Fe_3O_4$). However, with this workaround some other mineral grains in the sample might be depicted as too bright or as too dark by means of the modified contrast and brightness settings and therefore be regarded as background. Thus, this approach can lead to "clipping away" parts (e.g. mineral grains) that can introduce additional errors to statistical reports regarding properties of the targeted sample(s), such as the average sample content.

The present invention seeks to overcome or at least alleviate the shortcomings and disadvantages of the prior art. More particularly, it is an object of the present invention to provide an improved method, system and computer program product for material and mineral analysis.

It is an optional object of the invention to provide a system and method for determining the properties (e.g. chemical composition) of a sample and/or sections thereof. Particularly, it is an optional object of the present invention to allow for an image segmentation and an adjustable X-ray acquisition. It is another optional object of the invention to allow for a secondary dynamic X-ray acquisition and/or a secondary image segmentation on selected sections of the sample.

In a first embodiment, a system comprising a scanning microscope system and a data-processing system is disclosed. The system can be configured for providing at least one or a plurality of images of a sample and/or sections thereof based on first emissions detected within a first dwell period from a plurality of first scan locations. Further, the system can be configured for detecting second emissions for a second dwell period from at least one or a plurality of second scan locations of at least one region of the at least one image, each second scan location relating to a part of the corresponding region. Moreover, the system can be configured for providing at least one or a plurality of first spectra, wherein each first spectrum is based on the second emissions detected at each of the second scan location(s) of the at least one region. The system may also be configured for calculating a confidence score for every first spectrum and selecting the second scan location(s) relating to the first spectrum(-a) with confidence score(s) below a threshold value. Furthermore, the system can be configured for detecting the second emissions for a third dwell period from at least one of the selected second scan location(s) and/or providing at least one or a plurality of new image(s) delimiting part(s) relating to the selected second scan location(s) and determining new second scan locations within the corresponding new image(s) through modified contrast and brightness values thereof with respect to the at least one image.

The term "image" is intended to comprise a two-dimensional grid, wherein the two-dimensional grid can comprise at least one or a plurality of portions. Each portion is characterized by its coordinates and its value (color and/or intensity). Thus, the image may refer to a visual representation of the sample in color variations and/or intensity variations. For example, the image may comprise intensity variations of the same color, such as gray level variations. Further, each portion in the image may correspond to a point (e.g. scan point) on the sample. The image portions may for example be pixels or comprise a plurality of pixels.

Furthermore, the term "mask" is intended to comprise a binary image, comprising for example black and white portions. The portions of the one color and/or intensity (e.g. white portions) may be used for marking a section of the image for further processing. However, the term mask may also refer to the marked section of the image (e.g. white portions).

The term "spectrum" is intended to comprise a distribution function of a physical quantity (e.g. energy or frequency). A quantity measure may be for example the intensity, the abundance, the rate, or the flux of the respective quantity value. The spectrum may refer to a discrete spectrum, wherein the discrete spectrum may comprise a set of discrete spectral lines at different energy values. The peak of each spectral line at the corresponding line center may correspond to the maximum number of detected photons (i.e. peak intensity) over the respective line width. The detected photons may further refer to detected X-ray photons. Each spectral line may correspond to an electronic transition of a chemical element, wherein the energy value of each electronic transition may be unique for the corresponding chemical element. The spectrum may also refer to a continuous spectrum, wherein the continuous spectrum may refer to an intensity distribution over a range of continuous energy values. However, the intensity may also be plotted with respect to the corresponding wavelengths, frequencies or wavenumbers.

The term "particle" is intended to comprise a particle in the sample. The particles may correspond to regions. The term "region" may refer to a region of the sample corresponding to a particle or a portion thereof, e.g. when only a section of the sample is imaged and/or processed, which section only comprises a portion of a particle. The term "region" may also refer to a portion of the image, which portion corresponds to a particle in the sample.

The term "mineral grain" is intended to comprise a mineral grain within a particle located in the sample. The mineral grains may correspond to parts. The term "part" may refer to a part of the particle corresponding to a mineral grain or a portion thereof, e.g. when only a section of the particle is imaged and/or processed, which section only comprises a portion of a mineral grain. The term "part" may also refer to a portion of the image, which portion corresponds to a mineral grain within the particle located in the sample.

Whenever x-, y- and/or z-coordinates or directions are used within this disclosure, the z-direction may be vertical, in other words orthogonal to a ground surface. The x- and y-directions may be orthogonal to each other and to the z-direction, i.e. they may be horizontal directions. The coordinates may form a Cartesian coordinate system.

The term "scan location" is intended to comprise a location of a scan point in the sample. The location is given by (x,y)-coordinates with respect to an internal coordinate system of the sample and/or the image.

Moreover, the terms "second scan location(s)", "region(s)", image(s), spectrum(-a) and any other terms ending in -(s) or in -(-a) will be used together with the plural form of a verb for reasons of clarity and conciseness. However, these statements are intended to also cover at least one second scan location and at least one region etc.

In this disclosure, the term "time interval" is intended to comprise a period of time defined between two fixed times/events. The person in the skilled art will easily understand that two time intervals defined by the limits (t1, t2) and (t1', t2') with t1≤t1' and of the length w and w' respectively, are overlapping if the following condition is fulfilled: w+w'>t2'-t1. A first method step taking place for the duration of a first time interval and a second method step taking place within a second time interval are intended to comprise parallel steps, if the first and the second time interval overlap. Thus, two method steps are considered to be parallel if there is a partial or a full overlap of the corresponding time intervals.

The term "data set" is intended to comprise a collection of data. The term "data set" may also refer to a list of the (x,y)-coordinates of the corresponding second scan location(s). A synonym in this specification for "data set" is "group".

The scanning microscope system may comprise a first detector, wherein the first detector may be configured for detecting the first emissions from the first scan locations.

The first detector may comprise a backscattered electron detector.

The scanning microscope system may comprise a second detector, wherein the second detector may be configured for detecting the second emissions from the second scan location(s).

The second detector may comprise an X-ray detector.

The scanning microscope system may be configured for focusing a beam of charged particles (such as electrons) to a scan point on the sample.

The scanning microscope system may further be configured for scanning the beam of charged particles over a plurality of scan locations in one or two dimensions.

The scan locations may correspond to the first scan locations.

The scan locations may correspond to the second scan locations.

The data-processing system may be configured for assigning a two-dimensional coordinate system to the sample.

The data-processing system may also be configured for assigning the two-dimensional coordinate system of the sample to the at least one image.

Thus, the location of each portion in the image may be tracked as the beam of charged particles moves across the first scan locations of the sample.

Assigning the same coordinate system of the sample to the image may be accomplished by means of reference points of known coordinates, wherein the reference points may be incorporated in the sample or a movable stage.

A result of scanning the beam of charged particles over the scan locations of the sample may comprise an interaction of the beam with the sample.

A result of the interaction may comprise the first and/or the second emissions.

The first emissions may comprise emissions of particles (such as backscattered electrons).

The second emissions may comprise emissions of photons (such as X-ray photons).

The data-processing system may be configured for generating the at least one image based on the first emissions detected at each first scan location.

The at least one image may correspond to a backscattered electron image.

The at least one image may comprise a contrast and a brightness value.

Further, the at least one image may show intensity variations between the regions (and/or parts thereof) with different properties (such as chemical composition).

The intensity variations may comprise gray level variations. In particular, a gray level image may comprise 256 levels of gray, with the gray level values ranging from 0 to 255.

In fact, the gray level intensity of an image (or a part thereof) may be linearly related to the atomic number (e.g. average atomic number) of a corresponding section as given in the following expression:

$$I = C*S + B,\qquad \text{Equation 1:}$$

wherein 1 describes the gray level intensity, S is a factor related to the atomic number (e.g. average atomic number) of a targeted section (e.g. mineral grain) of the sample, and the C, B coefficients stand for the contrast and brightness values of the image. Thus, if the C, B coefficients of an image are known, the user may derive atomic number of the targeted section of the sample based on its corresponding gray level intensity on the image (see also Hardig (2002), "*Mineral identification using a scanning electron microscope*", Department of Metallurgical Engineering, University of Utah, Salt Lake City Utah).

Each region of the at least one image may correspond to a particle in the sample.

Moreover, each particle in the sample may comprise at least one or a plurality of mineral grain(s).

The scanning microscope system, particularly the first detector, may be configured for detecting the first emissions for the duration time of the first dwell period at each first scan location.

The scanning microscope system, particularly the second detector, may be configured for detecting the second emissions for the duration time of the second dwell period at each second scan location.

The second dwell period may be longer than the first dwell period. For example, the second dwell period may correspond to 8 ms, while the first dwell period may correspond to 1 μs.

The system may be configured for detecting the first emissions from the first scan locations and detecting the second emissions from the second scan location(s) at different time intervals, wherein the different time intervals correspond to non-overlapping time intervals.

The data-processing system may comprise a data-storage component, wherein the data-storage component may be configured for providing the at least one image of the sample (or sections thereof).

The data-processing system may comprise a first segmentation component, wherein the first segmentation component, may be configured for determining the second scan location(s) of the region(s) of the at least one image.

The first segmentation component may further be configured for determining each second scan location for the duration time of a segmentation period.

The segmentation period may depend on image properties, such as the resolution and the magnification of the at least one image (and/or sections thereof).

The segmentation period may also depend on the size of the mineral grain(s) and/or particle(s). Typical grain sizes may range from at least 1 μm to at most 500 μm.

Sample statistics, such as particle size, grain number per particle and size distribution over the sample, have low statistical spread throughout the same sample and/or a replicant sample. Thus, this may lead to low variations of the segmentation period from one second scan location to another.

The segmentation period may be shorter than or equal to the second dwell period. For example, the segmentation period may correspond on average to 3 ms and the second dwell period may correspond to 8 ms.

However, the segmentation period may also be longer than the second dwell period. This may be the case when the image (and/or sections thereof) is highly resolved and/or magnified and/or the size of the grains is considerable.

Generally, the resolution and the magnification of the at least one image may define the size of a portion (such as a pixel), ranging from at least 10 nm to at most 1000 nm. For example, a small portion size of 10 nm may be indicative of a high resolution and/or a high magnification. A smaller portion size may result to a higher number of portions representing the same part of the image (relating to a mineral grain).

In fact, the segmentation period may be slower with an increasing number of portions. For example, if a mineral grain of a medium size (such as 50 μm) is imaged with a high resolution and/or a high magnification (e.g. portion size of 20 nm) the resulting segmentation period may be very long (e.g. a factor of 10 longer than the second dwell period).

The data-processing system may comprise a pre-processing component.

The pre-processing component may be configured for applying a thresholding algorithm.

In particular, the thresholding algorithm may be configured for separating the at least one image into a background part and a foreground part based on a threshold intensity.

The background part may comprise background portions, wherein the background portions (e.g. pixels) may comprise intensities lower than the threshold intensity (e.g. dark gray and/or black portions).

The foreground part may comprise foreground portions, wherein the foreground portions (e.g. pixels) may comprise intensities higher than or equal to the threshold intensity (e.g. bright gray and/or white portions).

Delimiting and/or removing the background part may comprise assigning to the background portions the same color value and/or intensity value (e.g. black portions).

The foreground part may comprise at least some of the regions of the image.

Further, the pre-processing component may be configured for determining the boundaries of the corresponding regions of the at least one image by means of a contouring algorithm.

The contouring algorithm may be configured for joining adjacent portions along the boundaries of the corresponding regions to curves.

The adjacent portions along the boundaries of the corresponding regions may be surrounded by the background portions (e.g. black portions).

The pre-processing component may be further configured for applying a bounding box algorithm.

The bounding box algorithm may be configured for dividing the at least one image into at least one or a plurality of sub-images based on a result of the contouring algorithm.

A sub-image of the at least one image may be delimiting one region.

The data-processing system, particularly the data-storage component, may be configured for providing the sub-image(s).

The first segmentation component may be configured for correcting a sub-image generation error.

The sub-image generation error may comprise generating at least one sub-image containing at least two neighboring regions.

The at least two neighboring regions located within the one sub-image may correspond to touching particles in the sample.

At least one or more portions along the boundary of one of the neighboring regions may be contiguous with at least one or more portions along the boundary of another of the neighboring regions.

Correcting the sub-image generation error may comprise processing each of the neighboring regions within the one sub-image individually.

Further, the first segmentation component may be configured for processing the sub-images individually for the case of more than on sub-image being provided.

The first segmentation component may also be configured for determining the second scan location(s) for the sub-image(s).

In particular, the first segmentation component may be configured for assigning contiguous portions of parts of the corresponding regions within the respective sub-images to clusters by means of a k-means clustering algorithm.

Thus, each region of the respective sub-image may comprise at least one or a plurality of clusters.

The first segmentation component may further be configured for applying a flood fill algorithm, wherein the flood fill algorithm may be configured for generating a mask for at least one of the clusters.

Generating the mask for the at least one of the clusters may comprise assigning to contiguous portions within the corresponding cluster the same value of color and/or intensity.

Each mask may be delimiting a part of the corresponding region.

A part within each region of the at least one image may correspond to a mineral grain within the corresponding particle in the sample.

The first segmentation component may be configured for determining one second scan location for each mask.

Each second scan location may correspond to a centroid of the respective mask.

Moreover, the first segmentation component may be configured for correcting an over-segmentation error.

The over-segmentation error may comprise determining more than one second scan location for at least one of the masks.

Thus, the first segmentation component may be configured for merging the second scan locations for the at least one of the masks into one second scan location by means of a merging operator.

The data-processing system may be configured for generating first data set(s) for the region(s) within the respective sub-image(s).

A first data set may comprise a list of the coordinates of the second scan location(s) relating to one of the regions.

The data-storage component may be configured for providing at least one of the first data sets.

The scanning microscope system may be configured for focusing the beam on at least one of the second scan locations of the at least one of the first data sets.

The second detector may be configured for detecting the corresponding second emissions emerging from the corresponding second scan location(s) of the first data set(s) upon irradiation of the sample with the beam.

The first segmentation component may be configured for processing the at least one or more sub-images for the duration of a first time interval. The first time interval may correspond to a difference between an initial time and a final time. The initial time may correspond to the time at which the segmentation component determines the first of the second scan location(s) of the first of the sub-images. The final time may correspond to the time at which the segmentation component determines the last of the second scan location(s) of the last of the sub-images.

Moreover, the scanning microscope system may be configured for focusing the beam on the second scan location(s) of the corresponding first data set(s) and detecting the corresponding second emissions for the duration of a second time interval. The second time interval may correspond to a difference between another initial time and another final time. The other initial time may correspond to the time at which the second detector detects the second emissions from the first of the second scan location(s) of the first of the first data sets. The other final time may correspond to the time at which the second detector detects the second emissions from the last of the second scan location(s) of the last of the first data sets (relating to the last sub-image).

The system may further be configured for determining the second scan location(s) for the sub-images and detecting the second emissions from the at least one of the second scan locations of the first data sets in parallel for the case of more than one sub-image (i.e. first data set) being provided.

In other words, the first time interval and the second time interval may overlap. In this example, the system may be configured for detecting the second emissions from the second scan location(s) within the first data set of one sub-image (sequentially), while at the same time selecting another sub-image and generating another set of second scan locations (sequentially). The system may be configured for repeating the process until all of the sub-images have been selected and processed. In general, a parallel implementation of two method steps may correspond to a partial or a full overlap of the corresponding time intervals. The above considerations may apply to other following parallel steps.

The data-processing system may be configured for generating the first spectrum(-a) based on the second emissions (i.e. number of photons) detected at each of the second scan location(s) of the at least one sub-image (i.e. first data set).

The data-processing system (800), particularly the data-storage component (810), may be configured for providing the first spectrum(-a).

Each first spectrum may correspond to an X-ray spectrum, wherein the X-ray spectrum comprises at least one or a plurality of spectral lines.

The X-ray spectrum may further comprise the number of detected X-ray photons (i.e. spectral line intensity) at the respective energies.

Each spectral line may correspond to an electronic transition of a chemical element.

Each mineral grain of the sample may comprise at least one or a plurality of chemical elements.

Thus, the X-ray spectrum may comprise information about the chemical composition (e.g. mineral composition) of the corresponding mineral grain relating to the respective second scan location.

The data-processing system may further comprise a first spectral analysis component.

The data-processing system, particularly the first spectral analysis component, may be configured for analyzing each first spectrum from the respective second scan location of the at least one of the regions (i.e. first data sets).

Analyzing each first spectrum may comprise comparing the respective first spectrum with at least one or a plurality of reference spectra.

Each reference spectrum may comprise a plurality of pre-defined spectral lines relating to a known mineral grain.

The first spectral analysis component may comprise a first line assignment component, wherein the first line assignment component may be configured for assigning the spectral line(s) of each first spectrum to the pre-defined spectral lines of the reference spectrum(-a).

Thus, the data-processing system, particularly the first spectral analysis component may be configured for matching each first spectrum to one of the known mineral grains based on a result of the first line assignment component.

The data-processing system, particularly the first spectral analysis component may be configured for calculating the confidence score for every first spectrum, wherein the confidence score may correspond to the level of agreement between the first spectrum and the corresponding matched reference spectrum.

In other words, the confidence score may describe the probability of the respective first spectrum belonging to one of the known mineral grains.

In particular, the confidence score may correspond to a numeric value, wherein the numeric value may range from 0 to at most 1 and may be assigned to each first spectrum.

The system may be configured for pre-setting the threshold value for the confidence score.

A high confidence score (above or equal to the threshold value) may correspond to a reliable identification of the chemical composition of the respective mineral grain based on the corresponding first spectrum. For example, a high confidence may correspond to a numeric value of 0.95 or more. The confidence score may also be expressed as a probability percentage, e.g. 95%.

On the other hand, a low confidence score (below the threshold value) may correspond to a partial identification of the chemical composition of the respective mineral grain based on the corresponding first spectrum. For example, this might be the case if a plurality of the spectral lines of the corresponding first spectrum can be assigned to more than one mineral grains (due to their similar chemical composition). Other spectral lines that would be unique to only one of the candidate mineral grains may comprise an insufficient line intensity.

In other words, a mineral grain of low confidence score may have a similar chemical composition with at least another mineral grain.

Thus, the mineral grains of a similar chemical composition may comprise at least one or a plurality of common chemical elements.

The mineral grains of a similar chemical composition may therefore correspond to similar first spectra. In fact, similar first spectra may comprise at least one or a plurality of common spectral lines.

Furthermore, mineral grains of a similar chemical composition may comprise the same chemical elements with a different elemental ratio. For example, the minerals $Fe_2O_3$ and $Fe_3O_4$, also known as hematite and magnetite, respectively, are both iron oxides but with a different content on iron (and oxygen). Thus, the corresponding first spectra may comprise the same spectral lines (at the same energies) but with different intensity ratios (e.g. ratio of iron line intensity to oxygen line intensity within the respective first spectrum).

As mentioned above, the low confidence score may result from a low spectral quality of the respective first spectrum, wherein the low spectral quality may result from spectral lines of the respective first spectrum comprising an insufficient spectral line intensity. The insufficient line intensity may result from an insufficient number of photons detected during the second dwell period (i.e. number of detected photons per time).

The system, particularly the data-processing system, may be configured for estimating an intrinsic photon count rate based on the number of photons detected during the second dwell period (i.e. number of detected photons per time).

The intrinsic photon count rate may depend on the chemical composition of the corresponding part (i.e. mineral grain).

The intrinsic photon count rate may also depend on the sample properties, such as crystal properties (e.g. orientation, size, depth), of the corresponding part (i.e. mineral grain).

The system, particularly the data-processing system, may be further configured for generating at least one or a plurality of second data set(s), wherein each second data set may comprise a list of the coordinates of the second scan location(s) relating to the mineral grain(s) of low confidence score of at least one or more regions (i.e. sub-images) of the at least one image.

The data-processing system, particularly the data-storage component, may be configured for providing the second data set(s).

The system may further be configured for detecting the second emissions from the second scan locations of the first data set(s) and providing the first spectra in parallel for the case of more than second scan location being processed. The first spectra may be provided in batches, wherein each batch of first spectra may result from the second scan locations of one or more sub-images.

Moreover, the system may be configured for detecting the second emissions from the second scan locations of the first data set(s) and analyzing the first spectra in parallel for the case of more than one first spectrum being provided.

The data-processing system, may comprise a one-pass classification component.

Further, the data-processing system, may comprise a two-pass classification component.

The system, particularly the data-processing system, may be configured for executing the one-pass and/or the two-pass classification component based on a result of the first spectral analysis component. In fact, the system may be configured for applying the one-pass classification component on the second scan location(s) of the second data set(s) relating to mineral grains that comprise a similar chemical composition with at least one or more other mineral grains. Moreover, the system may be configured for applying the two-pass classification component on the second scan location(s) of the second data set(s) relating to specific mineral grain(s). Apart from a similar composition, a specific mineral grain may further comprise a similar gray level intensity on the at least one image with at least one other specific mineral grain (see below for further information).

In both cases the selected second scan locations may refer to mineral grains (and first spectra) of low confidence score. The system may also be configured for executing the one-pass and the two-pass classification components or parts thereof in parallel. For example, the system may be configured for applying the one-pass classification component on one second scan location of a corresponding second data set while applying the two-pass classification component on another second scan location of the same second data set. Additionally, or alternatively, the system may also be configured for applying the one-pass classification component on second scan location(s) of one second data set while applying the two-pass classification component on other second scan location(s) of another second data set. Additionally, or alternatively, the system may be configured for applying the two classification steps separately (i.e. in different, non-overlapping time intervals).

Furthermore, the system, particularly the data-processing system, may be configured for executing the one-pass and/or the two-pass classification component after the second detector has completed detecting the second emissions from the second scan location(s) of at least some or all of the first data set(s) of the at least one image.

The system, particularly the scanning microscope system, may be configured for focusing the beam on at least one of the second scan location(s) of the second data set(s).

The scanning microscope system, particularly the second detector, may be configured for detecting the second emissions from each second scan location of the second data set(s) upon irradiation of the sample with the beam.

The scanning microscope system, particularly the second detector, may be configured for detecting the second emissions for the duration time of the third dwell period from the at least one second scan location of the second data set(s).

The data-processing system, particularly the one-pass classification component may be configured for determining the third dwell period for the at least one second scan location of the second data set(s) based on the calculated confidence score of the respective first spectrum and the intrinsic photon count rate of the corresponding mineral grain. Thus, this may be optionally advantageous, as it may allow the system to dynamically adjust and optimize the acquisition of the second emissions (e.g. X-rays) for every selected second scan location of the second data set(s).

In fact, the third dwell period may be higher than the second dwell period for the corresponding second scan location(s). For example, the third dwell period can be a factor of 2 to 10 times higher than the second dwell period. Thus, the second detector may be configured for detecting a higher number of photons (i.e. X-ray photons) within the third dwell period (with respect to the second dwell period).

However, the third dwell period may also be lower than or equal to the second dwell period for the corresponding second scan location(s).

The data-processing system, particularly the one-pass classification component may be configured for adding the number of photons (e.g. X-ray photons) detected within the second dwell period to the number of photons (e.g. X-ray photons) detected within the third dwell period at the respective second scan location of the second data set.

The data-processing system, particularly the one-pass classification component ($850a$), may also be configured for generating at least one or a plurality of second spectra, wherein each second spectrum may comprise the total number of detected photons (e.g. X-ray photons) at the corresponding second scan location of the second data set. Thus, optionally advantageously, the second spectra may comprise a higher spectral intensity and/or resolution than the first spectra of the corresponding selected second scan locations.

The data-processing system, particularly the data-storage component, may be configured for providing the second spectra in groups, wherein each group comprises the second spectra obtained from the at least one or more images. In particular, the system may be configured for acquiring grids of images, wherein each grid may comprise for example 8×8 images. Each image within the respective grid may depict a section of the sample and thus, a grid of images may depict neighboring sections of the sample. Thus, a group may then comprise the second X-ray spectra acquired from all images (8×8 images) within the corresponding grid.

Each second spectrum may correspond to an X-ray spectrum.

The data-processing system, particularly the one-pass classification component, may be configured for correcting an image generation error for the case that a group comprises the second spectra obtained from at least two images, wherein the at least two images may show neighboring sections of the sample.

The at least two images may contain at least two parts belonging to one of the mineral grains of low confidence score. In other words, a portion of one mineral grain of low confidence score may be depicted in one of the two images and another portion of the same mineral grain may be depicted in the other of the two images.

Correcting the image generation error may comprise stitching the at least two parts of the at least two images.

Thus, the data-processing system, particularly the one-pass classification component, may be configured for summing the second spectra of the parts belonging to the same mineral grain of low confidence score by means of another merging operator.

Further, the data-processing system, particularly the one-pass classification component, may comprise a second spectral analysis component.

The one-pass classification component, particularly the second spectral analysis component, may be configured for analyzing the second spectra of each group individually.

In particular, the second spectral analysis component may be configured for matching each second spectrum to at least two known mineral grains based on a result of a second line assignment component.

The data-processing system, particularly the second spectral analysis component, may be configured for calculating at least two or a plurality of new confidence scores for every second spectrum, wherein each new confidence score corresponds to the level of agreement between the second spectrum and the corresponding matched reference spectrum.

The one-pass classification component may be configured for selecting the highest new confidence score out of the at least two new confidence scores for every second spectrum.

The highest new confidence score(s) of at least some of the second spectra may correspond to a high confidence score (above or equal to the threshold value). In other words, the statistical average of the highest new confidence scores of all the second spectra may correspond to a high confidence score.

Thus, the data-processing system, particularly the one-pass classification component, may be configured for normalizing the data quality of at least some of the mineral grains of (initial) low confidence score. For example, a mineral grain may be initially assigned to chalcolite ($Cu_2S$) with an accuracy of 86% while another mineral grain of the same sample may be assigned to digenite ($Cu_9S_5$), with an accuracy of 74%. After the one-pass classification process is completed, both minerals may be identified respectively as chalcolite and digenite with a 99.9% accuracy.

Thus, optionally advantageously, the one-pass classification process may allow to reduce the overall acquisition time since non-ambiguous mineral grains can be identified with minimal photons, while the mineral grains that are increasingly similar in chemical composition are selected for a second round of X-ray detection, thus acquiring additional photons. As mentioned above, the acquisition of additional photons leads to highly-resolved second spectra that may help to accurately identify the mineral grains with a similar chemical composition to each other.

In other words, the one-pass classification component may be configured for detecting on average at least $2 \times 10^3$ photons and at most $3 \times 10^3$ photons per second scan location instead of approximately $2 \times 10^4$ photons per second scan location as done in previous and slower methods of the prior art. Thus, optionally advantageously, the one-pass classification step may be faster than conventional classification processes by several factors and by a factor of at least 5, and preferably by a factor of at least 10.

The system may be further configured for detecting the second emissions from the second scan location(s) of the second data sets and analyzing the first spectra in parallel. In other words, once the system has finished detecting the second emissions from the second scan locations of the first data sets, the system immediately starts the second round of detection (on the second scan location(s) of the second data sets) while finishing the first spectral analysis component on the remaining second scan locations of the first data sets.

The system, particularly the data-processing system, may be configured for executing the second spectral analysis component after the first spectral analysis component has completed analyzing at least some or all of the first spectra relating to the at least one or more images.

Moreover, the system may be configured for detecting the second emissions from the second scan locations of the second data set(s) and analyzing the second spectra in parallel.

In other words, the system may be configured for analyzing a first group of second spectra relating to first image(s) while in parallel detecting the second emissions from second scan locations relating to second image(s).

As mentioned above, at least one or more of the mineral grain(s) of low confidence score relating to the second data set(s) may correspond to the specific mineral grain(s). A specific mineral grain may be depicted with the same or a similar intensity (i.e. gray level intensity) on the at least one image as at least one other specific mineral grain.

Thus, one of the specific mineral grains may be indistinguishable from the at least one other specific mineral grain on the at least one image. The specific mineral grains may have been determined as such from previous measurements on replicant samples. The system may further comprise a list of the specific mineral grains requiring further processing. Once a first spectrum is matched to one of the specific mineral grains of that list (with a low confidence score), the system may get notified of having a possible case of a not properly segmented part of the at least one image. An example of a pair of such specific mineral grains may comprise the mineral grains $Fe_2O_3$ and $Fe_3O_4$.

Moreover, the part(s) of the selected second scan location(s) relating to the specific mineral grain(s) may correspond to specific part(s) of the corresponding sub-image.

The system, particularly the data-processing system, may be configured for executing the two-pass classification component on the selected second scan location(s) of the second data set(s) relating to the specific part(s) of the corresponding sub-image(s).

Furthermore, the system may be configured for pre-setting and/or controlling the contrast and brightness values of a corresponding image (e.g. the at least one image or sections thereof) by adjusting operational settings of the first detector prior to the detection of the corresponding first emissions. Controlling the contrast and brightness values may comprise changing the operational settings with respect to a set of default operational settings. The system may be configured for setting the brightness value of the at least one image to be equal to a midpoint or another estimation of the gray level intensities of the specific parts. The system may further be configured for increasing the contrast in order to utilize full pixel depth over the grain intensity variations. This step may correspond to an automated method step executed by a corresponding algorithm.

Adjusting the operational settings of the first detector may comprise adjusting the gain factor of at least one or more amplifier(s) integrated within the first detector.

Additionally, or alternatively, adjusting the operational settings of the first detector may comprise adjusting the code width of an analog to digital converter (AD converter) integrated within the first detector.

The system, particularly the scanning microscope system, may be configured for focusing the beam on the first scan locations within the specific part(s) of the corresponding sub-image(s).

The scanning microscope system, particularly the first detector, may be configured for re-detecting the first emissions from the first scan locations of the corresponding specific part(s) upon irradiation of the beam with the sample.

The data-processing system, particularly the two-pass classification component, may be configured for generating at least one or a plurality of new sub-image(s), wherein each new sub-image is based on the first emissions re-detected at each specific part.

The system may further be configured for acquiring the new sub-image(s) with the adjusted contrast and brightness values (with respect to the at least one image) by pre-setting accordingly the operational settings of the first detector (as mentioned above). The adjusted contrast value may correspond to an increased contrast value. The adjusted contrast and brightness values may be different from one specific part to another.

The data-processing system, particularly the data-storage component, may be configured for providing the new sub-image(s).

The new image(s) may correspond to the new sub-image(s). Moreover, the part(s) delimited by the new image (s) may correspond to the specific part(s) delimited by the new sub-image(s). Thus, each new sub-image contains one of the specific part(s) of the respective sub-image.

The data-processing system, particularly the two-pass classification component, may be further configured for revealing and/or detecting at least two or a plurality of new part(s) within at least one of the new sub-images by means of the adjusted contrast and brightness values of the respective new sub-image.

Each new part may correspond to a section of the specific part within the respective new sub-image.

The data-processing system, particularly the two-pass classification component, may be configured for identifying at least two mineral grains within the at least one new sub-image based on the different intensity (e.g. gray level intensity) of the respective new parts, wherein the two mineral grains are indistinguishable on the at least one image (and sub-image) and wherein one of the mineral grains may correspond to the specific mineral grain of the specific part. For example, if the specific part may have been initially assigned to the specific mineral grain $Fe_2O_3$ with a low confidence score and the adjusted contrast and brightness values of the new sub-image reveal two new parts, then the one new part may relate to $Fe_2O_3$ and the other new part may relate to $Fe_3O_4$. In other words, the specific part may correspond to both iron oxide minerals but due to the low and/or non-optimal contrast and brightness values of the respective sub-image (and image) appeared to be containing only one.

If new parts within one of the new sub-images are not revealed, the two-pass classification component may be further configured for confirming that the specific part corresponds to only one mineral grain.

The two-pass classification component may further comprise a second segmentation component.

The two-pass classification component, particularly the second segmentation component, may be configured for processing the new sub-images individually for the case of more than one new sub-image being provided.

The two-pass classification component, particularly the second segmentation component, may be configured for generating a new second scan location for each of the new part(s) within the at least one new sub-image by means of the k-means clustering algorithm and the flood fill algorithm.

The two-pass classification component, particularly the second segmentation component, may be configured for determining each new second scan location for the duration time of another segmentation period.

The data-processing system, particularly the two-pass classification component, may be configured for generating third data sets, wherein each of the third data sets may comprise a list of the coordinates of the new second scan locations relating to one of the new sub-images.

The data-processing system, particularly the data-storage component, may be configured for providing at least one of the third data sets.

The system, particularly the scanning microscope system, may be configured for focusing the beam on at least one of the new second scan locations of the at least one third data set.

The scanning microscope system, particularly the second detector, may be configured for detecting the second emissions from the new second scan locations of the third data set(s) upon irradiation of the sample with the beam.

The scanning microscope system, particularly the second detector, may be configured for detecting the second emissions for the duration time of another third dwell period at every new second scan location of the third data set(s). The other third dwell period may vary from one new second scan location to another within the same third data set and/or among different third data sets.

The system may also be configured for determining the new second scan location(s) for the new sub-images and detecting the second emissions from the new second scan location(s) of the third data sets in parallel for the case of more than one new sub-image being provided.

Furthermore, the system may be configured for determining the new second scan locations of the third data sets and analyzing the first spectra in parallel. In other words, once the system has finished detecting the second emissions from the second scan locations of the first data sets, the system immediately starts acquiring and segmenting the new sub-image(s) (relating to the second scan location(s) of the second data sets) while finishing analyzing the first spectra of the remaining second scan locations of the first data sets.

Thus, the system may also be configured for detecting the second emissions from the new second scan locations of the third data set(s) and analyzing the first spectra in parallel.

The data-processing system, particularly the two-pass classification component, may further be configured for generating at least one or a plurality of new spectra, wherein each new spectrum may be based on the second emissions detected at the respective new second scan location of the at least one third data set.

The data-processing system, particularly the data-storage component, may be configured for providing the new spectra in other groups, wherein each other group comprises the new spectra obtained from the at least one or more images.

The data-processing system, particularly the two-pass classification component, may be configured for correcting the image generation error as done by the one-pass classification component.

The two-pass classification component may comprise another second spectral analysis component, wherein the other second spectral analysis component may comprise analyzing the new spectra of each other group individually.

The two-pass classification component, particularly the other second spectral analysis component, may be also configured for comparing each new spectrum to the reference spectra and calculating at least two or more other new confidence scores as done by the second spectral analysis component.

The data-processing system, particularly the two-pass classification component, may be configured for executing the other second spectral analysis component after the first spectral analysis component has completed analyzing at least some or all of the first spectra relating to the at least one or more images.

The system may be also configured for detecting the second emissions from the new second scan locations of the third data sets and analyzing the new spectra relating to the new second scan locations in parallel.

In fact, the system may be configured for analyzing a first other group of new spectra relating to first image(s) while in parallel detecting the second emissions from the new second scan locations relating to second image(s).

The system, particularly the two-pass classification component, may be configured for identifying and classifying the at least two specific mineral grains within the same new sub-image based on a result of the second segmentation component and the other second spectral analysis component. In other words, the gray level intensity may reveal for example which mineral grain out of the at least two may be the lightest (low average atomic number, e.g. $Fe_2O_3$) and which may be the heaviest (high average atomic number, e.g. $Fe_3O_4$) within the same new sub-image, since the intensity is related to the atomic number (e.g. average atomic number) of the respective mineral grain. Thus, the system may be configured for providing complementary information to the respective new spectra and give as a result a reliable classification of the specific mineral grains within the corresponding new sub-image.

Thus, optionally advantageously, the system may allow to automatically pre-select the mineral grains of interest and further process them, without re-processing the easy-identifiable grains. Consequently, the system may be advantageous as it may allow to correctly distinguish between similar (i.e. specific) mineral grains within a sample in a fully automated and multimodal process while maintaining a high system throughput.

The third dwell period may be longer than the first dwell period.

The other third dwell period may be longer than the first dwell period.

The other segmentation period may be higher than the other third dwell period. However, the other segmentation period may be lower than or equal to the other third dwell period. Just like the segmentation period of the first segmentation component, the other segmentation period may also depend on the grain size and the image properties.

Further, operating the (first and second) segmentation components and the (first, second, other second) spectral analysis components (i.e. computational resource) in parallel with the scanning microscope system (i.e. first and second detector, instrumentational resource) may be optionally advantageous, as it may allow to increase the total resource utilization of the system.

The data-processing system may further comprise a post-processing component.

The post-processing component may be configured for acquiring other images from other sections of the sample and/or replicant samples with the localized contrast and brightness values of the at least one of the new sub-images.

The post-processing component may be configured for applying a calibration model, wherein the calibration model may be configured for relating the chemical composition of the mineral grain(s) (e.g. average atomic number) of the sample to the gray level intensity(-ies) of the corresponding parts on the respective other image.

The calibration model may correspond to a linear regression (see above, Equation 1: $I=C*S+B$).

Moreover, the calibration model may comprise the contrast and the brightness values as model parameters (i.e. fitting parameters).

Applying the calibration model may comprise using known mineral grains (i.e. mineral elements) and their corresponding gray level intensities in the respective other image to calibrate and further constrain the localized contrast and brightness values. When using more than two known mineral grains (i.e. mineral elements), these values can be determined with a higher accuracy. Thus, the user may obtain a calibration curve for the targeted sample or a section thereof.

Thus, optionally advantageously, the post-processing component may be configured for determining the chemical composition of unknown mineral grain(s) of the other sections of the sample and/or the replicant samples based on the corresponding calibration curves (i.e. based on their detected gray level intensity(-ies) and the calibrated contrast and brightness values).

The system may be a system configured for material analysis and mineralogy.

The sample may comprise a plurality of particles embedded in an epoxy matrix.

The size of each mineral grain may comprise dimensions ranging from at least 1 μm to at most 500 μm.

The scan point may comprise dimensions of at most a micron.

A portion (such as a pixel) of the at least one image may comprise dimensions ranging from at least 10 nm to at most 1000 nm.

The second dwell period may range from at least 1 ms to at most 10 ms.

The system may further comprise a control unit, wherein the control unit may be configured for controlling the power supply and the operation of some of the components of the scanning microscope system, such as a condensing lens, an objective lens, a scanning coil and the movable stage.

The system may also comprise a vacuum system, wherein the vacuum system may comprise a vacuum controller, a mechanical pumping system, an ultra-high vacuum pump and a vacuum chamber.

The mechanical pumping system and the ultra-high vacuum pump may be configured for providing an ultra-high vacuum within the vacuum chamber.

The vacuum chamber may be configured for containing a sample, the movable stage, the first detector, the second detector or parts thereof, and a scanning electron microscope or parts thereof.

In a second embodiment, a method is disclosed. Definitions, details and advantages discussed above in the context of the system may apply respectively.

The method comprises providing at least one or a plurality of images of the sample or sections thereof based on first emissions detected within a first dwell period from a plurality of first scan locations. The method also comprises performing the first detection step. The first detection step comprises detecting second emissions for a second dwell period from at least one or a plurality of second scan locations of at least one region of the at least one image, each second scan location relating to a part of the corresponding region. The method further comprises performing the first spectrum providing step. The first spectrum providing step comprises providing at least one or a plurality of first spectra, wherein each first spectrum is based on the second emissions detected at each of the second scan location(s) of the at least one region. The method also comprises performing the first spectral analysis step. The first spectral analysis step comprises calculating a confidence score for every first spectrum and selecting the second scan location(s) relating to the first spectrum(-a) with confidence score(s) below a threshold value. Further, the method comprises performing the classification step. The classification step comprises detecting the second emissions for a third dwell period from at least one of the selected second scan location(s) and/or providing at least one or a plurality of new image(s) delimiting part(s) relating to the selected second scan location(s) and determining new second scan locations within the corresponding new image(s) through modified contrast and brightness values thereof with respect to the at least one image.

The method may further comprise a first segmentation step, wherein the first segmentation step may comprise determining the second scan location(s) of the region(s) of the at least one image.

The method may further comprise the step of focusing a beam of charged particles (such as electrons) to a scan point on the sample.

The method may further comprise scanning the beam of charged particles over a plurality of scan locations in one or two dimensions.

The scan locations may correspond to the first scan locations.

The scan locations may also correspond to the second scan locations.

Further, the method may comprise assigning a two-dimensional coordinate system to the sample.

The method may also comprise assigning the two-dimensional coordinate system of the sample to the at least one image.

A result of scanning the beam of charged particles over the scan locations of the sample may comprise an interaction of the beam with the sample.

Moreover, a result of the interaction may comprise the first and/or the second emissions.

The first emissions may comprise emissions of particles (such as backscattered electrons).

The second emissions may comprise emissions of photons (such as X-rays).

The method may further comprise detecting the first emissions from each first scan location.

Moreover, the method may comprise generating the at least one image based on the first emissions detected at each first scan location.

The at least one image may correspond to a backscattered electron image.

Further, the at least one image may show intensity variations between the regions (or parts thereof) with different properties (such as chemical composition).

The intensity variations may comprise gray level variations.

The at least one image may comprise a contrast and a brightness value.

Each region of the at least one image may correspond to a particle in the sample.

Each particle in the sample may comprise at least one or a plurality of mineral grains.

The method may further comprise detecting the first emissions for the duration time of the first dwell period at each first scan location.

The detection step may further comprise detecting the second emissions for the duration time of the second dwell period at each second scan location.

The second dwell period may be longer than the first dwell period.

The method may further comprise detecting the first emissions and detecting the second emissions at different time intervals, wherein the different time intervals may correspond to non-overlapping time intervals.

The first segmentation step may comprise determining each second scan location for the duration time of a segmentation period.

The segmentation period may depend on image properties, such as the resolution and the magnification of the at least one image (and/or sections thereof).

As mentioned above, the segmentation period may also depend on the size of the mineral grain(s) and/or particle(s). However, the variations of the segmentation period from one second scan location to another may be low within the same sample and/or a replicant sample due to a low statistical spread of the sample statistics (such as particle size and grain number per particle).

The segmentation period may be shorter than or equal to the second dwell period.

However, the segmentation period may be also longer than the second dwell period. In fact, large-sized mineral grains and/or particles that relate to parts and/or regions of the image with a large number of portions, may lead to a long segmentation period (i.e. slow segmentation process with respect to the detection process).

The method may further comprise a pre-processing step.

The pre-processing step may comprise applying a thresholding algorithm.

The thresholding algorithm may comprise separating the at least one image into a background part and a foreground part based on a threshold intensity.

The background part may comprise background portions, wherein the background portions (e.g. pixels) may comprise intensities lower than the threshold intensity (e.g. dark gray and/or black portions).

The foreground part may comprise foreground portions, wherein the foreground portions (e.g. pixels) may comprise intensities higher than or equal to the threshold intensity (e.g. bright gray and/or white portions).

The thresholding algorithm may comprise delimiting/removing the background part, wherein delimiting/removing the background part may comprise assigning to the background portions the same color value and/or intensity value (e.g. black portions).

The foreground part may comprise at least some of the regions of the image.

The pre-processing step may comprise determining the boundaries of the corresponding regions of the at least one image by means of a contouring algorithm.

The contouring algorithm may comprise joining adjacent portions along the boundaries of the corresponding regions to curves.

The adjacent portions along the boundaries of the corresponding regions may be surrounded by the background portions (e.g. black portions).

The pre-processing step may further comprise applying a bounding box algorithm, wherein the bounding box algorithm may comprise dividing the at least one image into at least two or a plurality of sub-images based on a result of the contouring algorithm.

A sub-image of the at least one image may be delimiting one region.

The first segmentation step may comprise correcting a sub-image generation error.

The sub-image generation error may comprise generating at least one sub-image containing at least two neighboring regions.

The at least two neighboring regions located within the one sub-image may correspond to touching particles in the sample.

At least one or more portions along the boundary of one of the neighboring regions may be contiguous with at least one or more portions along the boundary of another of the neighboring regions.

Correcting the sub-image generation error may comprise processing each of the neighboring regions within the one sub-image individually.

The method may further comprise performing the first segmentation step on the at least two sub-images individually.

The first segmentation step may comprise assigning contiguous portions of parts of the corresponding regions within the respective sub-images to clusters by means of a k-means clustering algorithm.

Thus, each region of the respective sub-image may comprise at least one or a plurality of clusters.

The first segmentation step may further comprise applying a flood fill algorithm, wherein the flood fill algorithm comprises generating a mask for at least one of the clusters.

Generating the mask for the at least one of the clusters may comprise assigning to contiguous portions within the corresponding cluster the same value of color and/or intensity.

Each mask may be delimiting a part of the corresponding region.

A part within each region of the at least one image may correspond to a mineral grain within the corresponding particle in the sample.

The first segmentation step may further comprise determining one second scan location for each mask.

Each second scan location may correspond to a centroid of the respective mask.

The method may further comprise generating first data sets for the regions within the respective sub-images.

A first data set may comprise a list of the coordinates of the second scan location(s) relating to one of the regions.

The method may further comprise providing at least one of the first data sets.

The first detection step may comprise focusing the beam on at least one of the second scan locations of the at least one of the first data sets.

The first detection step may further comprise detecting the second emissions from the corresponding second scan location(s) of the first data set(s) upon irradiation of the sample with the beam.

Thus, the method may comprise performing the first segmentation step and the first detection step in parallel for the case of more than one sub-image (i.e. first data set) being provided.

The method may comprise generating the first spectrum (-a) based on the second emissions (i.e. number of photons) detected at the corresponding second scan location(s) of the at least one sub-image (i.e. first data set).

Each first spectrum may correspond to an X-ray spectrum.

The X-ray spectrum may comprise at least one or a plurality of spectral lines.

The X-ray spectrum may comprise the number of detected X-ray photons (i.e. spectral line intensity) at the respective energies.

Each spectral line may correspond to an electronic transition of a chemical element.

Each mineral grain of the sample may comprise at least one or a plurality of chemical elements.

The X-ray spectrum may comprise information about the chemical composition (e.g. mineral composition) of the corresponding mineral grain relating to the respective second scan location.

The first spectral analysis step may comprise analyzing each first spectrum from the respective second scan location of the at least one of the regions (i.e. first data sets).

Analyzing each first spectrum may comprise comparing the respective first spectrum with at least one or a plurality of reference spectra.

Each reference spectrum may comprise a plurality of pre-defined spectral lines relating to a known mineral grain.

The first spectral analysis step may further comprise a first line assignment step, wherein the first line assignment step may comprise assigning the spectral line(s) of each first spectrum to the pre-defined spectral lines of the reference spectrum(-a).

The first spectral analysis step may comprise matching each first spectrum to one of the known mineral grains based on a result of the first line assignment step.

The confidence score may correspond to the level of agreement between the first spectrum and the corresponding matched reference spectrum.

Thus, the confidence score may describe the probability of the respective first spectrum belonging to one of the known mineral grains.

In fact, the confidence score may correspond to a numeric value, wherein the numeric value ranges from 0 to at most 1 and is assigned to each first spectrum.

Furthermore, the method may comprise pre-setting the threshold value for the confidence score.

Thus, a high confidence score (above or equal to the threshold value) may correspond to a reliable identification of the chemical composition of the respective mineral grain based on the corresponding first spectrum.

A low confidence score (below the threshold value) may correspond to a partial identification of the chemical composition of the respective mineral grain based on the corresponding first spectrum.

A mineral grain of low confidence score may have a similar chemical composition with at least another mineral grain.

In fact, the mineral grains of a similar chemical composition may comprise at least one or a plurality of common chemical elements.

Moreover, the mineral grains of a similar chemical composition may comprise the same chemical elements with a different elemental ratio (e.g. $Fe_2O_3$ and $Fe_3O_4$).

Thus, the mineral grains of a similar chemical composition may correspond to similar first spectra, wherein the similar first spectra may comprise at least one or a plurality of common spectral lines.

The similar first spectra may comprise the same spectral lines (at the same energies) with different intensity ratios.

The low confidence score may result from a low spectral quality of the respective first spectrum.

In particular, the low spectral quality may result from spectral lines of the respective first spectrum comprising an insufficient spectral line intensity, wherein the insufficient line intensity may result from an insufficient number of photons detected during the second dwell period.

The method may further comprise estimating an intrinsic photon count rate based on the number of photons detected during the second dwell period (i.e. number of detected photons per time).

The intrinsic photon count rate may depend on the chemical composition of the corresponding part (i.e. mineral grain).

The intrinsic photon count rate may also depend on the sample properties, such as crystal properties (e.g. orientation, size, depth), of the corresponding part (i.e. mineral grain).

Moreover, the method may further comprise generating and providing at least one or a plurality of second data set(s), wherein each second data set may comprise a list of the coordinates of the second scan location(s) relating to the mineral grain(s) of low confidence score of at least one or more regions (i.e. sub-images) of the at least one image.

The method may comprise performing the first detection step and the first spectrum providing step in parallel.

The method may also comprise performing the first detection step and the first spectral analysis step in parallel.

The classification step may comprise a one-pass classification step and/or a two-pass classification step.

The classification step may comprise performing the one-pass and/or the two-pass classification step based on a result of the first spectral analysis step.

Furthermore, the one-pass classification step may comprise performing the one-pass and/or the two-pass classification step after the first detection step has been essentially performed on the corresponding image.

The one-pass classification step may comprise performing the one-pass and/or the two-pass classification step after the first detection step has been completed.

The one-pass classification step may comprise a second detection step, wherein the second detection step may comprise focusing the beam on at least one of the second scan locations of the second data set(s).

As mentioned above, the second detection step may further comprise detecting the second emissions from each second scan location of the second data set(s) upon irradiation of the sample with the beam.

The second detection step may comprise detecting the second emissions for the duration time of the third dwell period from the at least one second scan location (of the second data set(s)).

The third dwell period may be higher than the second dwell period for the at least one second scan location.

The third dwell period may be lower than or equal to the second dwell period for the at least one second scan location.

The one-pass classification step may further comprise determining the third dwell period for the at least one second scan location of the second data set(s) based on the calculated confidence score of the respective first spectrum and the intrinsic photon count rate of the corresponding mineral grain.

The one-pass classification step may also comprise adding the number of photons (e.g. X-ray photons) detected with the first detection step to the number of photons (e.g. X-ray photons) detected with the second detection step at the respective second scan location of the second data set(s).

The one-pass classification step may further comprise generating at least one or a plurality of second spectra, wherein each second spectrum may be based on the second emissions detected with the first and the second detection step at the respective second scan location of the second data set(s).

The method may comprise a second spectrum providing step, wherein the second spectrum providing step may comprise providing the second spectra in groups, wherein each group may comprise the second spectra obtained from the at least one or more images.

Each second spectrum may correspond to an X-ray spectrum.

The one-pass classification step may comprise correcting an image generation error for the case that a group may comprise the second spectra obtained from at least two images, wherein the at least two images may show neighboring sections of the sample.

The at least two images may contain at least two parts belonging to one of the mineral grains of low confidence score.

Correcting the image generation error may comprise stitching the at least two parts of the at least two images.

The one-pass classification step may comprise summing the second spectra of the parts belonging to the same mineral grain of low confidence score by means of another merging operator.

The one-pass classification step may comprise a second spectral analysis step.

The one-pass classification step may comprise performing the second spectral analysis step on the second spectra of each group individually.

The second spectral analysis step may comprise matching each second spectrum to at least two known mineral grains based on a result of a second line assignment step.

The second spectral analysis step may comprise calculating at least two or a plurality of new confidence scores for every second spectrum, wherein each new confidence score may correspond to the level agreement between the second spectrum and the corresponding matched reference spectrum.

The one-pass classification step may comprise selecting the highest new confidence score out of the at least two new confidence scores for every second spectrum.

The highest new confidence scores of at least some of the second spectra may correspond to a high confidence score (above or equal to the threshold value).

The one-pass classification step may comprise normalizing the data quality of the mineral grains of (initial) low confidence score.

The one-pass classification step may comprise performing the second detection step and the first spectral analysis step in parallel.

The one-pass classification step may comprise performing the second spectral analysis step after the first spectral analysis step has been essentially performed on the at least one or more images.

The one-pass classification step may comprise performing the second detection step and the second spectral analysis step in parallel.

Moreover, the one-pass classification step may comprise performing the second spectral analysis step on a first group of second spectra relating to first image(s) while in parallel performing the second detection step on second scan locations relating to second image(s).

At least one or more of the mineral grain(s) of low confidence score relating to the second data set(s) may correspond to specific mineral grains.

In particular, at least one of the specific mineral grains may be depicted with the same or a similar intensity (i.e. gray level intensity) on the at least one image of given contrast and brightness values as at least one other specific mineral grain (e.g. $Fe_2O_3$ and $Fe_3O_4$).

Thus, the at least one specific mineral grain may be indistinguishable from the at least one other specific mineral grain on the at least one image.

Further, the part(s) of the selected second scan location(s) relating to the specific mineral grain(s) may correspond to specific part(s) of the corresponding sub-image.

The classification step may further comprise performing the two-pass classification step on the selected second scan location(s) of the second data set(s) relating to the specific part(s).

The two-pass classification step may comprise pre-setting and/or controlling the contrast and brightness values of a corresponding image (e.g. the at least one image or sections thereof) by means of adjusting operational settings of at least one or more system components prior to detecting the corresponding first emissions.

The two-pass classification step may further comprise focusing the beam on the first scan locations within the specific part(s).

Thus, the two-pass classification step may comprise re-detecting the first emissions from the first scan locations of the corresponding specific part(s) upon irradiation of the beam with the sample.

The method may comprise generating and providing at least one or a plurality of new sub-image(s), wherein each new sub-image may be based on the first emissions re-detected at each specific part.

The two-pass classification step may further comprise acquiring the new sub-image(s) with the adjusted contrast and brightness values by pre-adjusting accordingly the operational settings of the at least one system component.

The new image(s) may correspond to the new sub-image(s).

The part(s) delimited by the new image(s) may correspond to the specific part(s) delimited by the new sub-image(s). As mentioned above, each new sub-image may thus contain one of the specific part(s) of the corresponding sub-image.

The two-pass classification step may further comprise revealing and/or detecting at least two or a plurality of new parts within at least one of the new sub-images by means of the adjusted contrast and brightness values of the respective new sub-image.

Each new part may correspond to a section of the specific part within the respective new sub-image.

The two-pass classification step may comprise identifying at least two mineral grains within the at least one new sub-image based on the different intensities (e.g. gray level intensities) between the respective new parts, wherein the at least two mineral grains may be indistinguishable on the at least one image (and sub-image) and wherein one of the mineral grains may correspond to the specific mineral of the specific part.

The two-pass classification step may further comprise performing a second segmentation step on the new sub-images individually for the case of more than one new sub-image being provided.

The second segmentation step may comprise generating a new second scan location for each of the new parts within the at least one new sub-image by means of the k-means clustering algorithm and the flood fill algorithm.

Moreover, the second segmentation step may comprises determining each new second scan location for the duration time of another segmentation period.

The two-pass classification step may comprise generating third data sets, wherein each of the third data sets may comprise a list of the coordinates of the new second scan locations relating to one of the new sub-images.

The method may further comprise providing at least one of the third data sets.

The two-pass classification step may comprise performing another second detection step on the new second scan locations of the at least one third data set.

The other second detection step may comprise focusing the beam on at least one of the new second scan locations of the at least one of the third data sets.

The other second detection step may further comprise detecting the second emissions from the corresponding new second scan locations upon irradiation of the sample with the beam.

Thus, the other second detection step may comprise detecting the second emissions for the duration time of another third dwell period at every new second scan location of the respective third data set.

The two-pass classification step may comprise performing the second segmentation step and the other second detection step in parallel for the case of more than one new sub-image being provided.

Moreover, the two-pass classification step may comprise performing the second segmentation step and the first spectral analysis in parallel.

The two-pass classification step may also comprise performing the other second detection step and the first spectral analysis in parallel The two-pass classification step may further comprise generating at least one or a plurality of new spectra, wherein each new spectrum may be based on the second emissions detected with the other second detection step at the respective new second scan location of the at least one third data set.

In fact, the method may comprise a new spectrum providing step, wherein the new spectrum providing step may comprise providing the new spectra in other groups, wherein each other group may comprise the new spectra obtained from the at least one or more images.

The two-pass classification step may comprise correcting the image generation error as done in the one-pass classification step.

The two-pass classification step may comprise performing another second spectral analysis step on the new spectra of each other group individually.

The other second spectral analysis step may comprise comparing each new spectrum to the reference spectra and calculating at least two or more other new confidence scores as done in the second spectral analysis step of the one-pass classification step.

The two-pass classification step may comprise performing the other second spectral analysis step after the first spectral analysis has been essentially performed on the at least one or more images.

The two-pass classification step may comprise performing the other second detection step and the other second spectral analysis step in parallel.

The two-pass classification step may comprises performing the other second spectral analysis on a first other group of new spectra relating to first image(s) while in parallel performing the second detection step on new second scan locations relating to second image(s).

The two-pass classification step may comprise identifying and classifying the at least two specific mineral grains within the same new sub-image based on a result of the second segmentation step and the other second spectral analysis step.

The third dwell period may be longer than the first dwell period.

The other third dwell period may be longer than the first dwell period.

The other segmentation period may be higher than the other third dwell period. However, the other segmentation period may be lower than or equal to the other third dwell period. As mentioned above, the other segmentation period may depend on the grain size and the image properties.

The method may further comprise a post-processing step.

The post-processing step may comprise acquiring other images from other sections of the sample and/or replicant samples with the localized contrast and brightness values of the at least one of the new sub-images.

The post-processing step may comprise applying a calibration model, wherein the calibration model may comprise relating the chemical composition of the mineral grain(s) (e.g. average atomic number) of the sample to the gray level intensity(-ies) of the corresponding parts on the at least one image.

The calibration model may correspond to a linear regression.

The calibration model may comprise the contrast and the brightness values as model parameters (i.e. fitting parameters).

Moreover, applying the calibration model may comprise using mineral grains of a known chemical composition and their corresponding gray level intensities in the respective other images to calibrate and further constrain the localized contrast and brightness values.

The post-processing step may comprise determining the chemical composition of mineral grain(s) relating to the other sections of the sample and/or the replicant samples by means of their detected gray level intensity(-ies) and the calibrated contrast and brightness values.

At least a part of the one-pass classification step and at least a part of the two-pass classification step are computer implemented.

Further, the pre-processing step, the first segmentation step, the first spectral analysis step and the post-processing step may be computer implemented.

The method may be a method for material analysis and mineralogy.

The sample may comprise a plurality of particles embedded in an epoxy matrix.

The size of each mineral grain may comprise dimensions ranging from at least 1 μm to at most 500 μm.

The scan point may comprise dimensions of at most a micron.

A portion (such as a pixel) of the at least one image may comprise dimensions ranging from at least 10 nm to at most 1000 nm.

The second dwell period may range from at least 1 ms to at most 10 ms.

The one-pass classification step may comprise calculating a high confidence score for at least some or all mineral grains within the sample by detecting on average at least $2 \times 10^3$ photons and at most $3 \times 10^3$ photons per second scan location.

The method may comprise using the system according to any of the system embodiments.

The system may be configured for performing the method according to any of the preceding method embodiments.

In a third embodiment, a computer program product is disclosed.

A computer program product may comprise instructions which, when the program is executed by a computer, cause the computer to carry out the steps of the above-disclosed method.

Another computer program product may comprise instructions which, when the program is executed by the data-processing system (800), cause the data-processing system (800) to perform the steps for which the data-processing system is configured.

For the sake of clarity, some features may only be shown in some figures, and others may be omitted. However, also the omitted features may be present, and the depicted and discussed features do not need to be present in all embodiments.

FIG. 1 shows components of a scanning microscope system 100. The scanning microscope system 100 may be configured for generating a primary beam of charged particles (e.g. electrons or ions). The scanning microscope system may further comprise a scanning electron microscope 101. In this example, the primary beam comprises an electron beam 107. An electron source 102 may be configured for emitting the electron beam, wherein a voltage is applied between the electron source 102 and an anode 103. The applied voltage may preferably range from at least 2 kV to at most 30 kV. The scanning microscope system may also comprise electromagnetic lenses. The electromagnetic lenses may be configured for controlling the path of the electron beam. At least one condensing lens 104 may be comprised by the electromagnetic lenses. The condensing lens 104 may be configured for determining the size of the electron beam. Moreover, at least one objective lens 106 may be comprised by the electromagnetic lenses. The objective lens 106 may be configured for focusing the electron beam to a scan point on the sample. The scan point may correspond to an electron spot on the sample 108. Further, the dimensions and the shape of the scan point may depend on the focusing properties of the electromagnetic lenses (e.g. applied current) and the working distance between the scanning electron microscope 101 and a sample 108. A scanning coil 105 may be configured for deflecting the electron beam 107 over a plurality of scan locations in one or two dimensions. Thus, optionally advantageously, this may enable a two-dimensional scanning of the sample. The scan locations may correspond to first scan locations. The scan locations may also correspond to second scan locations. The scanning coil 105 may be magnetic or electrostatic.

The scanning microscope system can be configured for generating first and second emissions 109, 110. The electron beam 107 may interact with particles (such as atoms) of the sample 108. The interaction may result to the first and the second emissions 109, 110. The first emissions 109 may comprise emissions of charged particles, such as backscattered electrons. However, the first emissions may also comprise emissions of secondary, transmitted and/or Auger electrons. Further, the second emissions 110 may comprise emissions of photons, such as X-rays and/or light (e.g. visible light).

The scanning microscope system 100 may also comprise a first detector 111, wherein the first detector 111 may be configured for detecting the first emissions 109 from the first scan locations in a sequential manner. In particular, the first detector 111, may be configured for detecting the first emissions over a first dwell period at each first scan location.

The first detector 111 may comprise a backscattered electron detector, such as a segmented silicon drift detector. However, the backscattered electron detector may also correspond to other types of solid-state detectors. Moreover, the first detector 111 may also comprise a secondary electron detector, such as an Everhart-Thornley detector, or a transmitted electron detector (e.g. CMOS detector). The transmitted electron detector may be placed below the sample 108 in order to detect transmitted electrons.

Further, the electron microscope system may comprise a second detector 112, wherein the second detector 112 may be configured for detecting the second emissions 110 from the second scan locations in a sequential manner. In particular, the second detector 112, may be configured for detecting the second emissions over a second dwell period at each second scan location. The second detector 112 may comprise an X-ray detector, wherein the X-ray detector may comprise a silicon drift detector. However, the X-ray detector may also comprise other types of detectors (e.g. scintillation detectors). The second detector 112 may be tilted with respect to the surface of the sample 108. The angle between a center line 114 of the second detector and the sample surface may be adjustable and may range from 0° to at most 90°.

The X-ray detector may be comprised by an energy-dispersive spectrometer (EDS). The energy bandwidth of the EDS may range from 0 to at most 17 keV. In another modality the X-ray detector may be comprised by a wavelength-dispersive spectrometer (WDS). Further, the second detector 112 may also be comprised by an electron energy loss spectrometer or a cathodoluminescence spectrometer.

The sample 108 may be positioned on top of a movable stage 113. The movable stage 113 may be configured for performing two horizontal movements, a vertical movement, a tilting movement, and/or a rotational movement, with respect to the plane of the sample. The two horizontal movements may comprise selecting a field of view. The vertical movement may comprise changing the height of the sample and thus the depth of focus and/or the image resolution.

The scanning microscope system 100 may further comprise a control unit 115. The control unit 115 may be configured for controlling the power supply and operation of the condensing lens 104, the objective lens 106, the scanning coil 105 and the movable sage 113. Further, the scanning microscope system may comprise a vacuum system. The vacuum system may comprise a vacuum controller 116, a mechanical pumping system 117, an ultra-high vacuum pump 118 (such as an ion pump) and a vacuum chamber 119. The vacuum controller 116 may be configured for controlling the operation of the mechanical pumping system 117 and the ultra-high vacuum pump 118. The mechanical pumping system 117 and the ultra-high vacuum pump 118 may be configured for providing an ultra-high vacuum within the vacuum chamber 119. The vacuum chamber 119 may be configured for containing the sample 108, the movable stage 113, the first detector 111, the second detector 112 or parts thereof, and the scanning electron microscope 101 or parts thereof.

Figure 2:
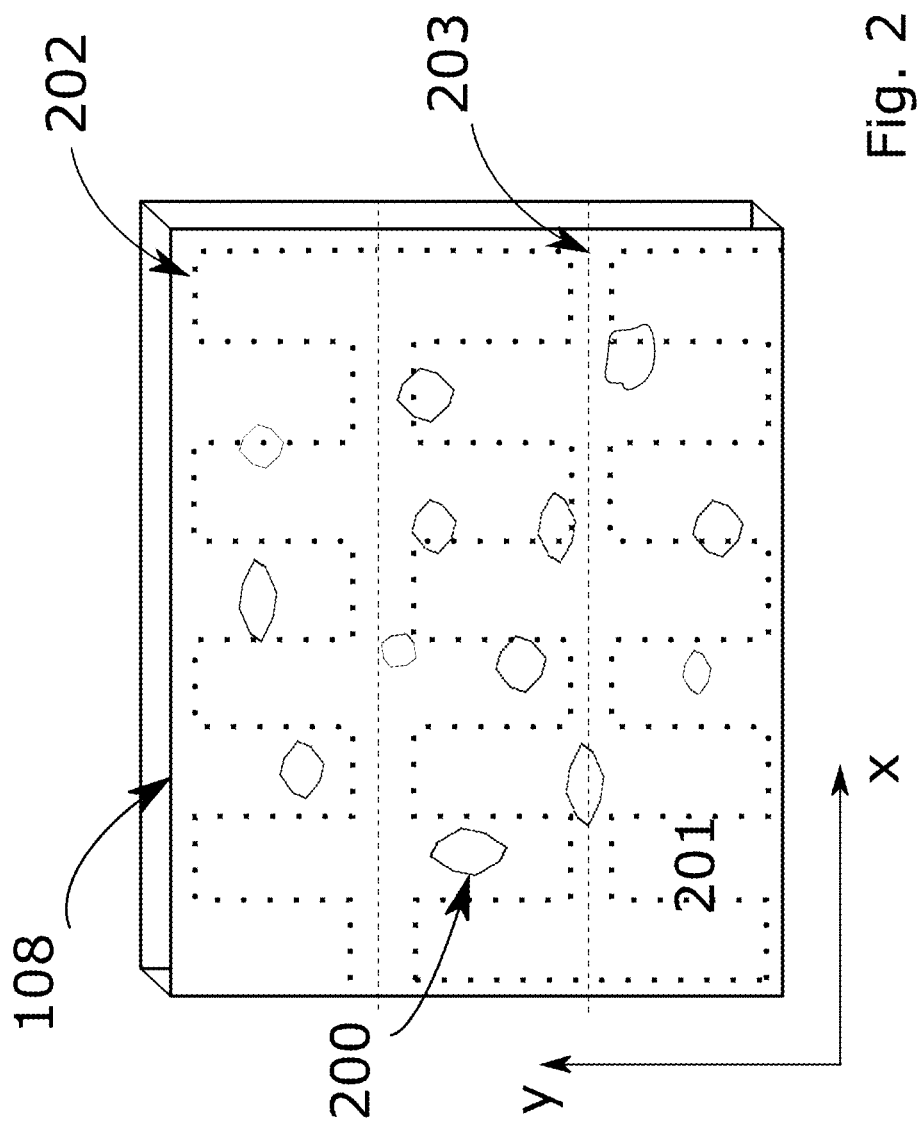
FIG. 2 shows a sample of particles.

FIG. 2 shows the sample 108 containing a plurality of particles 200, wherein each particle may comprise at least one or a plurality of mineral grains. The particles 200 may be embedded in an epoxy matrix 201. An internal two-dimensional coordinate system (x,y) may be assigned to the sample 108. In this example, the origin of the internal coordinate system may be assigned to the lower left corner of the sample. Further, FIG. 2 shows the first scan locations 202. The sequence of the first scan locations may correspond to a scanning pattern. As can be seen in FIG. 2, the scanning pattern may correspond to a second order serpentine pattern. The second order serpentine pattern may comprise a large serpentine pattern that moves back and forth along large rows (dashed lines 203) and a small serpentine pattern that moves up and down within every single row. However, the scanning pattern may also correspond to continuous fractal space- or plane-filling curves, such as Hilbert or Moore curves.

Figure 3:
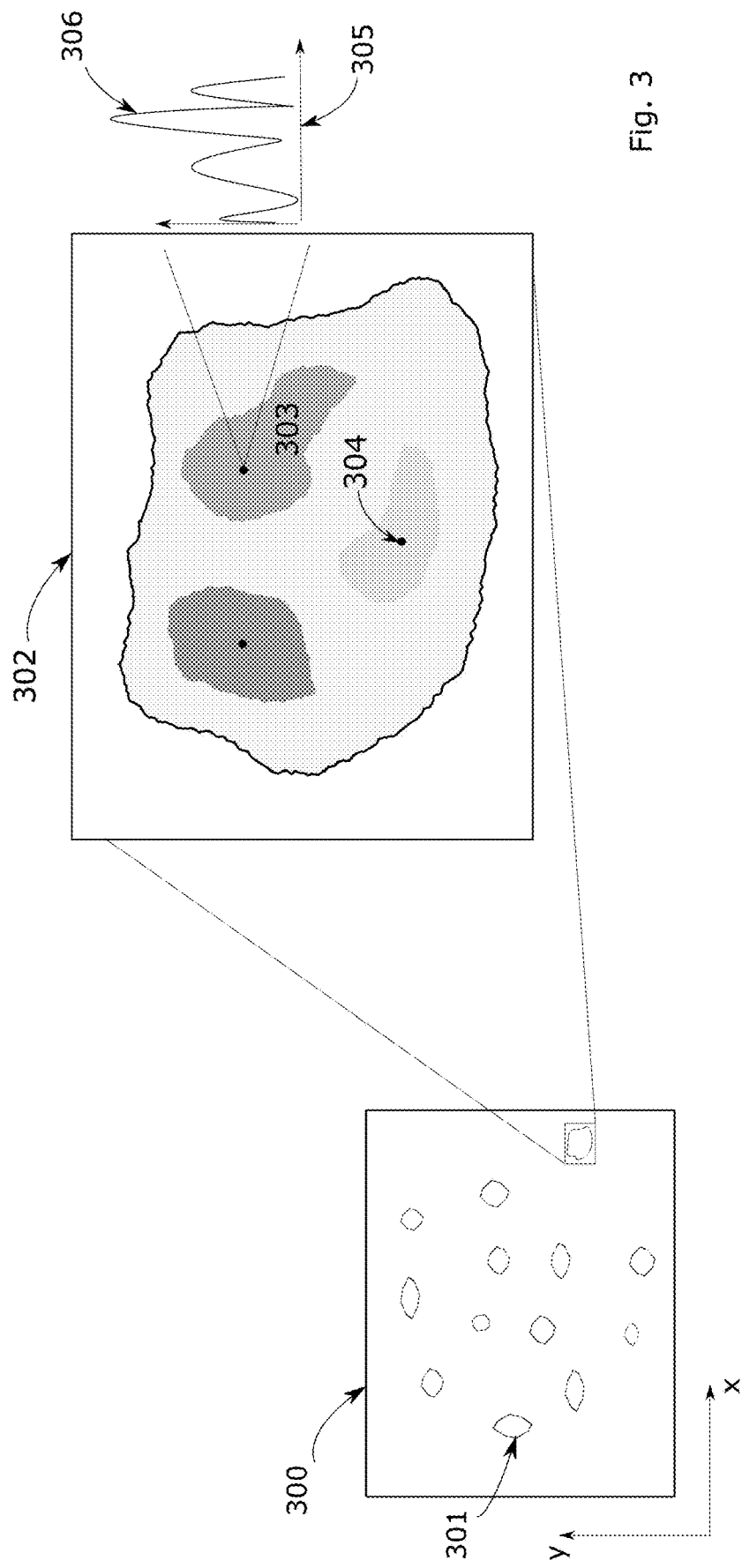
FIG. 3 shows an image of the sample and a sub-image of a poly-mineral particle.

FIG. 3 shows an image 300 of the sample 108. The image may comprise regions 301, wherein each region may correspond to a particle 200 of the sample. The image 300 may be generated based on the first emissions 109 detected at the corresponding first scan locations 202. In this example, the image may be generated based on emissions of backscattered electrons. The image may comprise a two-dimensional grid, wherein each square of the grid corresponds to a portion (such as a pixel). Each portion in the image may correspond to a scan point on the sample. The backscattered electron data may be stored point-by-point in the respective portion of the image. Thus, the intensity of each portion may depend on the number of backscattered electrons detected at the respective scan point. Further, the same internal two-dimensional coordinate system (x,y) of the sample 108, may also be assigned to the image 300. Thus, the location of each portion in the image may be tracked as the electron beam moves across the first scan locations of the sample. Assigning the same coordinate system of the sample to the image may be accomplished by means of reference points of known coordinates, wherein the reference points may be incorporated in the sample 108 or the movable stage 113.

Further, FIG. 3 shows a sub-image 302 comprising a region 301, wherein the sub-image 302 is a section of the image 300. The region 301 of the sub-image 302 may comprise parts 303, wherein each part may correspond to a mineral grain within the corresponding particle 200. Moreover, each part may comprise portions of the same color (e.g. gray) and/or intensity. In other words, the sub-image may show intensity variations between the parts (e.g. mineral grains) with a different chemical composition. The intensity variations may comprise gray level variations. Moreover, the image 300 may comprise a contrast and brightness value.

In the example of FIG. 3, each part 303 comprises a second scan location 304, wherein the second scan location may correspond to a centroid or another estimation of the corresponding part. The first and the second scan locations may be specified with respect to the same two-dimensional coordinate system (x,y).

FIG. 3 further depicts a spectrum 305, wherein the spectrum may be generated based on the second emissions 110 detected at the corresponding second scan location 304. In this example, the spectrum may comprise a graph, wherein the graph depicts the number of detected X-ray photons (i.e. intensity) at the respective energies. As can be seen in FIG. 3, the X-ray spectrum may comprise spectral lines 306 at different energy values. Moreover, the spectral lines 306 may comprise a line width, thus being distributed over a range of energy values rather than being located at a single energy value. Thus, different spectral lines relating to the same and/or different elements may overlap. The peak of each spectral line 306 at the corresponding line center may correspond to the maximum number of detected X-ray photons (i.e. peak intensity) over the corresponding line width. Each spectral line may correspond to an electronic transition of a chemical element (such as silicon, iron, etc.), wherein the energy value of each electronic transition may be unique for the corresponding chemical element. Further, the X-ray spectrum may comprise spectral lines relating to at least one or a plurality of chemical elements (e.g. mineral elements). Thus, optionally advantageously, the spectrum may comprise information about the chemical composition (e.g. mineral composition) of the corresponding second scan locations relating to the mineral grains.

Figure 4:
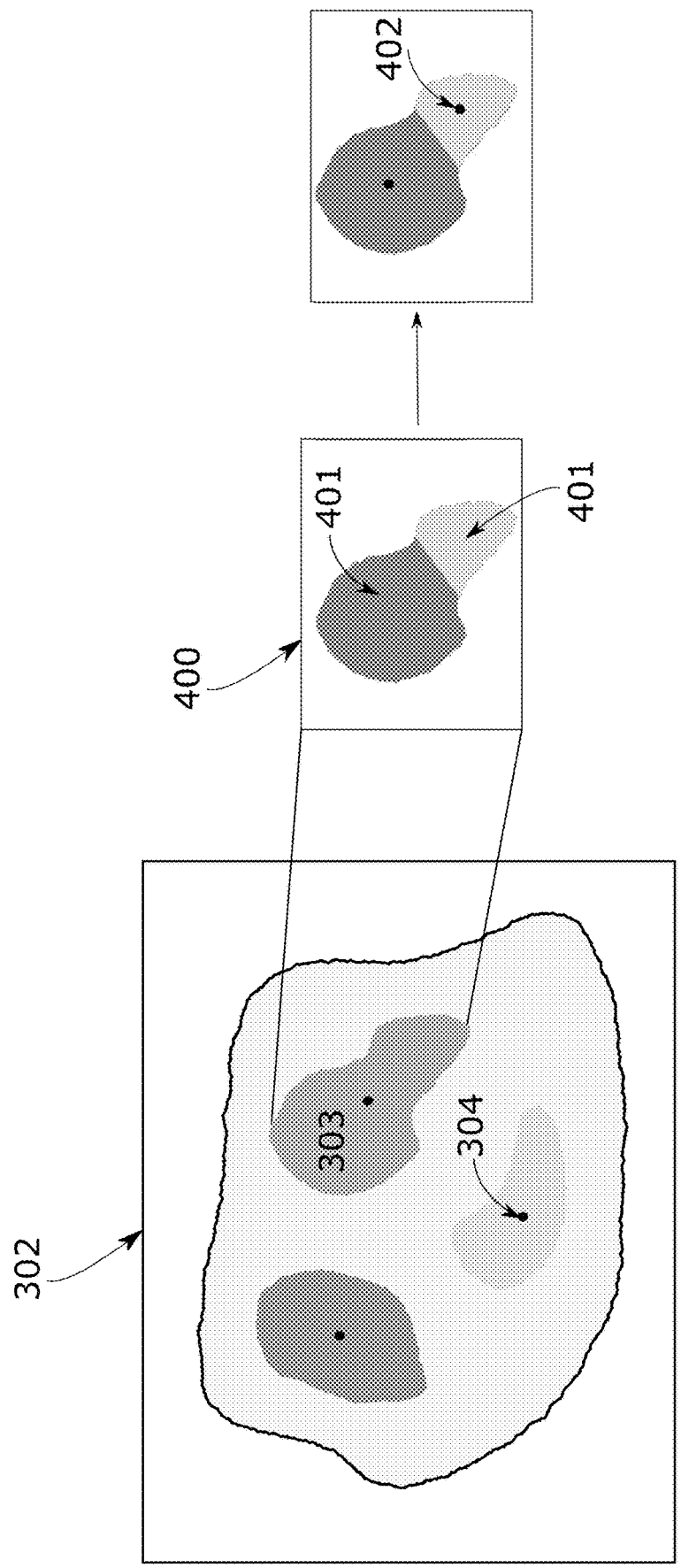
FIG. 4 shows the sub-image of the poly-mineral particle and a new sub-image of a mineral grain with modified contrast and brightness settings.

FIG. 4 shows a new sub-image 400 delimiting one of the parts 303 of the sub-image 302. Thus, the new sub-image comprises a section of the sub-image 302. The delimited part 303 may correspond to a specific part, wherein the specific part may relate to a specific mineral grain (e.g. $Fe_2O_3$). The new sub-image comprises adjusted contrast and brightness values with respect to the sub-image 302, thus revealing two new parts 401. In other words, the two new parts 401 may be sections of the (specific) part 303 comprising different gray level intensities from each other and from part 303. The two new parts 401 may correspond to two mineral grains (e.g. $Fe_2O_3$ and $Fe_3O_4$) with a similar chemical composition. One of the mineral grains may correspond to the specific mineral grain of the specific part (e.g. $Fe_2O_3$). Further, each new part 401 may comprise a new second scan location 402, wherein the new second scan location 402 corresponds to a centroid or another estimation of the new part 401.

Figure 5:
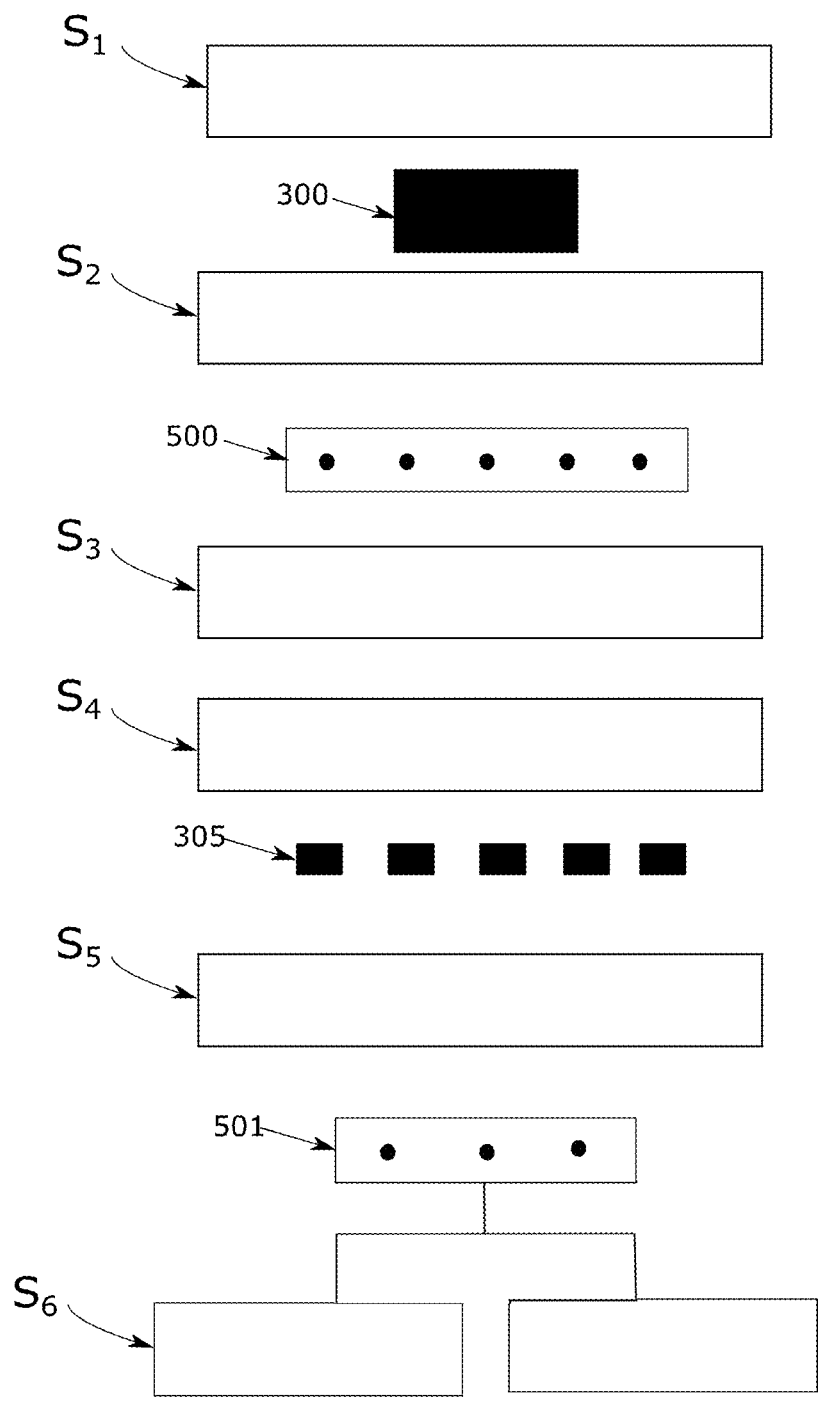
FIG. 5 shows an embodiment of a method.

FIG. 5 shows a method. A system can be configured for performing the method.

The method in FIG. 5 may comprise an image providing step S1, a first segmentation step S2, a first detection step S3, a first spectrum providing step S4, a first spectral analysis step S5 and a classification step S6.

The image providing step S1 may comprise providing at least one image 300 of the sample 108 and/or sections thereof. The at least one image 300 may correspond to a backscattered electron image.

The first segmentation step S2 may comprise generating at least one or a plurality of second scan location(s) for at least one or a plurality of region(s) (see below in description of FIG. 6). Each second scan location may be generated during a segmentation period. The method may further comprise storing the coordinates of the second scan locations in first data sets 500. Each first data set may comprise the coordinates of the second scan location(s) of one of the region(s) of the at least one image. In the example of FIG.

5 the method comprises providing one first data set 500, wherein the one first data set 500 comprises the coordinates of five second scan locations represented by dots. The first detection step S3 may comprise detecting second emissions from the second scan locations 304 of the first data set 500. In particular, the first detection step may comprise scanning the electron beam over the second scan locations 304 and detecting the corresponding second emissions sequentially. In this example, the second emissions comprise emissions of X-ray photons. The integration time at every second scan location may correspond to a second dwell period. The method may further comprise performing the first segmentation step and the first detection step in parallel (for the case of more than one region of the at least one image being processed). Further, the method may comprise storing the detected X-ray photons sequentially for every second scan location. The second dwell period may be four orders of magnitude higher than the first dwell period (see description of FIG. 1). For example, the second dwell period may correspond to 8 ms and the first dwell period may correspond to 1 µs. Thus, the first and the second emissions may be integrated over different dwell periods and detected over different scan locations. Moreover, the first and the seconds emissions may be detected at different times. Thus, the image providing step and the first detection step may take place at different times as well.

The first spectrum providing step S4 may comprise providing at least one or a plurality of first spectra 305, wherein each first spectrum 305 is generated based on the second emissions detected at each of the second scan location(s) 304 of the at least one region 301 (i.e. first data set). In the example of FIG. 5, the first spectrum providing step comprises providing five first spectra 305 (one first spectrum for each second scan location) resulting from second scan locations of the same first data set (i.e region). However, the method may also comprise providing first spectra relating to a plurality of first data sets (i.e. regions). The first spectra 305 may correspond to first X-ray spectra. The first spectral analysis step S5 comprises analyzing each first spectrum 305 sequentially. Analyzing each first spectrum 305 may comprise comparing the respective first spectrum 305 with at least one or a plurality of reference spectra. Each reference spectrum may comprise a plurality of pre-defined spectral lines relating to a known mineral grain. The first spectral analysis step may further comprise a first line assignment step, wherein the first line assignment step may comprise assigning the spectral line(s) of each first spectrum 305 to the pre-defined spectral lines of the reference spectrum(-a). Thus, the first spectral analysis step may comprise matching each first spectrum to one of the known mineral grains based on a result of the first line assignment step.

In fact, the first spectral analysis step comprises calculating a confidence score for each first spectrum, wherein the confidence score corresponds to the level of agreement between the first spectrum and the corresponding matched reference spectrum. The confidence score may comprise a numerical value, ranging from 0 to at most 1. For example, a low confidence score of less than 0.95 may correspond to a partial identification of the chemical composition of the respective mineral grain based on the corresponding first spectrum. A mineral grain of low confidence score has a similar or nearly identical chemical composition with at least another mineral grain. Further, the first spectral analysis step may comprise generating second data sets 501, wherein each second data set 501 may comprise a list of the coordinates of the second scan location(s) relating to the mineral grain(s) of low confidence score. In the example of FIG. 5, the method comprises providing one second data set comprising the coordinates of three second scan locations 304 represented by dots, wherein each second scan location 304 relates to a mineral grain requiring further processing for a reliable classification. The method may further comprise providing the second data set 501 as an input to the classification step S5.

Figure 7A:
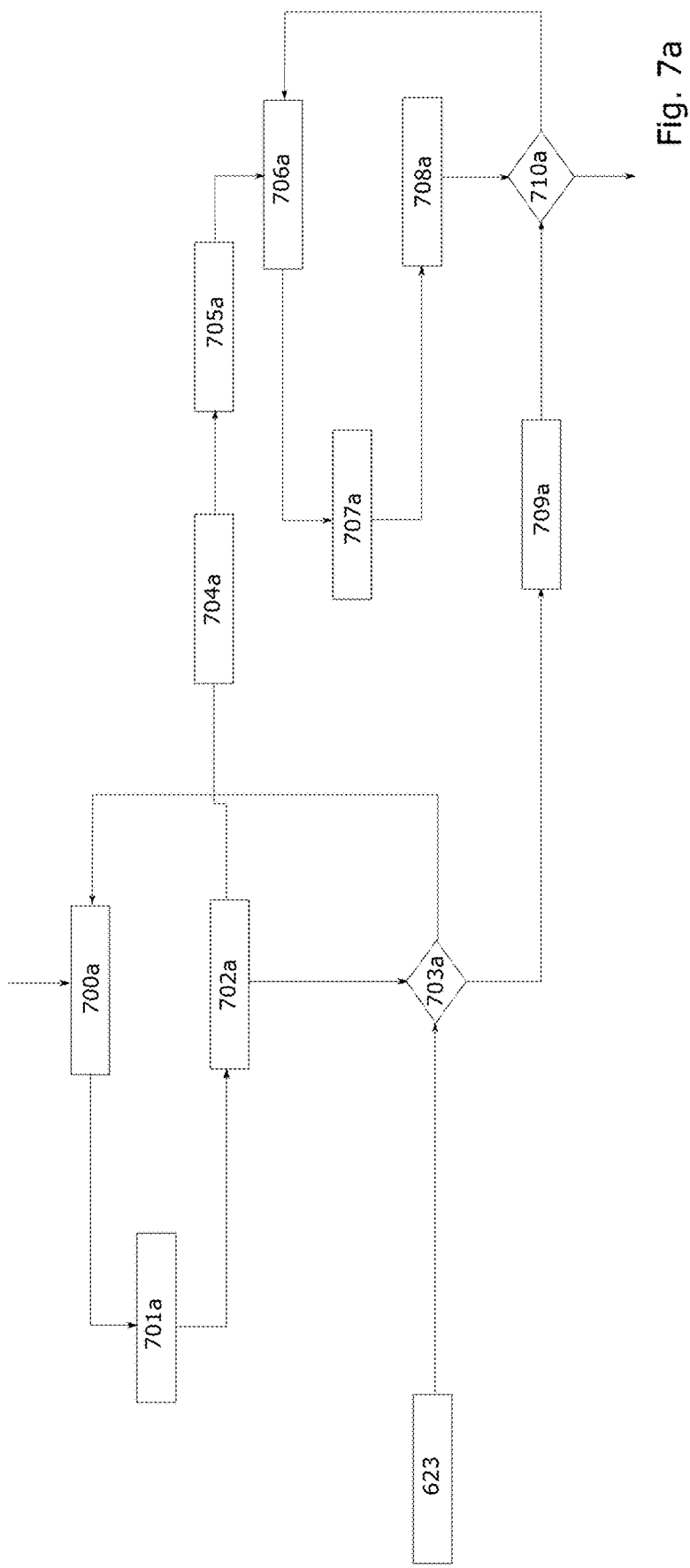
FIG. 7a shows a second flowchart depicting the steps of a one-pass classification process of the embodiment of FIG. 6.
Figure 7B:
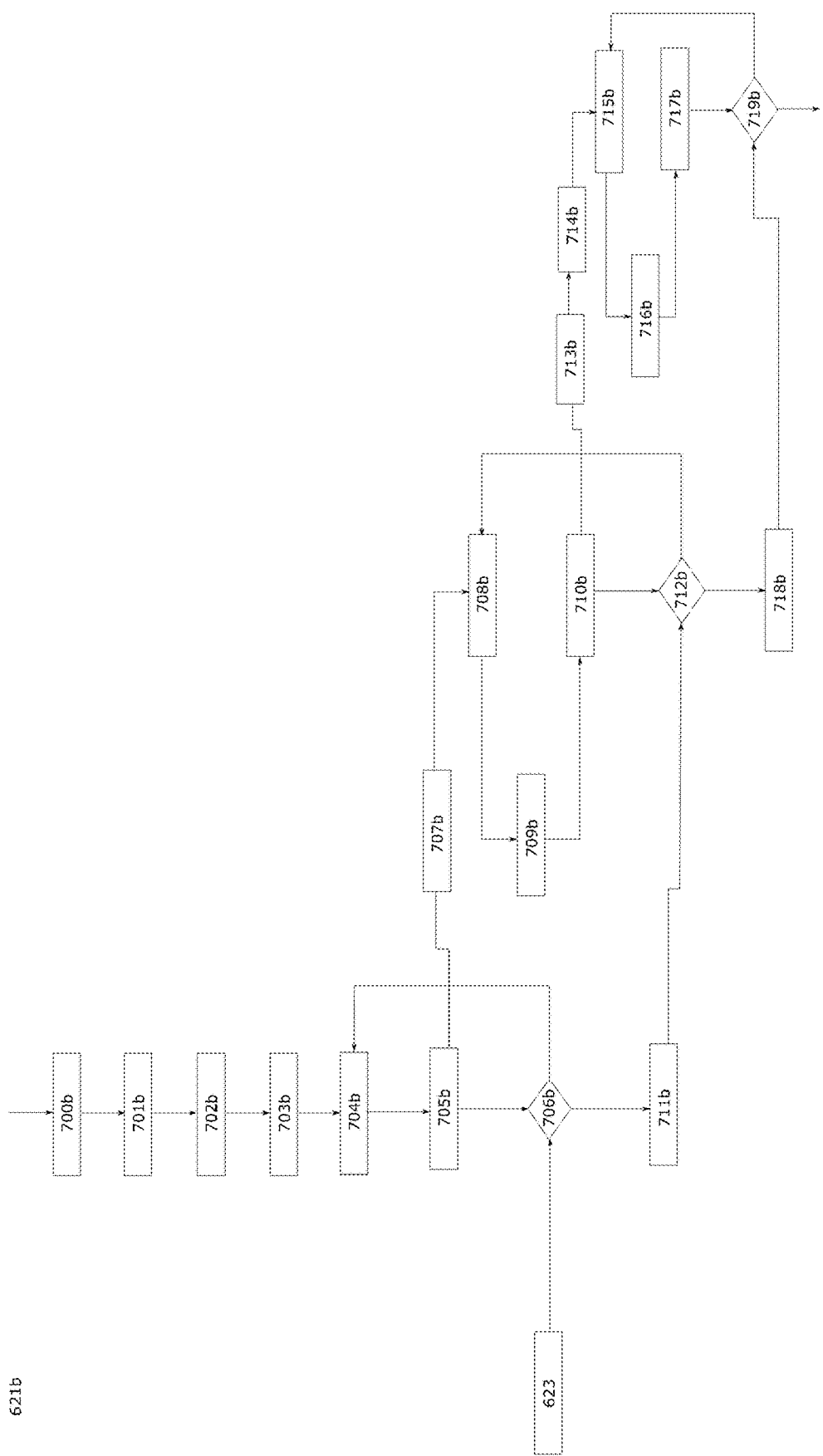
FIG. 7b shows a third flowchart depicting the steps of a two-pass classification process of the embodiment of FIG. 6.

The classification step S5 may comprise a one-pass and/or a two-pass classification step (two individual blocks) based on a result of the first spectral analysis step. The method comprises performing the one-pass classification process on second scan locations relating to mineral grains having a chemical composition similar to at least one or more mineral grains. The one-pass classification step comprises a second detection step, wherein the second detection step comprises detecting the second emissions from the second scan locations of the second data set 501 for the duration time of a third dwell period. The third dwell period may be higher than the second dwell period of the first detection step S3. For example, the third dwell period may correspond to 80 ms and the second dwell period may correspond to 8 ms. The third dwell period may depend on the corresponding calculated confidence score and an intrinsic photon count rate relating to each mineral grain. Thus, the third dwell period may differ from mineral grain to mineral grain. Further, the method comprises performing the two-pass classification process on second scan locations relating to specific mineral grains, wherein at least two of the specific mineral grains may comprise the same or a similar intensity on the at least one image of (such as $Fe_2O_3$ and $Fe_3O_4$). The two-step classification may comprise a second segmentation step and another second detection step. Both classification steps comprise selecting the mineral grains relating to an initially low confidence score and identifying them with a high accuracy (e.g. more than 95%). FIG. 7a and FIG. 7b show in detail the steps comprised by the one-pass and the two-pass classification process, respectively.

Figure 6:
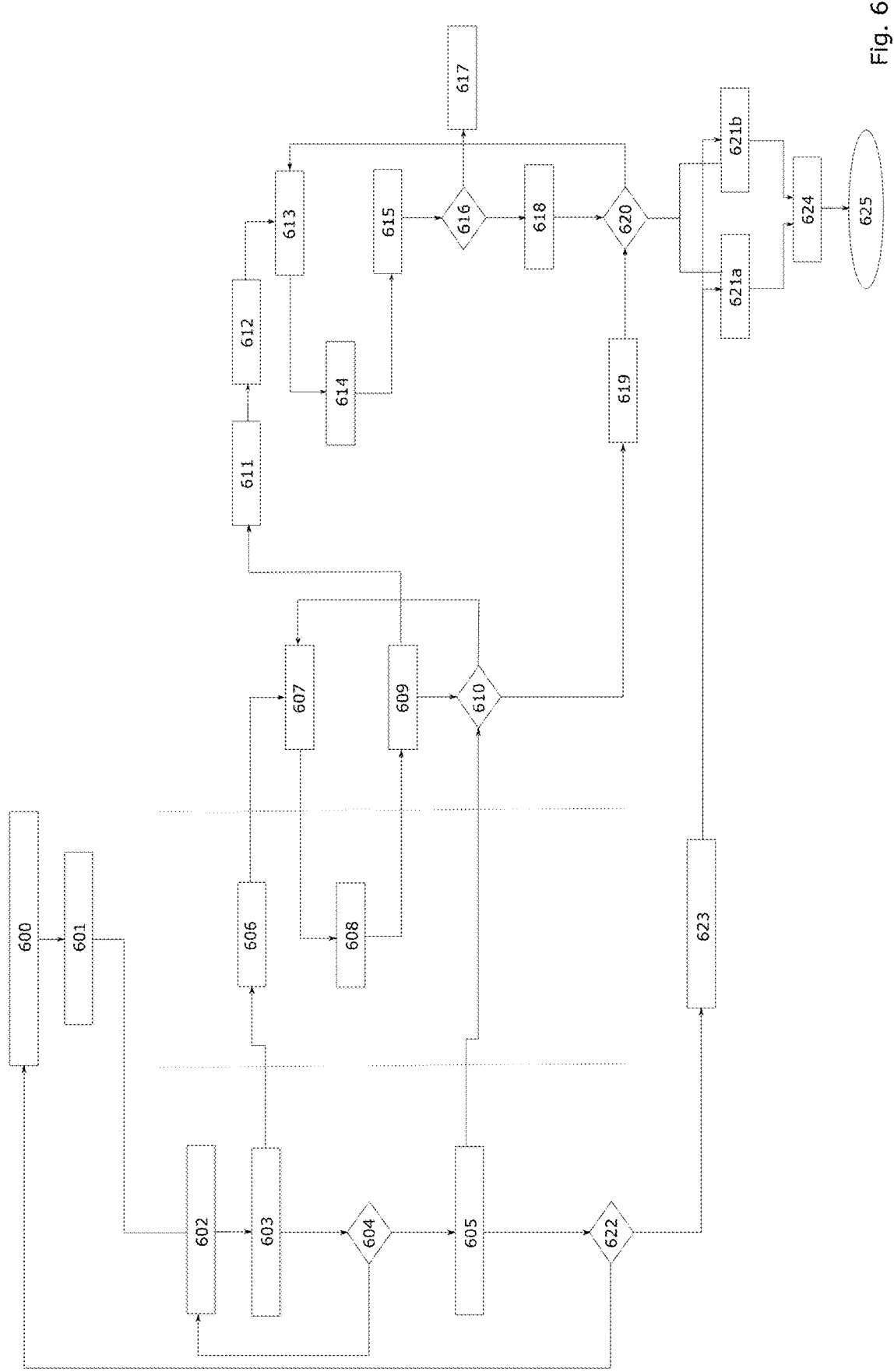
FIG. 6 shows a first flowchart depicting another embodiment of the method.

FIG. 6 shows a first flowchart of an alternative embodiment of the method. A system can be configured for performing the method.

The method may comprise step 600, wherein step 600 comprises generating and providing at least one or a plurality of images, wherein each image corresponds to a backscattered electron image. Further, each image may depict the sample or a section thereof. The method may also comprise step 601, wherein step 601 comprises dividing the at least one image into a plurality of sub-images by means of a contouring algorithm. Each sub-image contains a region 301 of the at least one image, wherein a region 301 corresponds to a particle in the sample. Furthermore, the method may comprise step 602, wherein step 602 comprises selecting and processing one of the sub-images. Processing one of the sub-images comprises identifying parts within the respective region, wherein each part corresponds to a mineral grain of the corresponding particle. The method may also comprise step 603, wherein step 603 may comprise generating one second scan location for each part by means of a k-means clustering algorithm and a flood fill algorithm. Step 603 further comprises generating each second scan location within a segmentation period. The method may further comprise step 606, wherein step 606 comprises storing the coordinates of the second scan locations of the respective sub-image as intermediate results in a first data set. The method may also comprise step 607, wherein step 607 comprises receiving the notification of a first data set being available. The method may then perform step 608, wherein step 608 may comprise receiving the first data set and selecting one or more of the second scan locations of the respective first data set. The method may also comprise step 609, wherein step 609 may comprise detecting the X-ray emissions from the second scan location(s) of the respective first data set sequentially for the duration time of a second dwell period. Furthermore, the method may comprise a decision block 610, wherein the decision block 610 may comprise determining whether or not all the first data sets have been selected for the X-ray acquisition. If not, the method may comprise selecting another first data set in steps 607 and 608. Moreover, the method may also comprise a decision block 604, wherein the decision block may comprise determining whether or not all sub-images of the at least one image have been selected and processed. If not, the method may comprise selecting another sub-image in step 602. If all sub-images have been selected and processed, the method performs step 605, wherein step 605 comprises sending a notification to the decision block 610, wherein the notification comprises marking the end of the segmentation process of the corresponding image. In this case, the decision block 610 determines that the second scan locations from all first data sets have been selected for the X-ray acquisition. The method may also comprise step 611, wherein step 611 may comprise generating first X-ray spectra based on the X-rays detected at each second scan location in step 609. The method further comprises step 612, wherein step 612 comprises storing the first X-ray spectra of the corresponding second scan locations as intermediate results in another data set. The other data set may comprise the first X-ray spectra relating to one or more sub-images (i.e. regions) of the corresponding image. The method may also comprise step 613, wherein step 613 may comprise receiving the notification of the other data set being available. The method may then perform step 614, wherein step 614 may comprise receiving the other data set and selecting one or more of the first X-ray spectra of the respective other data set. The method may also comprise step 615, wherein step 615 may comprise analyzing each first X-ray spectrum sequentially within the respective other data set. The analysis of the first X-ray spectrum may comprise assigning the spectral line(s) of each first X-ray spectrum to pre-defined spectral lines of reference spectrum(-a), wherein each reference spectrum relates to an X-ray spectrum of a known mineral grain. Step 615 may further comprise matching each first spectrum to one of the known mineral grains based on a result of the first line assignment step. Thus, step 615 may comprise calculating a confidence score for each first spectrum, wherein the confidence score corresponds to the level of agreement between the first X-ray spectrum and the corresponding matched reference spectrum. In other words, the confidence score may correspond to an identification accuracy of the chemical composition (e.g. mineral composition) of the respective part of the at least one image.

Furthermore, the method may comprise a decision block 616, wherein the decision block 616 may comprise determining whether or not the corresponding first X-ray spectrum requires further classification based on the confidence score calculated in step 615. If not, the method may comprise step 617, wherein step 617 comprises ending the classification of the corresponding first X-ray spectrum. The method may further comprise step 618, wherein step 618 comprises storing the second scan locations relating to a low confidence score in a second data set. A low confidence score may correspond to an identification accuracy of less than 95%. Moreover, the method may comprise a decision block 620, wherein the decision block 620 may comprise determining whether or not all the other data sets (of the corresponding image) have been selected for the analysis of the first X-ray spectra. If not, the method may comprise selecting an additional other data set in steps 613 and 614. If the decision block 610 determines that the first X-ray acquisition has been performed on the second scan locations of all of the first data sets of the corresponding image, then the method may perform step 619, wherein step 619 may comprise sending a notification to the decision block 620. The decision block 620 may then comprise determining whether to apply step 621*a* or step 621*b*, wherein step 621*a* comprises a one-pass classification process and step 621*b* comprises a two-pass classification process.

A first segmentation step may comprise steps 602, 603 and 604. A first detection step may comprise step 609. Steps 606 and 608 may comprise establishing a balancing queue of second scan locations between the first segmentation step and the first detection step. Moreover, the method may comprise performing the first segmentation step and the first detection step in parallel. Thus, step 609 may run in parallel to steps 602, 603 and 604. Step 615 may be comprised by a first spectral analysis step. The method may also comprise performing the first detection step and the first spectral analysis step in parallel.

The method may also comprise a decision block 622, wherein the decision block may comprise determining whether or not the number of images generated and provided is sufficient. If not, the method may comprise generating and providing another image in step 600. Alternatively, the method may comprise step 623, wherein step 623 may comprise sending a notification to the classification processes 621*a* and/or 621*b*, wherein the notification comprises marking the end of the image generation. Further information on this can be found in the description of FIG. 7*a* and FIG. 7*b*.

The method may also comprise storing the results of the corresponding classification process (step 621*a* or 621*b*) in step 624. The entire process is then terminated in step 625.

FIG. 7*a* shows a second flowchart depicting the steps comprised by the one-pass classification process (620*a*).

The one-pass classification process may comprise step 700*a*, wherein step 700*a* may comprise receiving the notification for the second data set(s) of the image(s) being available for a second X-ray detection. The one-pass classification process also comprises processing the second data set(s) sequentially. The method may then perform step 701*a*, wherein step 701*a* may comprise receiving the second data set(s) and selecting one or more second scan locations of the respective second data set. The method may also comprise step 702*a*, wherein step 702*a* may comprise detecting the X-ray emissions from the second scan location(s) of the corresponding second data set sequentially for the duration time of a third dwell period. The one-pass classification step may further comprise determining the third dwell period based on the confidence score of the respective second scan location determined in the first spectral analysis step (step 614) and based on the intrinsic photon count rate of the respective mineral grain. The third dwell period may be higher than the second dwell period of the first X-ray detection (step 609). For example, the third dwell period may correspond to 80 ms, while the second dwell period may correspond to 8 ms. Thus, step 702*a* may comprise detecting a higher number of X-ray photons within the third dwell period with respect to the second dwell period. Moreover, the one-pass classification step may comprise adding the number of X-ray photons detected with the second X-ray detection (step 702*a*) to the number of X-ray photons detected with the first X-ray detection (step 609) at the respective second scan location of the second data set. Further, the one-pass classification process may comprise a decision block 703a, wherein the decision block 703a may comprise determining whether or not the second scan location(s) of all of the second data sets have been selected and further processed. If not, the method may comprise selecting another second data set in steps 700a and 701a.

The one-pass classification step may also comprise step 704a, wherein step 704a may comprise generating and storing second X-ray spectra of the corresponding selected second scan locations as intermediate results in a new data set (i.e. group of second spectra). In fact, each new data set may comprise the second X-ray spectra corresponding to second scan locations obtained from at least one or a plurality of images. For example, the method may comprise acquiring grids of images, each grid comprising 8×8 images. Each image within the respective grid may depict a section of the sample and thus, a grid of images may depict neighboring sections of the sample. The new data set may then comprise the second X-ray spectra acquired from all images (8×8 images) within the corresponding grid.

For the case of storing the second X-ray spectra obtained from more than one image, the one-pass classification step may further comprise step 705a, wherein step 705a may comprise correcting an image generation error. In particular, the error may comprise generating at least two images of neighboring sections of the sample, wherein the at least two images contain at least two parts belonging to one of the mineral grains of low confidence score. In other words, the corresponding mineral grain is depicted in both images. Thus, step 705a may comprise stitching the parts of the at least two images and merging the respective second X-ray spectra of the parts belonging to the same mineral grain of low confidence score. The one-pass classification step may also comprise step 706a, wherein step 706a comprises receiving the notification of the new data set (i.e. group) being available. The method may then perform step 707a, wherein step 707a may comprise receiving the new data set and selecting one or more second X-ray spectra of the respective new data set.

Further, the one-pass classification step may also comprise step 708a, wherein step 708a may comprise analyzing each second X-ray spectrum of the new data set sequentially. The analysis of the second X-ray spectrum may comprise matching each second X-ray spectrum to at least two known mineral grains based on a result of a second line assignment. Thus, step 708a may comprise calculating at least two or a plurality of new confidence scores and subsequently selecting the highest out of the new confidence scores. The highest new confidence score for every second X-ray spectrum of the new data set may correspond to a high confidence score of ≥95%. In other words, the one-pass classification step may comprise calculating a high identification accuracy for the second spectra and thus normalizing the data quality for the second scan locations relating to mineral grains of (initial) low confidence score. In fact, the one-pass classification process allows to reduce the overall acquisition time since non-ambiguous minerals can be identified with minimal photons, while minerals that are increasingly similar in composition will acquire additional photons, but only enough to resolve the internal ambiguities between that subset. Thus, the one-pass classification step may be faster than conventional classification processes by several factors and by a factor of at least 5, and preferably by a factor of at least 10.

Step 702a may correspond to the second X-ray detection step, while step 708a may be comprised by a second spectral analysis step. Once the first detection step (step 609) is finished, the method comprises starting the second detection step (step 702a) while finishing the first spectral analysis (step 614) on the remaining second scan locations of the other data sets. Thus, the method may comprise performing the second detection step (step 702a) and the first spectral analysis step (step 614) in parallel. Furthermore, the one-pass classification step comprises performing the second spectral analysis step (step 708a) after the first spectral analysis step (step 614) has been fully performed on the at least one or more images (e.g. 8×8 images). The method may also comprise performing the second detection step and the second spectral analysis step in parallel. In other words, the one-pass classification process may comprise performing the second spectral analysis on a first new data set of second spectra relating to a first grid of images (8×8 images) while in parallel performing the second detection step on second scan locations relating to a second grid of images (8×8 images), wherein the images are being processed sequentially. The method may further comprise a decision block 710a, wherein the decision block 710a may determine whether or not the second X-ray spectra of all the new data sets have been selected and analyzed. If not, the method may comprise selecting another new data set in step 706a.

As mentioned above, the method performs step 623, wherein step 623 comprises sending a notification to the decision block 703a, wherein the notification comprises marking the end of the image generation and thus the end of available second data sets. In this case the method comprises step 709a, wherein step 709a comprises sending a notification to the decision block 710a, wherein the notification comprises the end of available second X-ray spectra (i.e. available new data sets).

FIG. 7b shows a third flowchart depicting the steps comprised by the two-pass classification process (620b).

The two-pass classification process may comprise step 700b, wherein step 700b may comprise receiving the second data set(s) of the image(s) as an input for a second segmentation step. The method may then perform step 701b, wherein step 701b may comprise selecting one or more of the second scan locations of each second data set sequentially. The two-pass classification process may further comprise step 702b, wherein step 702b may comprise re-detecting the first emissions from the first scan locations of the (specific) parts 303 relating to the selected second scan locations, sequentially. Furthermore, step 702b may comprise re-acquiring the first emissions with adjusted contrast and brightness values. Each (specific) part 303 (see description of FIG. 4) may correspond to a specific mineral grain (e.g. $Fe_2O_3$), wherein the specific mineral grain may comprise the same or a similar intensity on the image with at least one other specific mineral grain (e.g. $Fe_3O_4$). The method may then perform step 703b, wherein step 703b may comprise providing a new sub-image 400, wherein the new sub-image 400 may contain/delimit the corresponding specific part 303 with the adjusted contrast and brightness values. Furthermore, the two-pass classification process may comprise step 704b, wherein step 704b comprises selecting and processing the corresponding new sub-image. Processing one of the new sub-images comprises identifying new part(s) 401 by means of the increased contrast and brightness values. In fact, each of the new parts 401 may be a section of the initial specific part 303. Thus, the two-pass classification process comprises distinguishing the at least two new parts 401 within the respective new sub-image based on their different intensity (e.g. gray level intensity). The new part(s) 401 may correspond to two mineral grain(s)

(e.g. $Fe_2O_3$ and $Fe_3O_4$), wherein one of the mineral grain(s) may correspond to the initially selected specific mineral grain ($Fe_2O_3$). The method may also comprise step 705b, wherein step 705b may comprise generating one new second scan location within another segmentation period for each new part 401, by means of a k-means clustering algorithm and a flood fill algorithm.

The method may further comprise step 707b, wherein step 707b comprises storing the coordinates of the new second scan location(s) of the respective new sub-image as intermediate results in a third data set. The method may also comprise step 708b, wherein step 708b comprises receiving the notification of the third data set being available for another second detection (i.e. X-ray detection). The method may also comprise step 709b, wherein step 709b may comprise receiving the third data set and selecting one or more of the new second scan location(s) of the respective third data set sequentially. The method may then perform another second X-ray acquisition in step 710b, wherein step 710b may comprise detecting the X-ray emissions from the new second scan location(s) of the respective third data set (again sequentially) and for the duration time of another third dwell period.

Furthermore, the method may comprise a decision block 712b, wherein the decision block 712b may comprise determining whether or not all of the third data sets have been selected for the other second X-ray acquisition. If not, the method may comprise selecting another third data set in steps 708b and 709b. Moreover, the method may also comprise a decision block 706b, wherein the decision block 706b may comprise determining whether or not all of the new sub-images have been selected and processed. If not, the method may comprise selecting another new sub-image in step 704b. As mentioned in the description of FIG. 6, the method comprises step 623, wherein step 623 comprises sending a notification to the decision block 706b, wherein the notification comprises marking the end of the image generation and thus the end of providing new sub-images. Thus, if all available new sub-images have been selected and processed, the method performs step 711b, wherein step 711b comprises sending a notification to the decision block 712b, wherein the notification comprises marking the end of the (second) segmentation process of the new sub-images. In this case, the decision block 712b determines that the new second scan locations from all of the third data sets have been selected for the other second X-ray acquisition. The second segmentation step may comprise steps 704b, 705b and 706b. The other second detection step may comprise step 710b. Steps 707b and 709b may comprise establishing a balancing queue of new second scan locations between the second segmentation step and the other second detection step. Moreover, the two-pass classification process may comprise performing the second segmentation step and the other second detection step in parallel.

Once the first detection step (step 609) is finished, the method comprises starting the second segmentation step while finishing the first spectral analysis step (step 614) on the remaining second scan locations of the other data sets. Thus, the method may comprise performing the second segmentation step and the first spectral analysis step (step 614) in parallel. The method may also comprise performing the other second detection step and the first spectral analysis step (step 614) in parallel (until the first spectral analysis step is completed).

The two-pass classification step may also comprise step 713b, wherein step 713b may comprise generating and storing new X-ray spectra of the corresponding new second scan locations as intermediate results in another new data set (i.e. another group). As mentioned above, each other new data set may comprise the new X-ray spectra corresponding to new second scan locations obtained from at least one or a plurality of images. The two-pass classification step may also comprise step 714b, wherein step 714b may comprise correcting an image generation error (see above in description of FIG. 7a). Moreover, the method may comprise step 715b, wherein step 715b comprises receiving the notification of the other new data set being available. The method may then perform step 716b, wherein step 716b may comprise receiving the other new data set and selecting one or more new X-ray spectra of the respective other new data set (again sequentially).

Further, the two-pass classification step may also perform another second spectral analysis in step 717b, wherein step 717b may comprise analyzing each new X-ray spectrum of the other new data set sequentially. The analysis of the new X-ray spectrum may comprise matching each new X-ray spectrum to at least two known mineral grains based on a result of another second line assignment (as mentioned above). Thus, step 717b may comprise calculating at least two or a plurality of other new confidence scores and subsequently selecting the highest out of the other new confidence scores. The highest new confidence score for every new X-ray spectrum of the new data set may correspond to a high confidence score of ≥95%.

Step 717b may be comprised by another second spectral analysis step. The method may also comprise performing the other second detection step and the other second spectral analysis step in parallel. Furthermore, the two-pass classification step comprises performing the second spectral analysis step (step 717b) after the first spectral analysis step (step 614) has been essentially performed on the at least one or more images (e.g. 8×8 images).

The method may further comprise a decision block 719b, wherein the decision block 719b may determine whether or not all the other new data sets (i.e. other groups) have been selected and analyzed. If not, the method may comprise selecting an additional other new data set in steps 715b and 716b. If the new second scan locations of all third data sets have been selected and processed, the method performs step 718b, wherein step 718b comprises sending a notification to the decision block 719b, wherein the notification comprises marking the end of the other second detection step.

The two-pass classification process comprises identifying the chemical composition of the new parts 401 within each respective new sub-image based on a result of the other second spectral analysis step and the second segmentation step.

Figure 8:
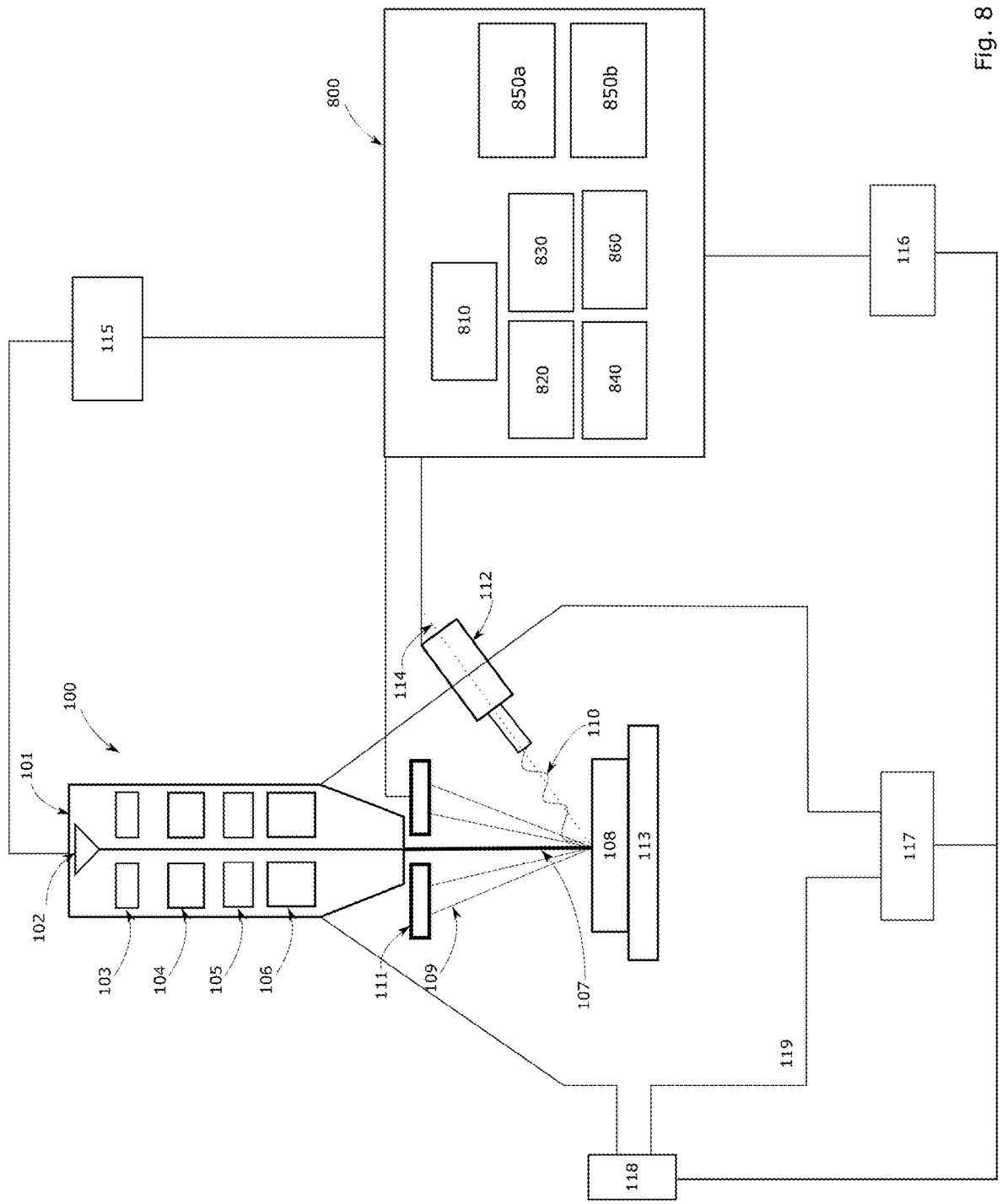
FIG. 8 shows a system configured for performing the method.

FIG. 8 shows a system. The system may be configured for performing the method.

The system comprises the scanning microscope system 100 and a data-processing system 800.

The data-processing system 800 may comprise one or more processing units configured to carry out computer instructions of a program (i.e. machine readable and executable instructions). The processing unit(s) may be singular or plural. For example, the data-processing system 800 may comprise at least one of CPU, GPU, DSP, APU, ASIC, ASIP or FPGA. In this example, the processing unit(s) may be configured for forming the X-ray spectrum based on the detected X-rays. In particular, in case of the EDS modality, the processing unit(s) may be configured for counting and sorting the detected X-rays (at each second scan location) based on the energies of the respective X-rays for the duration of the second dwell period. However, in case of the WDS modality, the processing unit(s) may be configured for counting and sorting the detected X-rays based on the wavelengths of the respective X-rays during the second dwell period.

The data-processing system 800 may comprise memory components, such as the data-storage component 810. The data-storage component 810 as well as the data-processing system 800 may comprise at least one of main memory (e.g. RAM), cache memory (e.g. SRAM) and/or secondary memory (e.g. HDD, SDD).

The data-processing system 800 may comprise volatile and/or non-volatile memory such an SDRAM, DRAM, SRAM, Flash Memory, MRAM, F-RAM, or P-RAM. The data-processing system 800 may comprise internal communication interfaces (e.g. busses) configured to facilitate electronic data exchange between components of the data-processing system 800, such as, the communication between the memory components and the processing components.

The data-processing system 800 may comprise external communication interfaces configured to facilitate electronic data exchange between the data-processing system and devices or networks external to the data-processing system. In the example of FIG. 8, the external communication interfaces may be configured for facilitating an electronic connection between the processing components of the data-processing system 800 and components of the scanning microscope system 100, such as the control unit 115. Moreover, the external communication interfaces may be configured for establishing an electronic data exchange between the processing components of the data-processing system 800 and the vacuum controller 116.

Furthermore, the external communication interfaces may also be configured for establishing an electronic data exchange between the data-processing system 800 and the first detector 111. The external communication interfaces may also be configured for facilitating an electronic connection between the data-processing system 800 and the second detector 112. For example, the detected backscattered electron data from every first scan location may be stored in the data-storage component 810. The processing unit(s) of the data-processing system 800 may be configured for forming the at least one image based on the stored backscattered electron data.

The backscattered electron image of the sample and the X-ray spectrum from each second scan location may be stored in the data-storage component 810.

The data-processing system may also comprise network interface card(s) that may be configured to connect the data-processing system to a network, such as, to the Internet. The data-processing system may be configured to transfer electronic data using a standardized communication protocol. The data-processing system may be a centralized or distributed computing system.

The data-processing system may comprise user interfaces, such as an output user interface and/or an input user interface. For example, the output user interface may comprise screens and/or monitors configured to display visual data (e.g. a backscattered electron image of the sample or an X-ray spectrum) or speakers configured to communicate audio data (e.g. playing audio data to the user). The input user interface may e.g. a keyboard configured to allow the insertion of text and/or other keyboard commands (e.g. allowing the user to enter instructions to the scanning microscope system or parameters for the method) and/or a trackpad, mouse, touchscreen and/or joystick, e.g. configured for navigating the backscattered electron image or regions identified in the backscattered electron image.

To put it simply, the data-processing system 800 may be a processing unit configured to carry out instructions of a program. The data-processing system 800 may be a system-on-chip comprising processing units, memory components and busses. The data-processing system 800 may be a personal computer, a laptop, a pocket computer, a smartphone, a tablet computer. The data-processing system may comprise a server, a server system, a portion of a cloud computing system or a system emulating a server, such as a server system with an appropriate software for running a virtual machine. The data-processing system may be a processing unit or a system-on-chip that may be interfaced with a personal computer, a laptop, a pocket computer, a smartphone, a tablet computer and/or user interfaces (such as the upper-mentioned user interfaces).

In the example of FIG. 8, the data-processing system comprises a one-pass classification component 860a configured for performing at least a part of the one-pass classification step. The data-processing system further comprises a two-pass classification component 860b configured for performing at least a part of the two-pass classification step.

In other words, the data-processing system 800 may comprise a one-pass and a two-pass classification component 850a and 850b, respectively. More particularly, the data-processing system 800 may comprise at least one storage device wherein the data-processing system 800 may be stored.

At least one of the two classification components 850a and 850b may be implemented in software. Thus, at least one of the classification components 850a and 850b may be a software component, or at least a portion of one or more software components. The data-processing system 800 may be configured for running said software component, and/or for running a software comprising this software component. In other words, at least one of the classification components 850a and 850b may comprise one or more computer instructions (i.e. machine-readable instructions) which may be executed by a computer (e.g. the data-processing system 800).

The one-pass and/or the two-pass classification component 850a and 850b may be stored on one or more different storage devices. For example, the classification components 850a and 850b may be stored on a plurality of storage components comprising persistent memory, for example a plurality of storage devices in a RAID-system, or different types of memory, such as persistent memory (e.g. HDD, SDD, flash memory) and main memory (e.g. RAM).

At least one of the classification components 850a and 850b may also be implemented at least partially in hardware. For example, the classification components 850a and 850b or at least a portion of at least one of the classifications components 850a and 850b may be implemented as a programmed and/or customized processing unit, hardware accelerator, or a system-on-chip that may be interfaced with the data-processing system 800, a personal computer, a laptop, a pocket computer, a smartphone, a tablet computer and/or a server.

At least one of the classification components 850a and 850b may also comprise elements implemented in hardware and elements implemented in software. An example may be a use of a hardware-implemented encryption/decryption unit and a software implemented processing of the decrypted data.

Also, the data-processing system 800 may comprise a first segmentation component 820. The first segmentation component 820 may be configured for performing the first segmentation step. More particularly, the data-processing system 800 may comprise at least one storage device wherein the first segmentation component 820 may be stored.

The data-processing system 800 may also comprise a pre-processing component 830. The pre-processing component 830 may be configured for performing the pre-processing step.

The data-processing system 800 may also comprise a first spectral analysis component 840. The first spectral analysis component 840 may be configured for performing the first spectral analysis step.

Further, the data-processing system 800 may also comprise a post-processing component 860. The post-processing component 860 may be configured for performing the post-processing step.

The data-processing system 800 may comprise at least one storage device wherein at least one of, the first segmentation component 820, the pre-processing component 830, the first spectral analysis component 840 and the post-processing component 860 may be stored, such as the data-storage component 810.

At least one of the first segmentation component 820, the pre-processing component 830, the first spectral analysis component 840 and the post-processing component 860 may be implemented in software. One, some or all of these components may be a software component, or at least a portion of one or more software components. The data-processing system 800 may be configured for running said software components, and/or for running a software comprising the software components. In other words, the components may comprise one or more computer instructions (i.e. machine-readable instructions) which may be executed by a computer (e.g. the data-processing system 800).

At least one of the first segmentation component 820, the pre-processing component 830, the first spectral analysis component 840 and the post-processing component 860 may be stored on one or more different storage devices. For example, the at least one of the components may be stored on a plurality of storage components comprising persistent memory, for example a plurality of storage devices in a RAID-system, or different types of memory, such as persistent memory (e.g. HDD, SDD, flash memory) and main memory (e.g. RAM).

The components may also be implemented at least partially in hardware. For example, at least one of the first segmentation component 820, the pre-processing component 830, the first spectral analysis component 840 and the post-processing component 860 or at a part of one of their functionalities may be implemented as a programmed and/or customized processing unit, hardware accelerator, or a system-on-chip that may be interfaced with the data-processing system 800, a personal computer, a laptop, a pocket computer, a smartphone, a tablet computer and/or a server.

While in the above, a preferred embodiment has been described with reference to the accompanying drawings, the skilled person will understand that this embodiment was provided for illustrative purpose only and should by no means be construed to limit the scope of the present invention, which is defined by the claims.

Whenever a relative term, such as "about", "substantially" or "approximately" is used in this specification, such a term should also be construed to also include the exact term. That is, e.g., "substantially straight" should be construed to also include "(exactly) straight".

Whenever steps were recited in the above or also in the appended claims, it should be noted that the order in which the steps are recited in this text may be accidental. That is, unless otherwise specified or unless clear to the skilled person, the order in which steps are recited may be accidental. That is, when the present document states, e.g., that a method comprises steps (A) and (B), this does not necessarily mean that step (A) precedes step (B), but it is also possible that step (A) is performed (at least partly) simultaneously with step (B) or that step (B) precedes step (A). Furthermore, when a step (X) is said to precede another step (Z), this does not imply that there is no step between steps (X) and (Z). That is, step (X) preceding step (Z) encompasses the situation that step (X) is performed directly before step (Z), but also the situation that (X) is performed before one or more steps (Y1), . . . , followed by step (Z). Corresponding considerations apply when terms like "after" or "before" are used.

The following embodiments also form part of the invention.

System Embodiments

Below, embodiments of a system will be discussed. The system embodiments are abbreviated by the letter "S" followed by a number. Whenever reference is herein made to the "system embodiments", these embodiments are meant.

S1. A system comprising a scanning microscope system (100) and a data-processing system (800), wherein the system is configured for
- providing at least one or a plurality of images of the sample or sections thereof based on first emissions detected within a first dwell period from a plurality of first scan locations;
- detecting second emissions for a second dwell period from at least one or a plurality of second scan locations of at least one region of the at least one image, each second scan location relating to a part of the corresponding region;
- providing at least one or a plurality of first spectra, wherein each first spectrum is based on the second emissions detected at each of the second scan location(s) of the at least one region;
- calculating a confidence score for every first spectrum and selecting the second scan location(s) relating to the first spectrum(-a) with confidence score(s) below a threshold value;
- detecting the second emissions for a third dwell period from at least one of the selected second scan location(s) and/or providing at least one or a plurality of new image(s) delimiting part(s) relating to the selected second scan location(s) and determining new second scan locations within the respective new image(s) through modified contrast and brightness values thereof with respect to the at least one image.

S2. The system according to the preceding embodiment, wherein the scanning microscope system (100) comprises a first detector (111), wherein the first detector is configured for detecting the first emissions from the first scan locations.

S3. The system according to the preceding embodiment, wherein the first detector comprises a backscattered electron detector.

S4. The system according to any of the preceding embodiments, wherein the scanning microscope system (100) comprises a second detector (112), wherein the second detector is configured for detecting the second emissions from the second scan location(s) and the new second scan locations.

S5. The system according to the preceding embodiment, wherein the second detector comprises an X-ray detector.

S6. The system according to any of the preceding embodiments, wherein the system, particularly the scanning microscope system (100), is configured for focusing a beam of charged particles (such as electrons) to a scan point on the sample.
S7. The system according to any of the preceding embodiments, wherein the system, particularly the scanning microscope system (100), is further configured for scanning the beam of charged particles over a plurality of scan locations in one or two dimensions.
S8. The system according to any of the preceding embodiments, wherein the scan locations correspond to the first scan locations.
S9. The system according to any of the preceding embodiments, wherein the scan locations correspond to the second scan locations.
S10. The system according to any of the preceding embodiments, wherein the system, in particular the data-processing system (800), is further configured for assigning a two-dimensional coordinate system to the sample.
S11. The system according to any of the preceding embodiments and with the features of S10, wherein the system, particularly the data-processing system (800), is configured for assigning the two-dimensional coordinate system of the sample to the at least one image.
S12. The system according to any of the preceding embodiments and with the features of S7, wherein a result of scanning the beam of charged particles over the scan locations of the sample comprises an interaction of the beam with the sample.
S13. The system according to the preceding embodiment and with the features of S1, wherein a result of the interaction comprises the first and/or the second emissions.
S14. The system according to the preceding embodiment and with the features of S1 and S13, wherein the first emissions comprise emissions of particles (such as backscattered electrons).
S15. The system according to the preceding embodiment and with the features of S1 and S13, wherein the second emissions comprise emissions of photons (such as X-ray photons).
S16. The system according to any of the preceding embodiments, wherein the system, particularly the data-processing system (800), is configured for generating the at least one image based on the first emissions detected at each first scan location.
S17. The system according to any of the preceding embodiments, wherein the at least one image corresponds to a backscattered electron image.
S18. The system according to any of the preceding embodiments, wherein the at least one image shows intensity variations between the regions (and/or parts thereof) with different properties (such as chemical composition).
S19. The system according to the preceding embodiment, wherein the intensity variations comprise gray level variations.
S20. The system according to any of the preceding embodiments, wherein the at least one image comprises a contrast and a brightness value.
S21. The system according to any of the preceding embodiments, wherein each region of the at least one image corresponds to a particle in the sample.
S22. The system according to the preceding embodiment, wherein each particle in the sample comprises at least one or a plurality of mineral grain(s).
S23. The system according to any of the preceding embodiments, wherein the scanning microscope system (100), particularly the first detector (111), is configured for detecting the first emissions for the duration time of the first dwell period at each first scan location.
S24. The system according to any of the preceding embodiments, wherein the scanning microscope system (100), particularly the second detector (112), is configured for detecting the second emissions for the duration time of the second dwell period at each second scan location.
S25. The system according to any of the two preceding embodiments and with the features of S1, wherein the second dwell period is longer than the first dwell period.
S26. The system according to any of the preceding embodiments, wherein the system is configured for detecting the first emissions from the first scan locations and detecting the second emissions from the second scan location(s) at different time intervals, wherein the different time intervals correspond to non-overlapping time intervals.
S27. The system according to the preceding embodiment, wherein the data-processing system (800) comprises a data-storage component (810).
S28. The system according to the preceding embodiment, wherein the data-storage component (810) is configured for providing the at least one image of the sample (or sections thereof).
S29. The system according to any of the preceding embodiments, wherein the data-processing system (800) comprises a first segmentation component (820), wherein the first segmentation component (820) is configured for determining the second scan location(s) of the region(s) of the at least one image.
S30. The system according to any of the preceding embodiments, wherein the data-processing system, particularly the first segmentation component (820), is configured for determining each second scan location for the duration time of a segmentation period.
S31. The system according to any of the preceding embodiments, wherein the segmentation period is longer than the second dwell period.
S32. The system according to any of the preceding embodiments, wherein the segmentation period is shorter than or equal to the second dwell period.
S33. The system according to any of the preceding embodiments, wherein the segmentation period depends on image properties, such as the resolution and the magnification of the at least one image (and/or the sections thereof).
S34. The system according to any of the preceding embodiments, wherein the segmentation period depends on the size of the mineral grain(s) and/or particle(s).
S35. The system according to any of the preceding method embodiments, wherein the data-processing system comprises a pre-processing component (830).
S36. The system according to the preceding embodiment, wherein the data-processing system (800), particularly the pre-processing component (830), is configured for applying a thresholding algorithm.
S37. The system according to the preceding embodiment, wherein the pre-processing component (830), particularly the thresholding algorithm, is configured for separating the at least one image into a background part and a foreground part based on a threshold intensity.
S38. The system according to any of the preceding embodiments, wherein the background part comprises background portions, wherein the background portions (e.g. pixels) comprise intensities lower than the threshold intensity (e.g. dark gray and/or black portions).
S39. The system according to any of the preceding embodiments, wherein the foreground part comprises foreground portions, wherein the foreground portions (e.g. pixels) comprise intensities higher than or equal to the threshold intensity (e.g. bright gray and/or white portions).

S40. The system according to the preceding embodiment, wherein delimiting/removing the background part comprises assigning to the background portions the same value of color and/or intensity (e.g. black portions).

S41. The system according to any of the preceding embodiments, wherein the foreground part comprises at least some of the regions of the image.

S42. The system according to any of the preceding embodiments, wherein the data-processing system (800), particularly the pre-processing component (830), is configured for determining the boundaries of the corresponding regions of the at least one image by means of a contouring algorithm.

S43. The system according to any of the preceding embodiments, wherein the pre-processing component (830), particularly the contouring algorithm, is configured for joining adjacent portions along the boundaries of the corresponding regions to curves.

S44. The system according to the preceding embodiment, wherein the adjacent portions along the boundaries of the corresponding regions are surrounded by the background portions (e.g. black portions).

S45. The system according to any of the preceding embodiments, wherein the data-processing system (800), particularly the pre-processing component (830), is further configured for applying a bounding box algorithm.

S46. The system according to the preceding embodiment, wherein the pre-processing component (830), particularly the bounding box algorithm, is configured for dividing the at least one image into at least one or a plurality of sub-images based on a result of the contouring algorithm.

S47. The system according to any of the preceding embodiments and with the features of S46, wherein a sub-image of the at least one image is delimiting one region.

S48. The system according to any of the preceding embodiments and with the features of S46, wherein the data-processing system (800), particularly the data-storage component (810), is configured for providing the sub-image(s).

S49. The system according to any of the preceding embodiments, wherein the data-processing system (800), particularly the first segmentation component (820), is configured for correcting a sub-image generation error.

S50. The system according to the preceding embodiment, wherein the sub-image generation error comprises generating at least one sub-image containing at least two neighboring regions.

S51. The system according to the preceding embodiment, wherein the at least two neighboring regions located within the one sub-image correspond to touching particles in the sample.

S52. The system according to the preceding embodiment, wherein at least one or more portions along the boundary of one of the neighboring regions are contiguous with at least one or more portions along the boundary of another of the neighboring regions.

S53. The system according to any of the preceding embodiments and with the features of S49, wherein correcting the sub-image generation error comprises processing each of the neighboring regions within the one sub-image individually.

S54. The system according to any of the preceding embodiments and with the features of S46, wherein the data-processing system (800), particularly the first segmentation component (820), is configured for processing the sub-images individually for the case of more than one sub-image being provided.

S55. The system according to any of the preceding embodiments, wherein the data-processing system (800), particularly the first segmentation component (820), is configured for determining the second scan location(s) for the sub-image(s).

S56. The system according to any of the preceding embodiments, wherein the data-processing system (800), particularly the first segmentation component (820), is configured for assigning contiguous portions of the parts of the corresponding regions within the respective sub-images to clusters by means of a k-means clustering algorithm.

S57. The system according to any of the two preceding embodiments, wherein each region of the respective sub-image comprises at least one or a plurality of clusters.

S58. The system according to any of the preceding embodiments and with features of S56, wherein the data-processing system (800), particularly the first segmentation component (820), is further configured for applying a flood fill algorithm, wherein the flood fill algorithm is configured for generating a mask for at least one of the clusters.

S59. The system according to the preceding embodiment, wherein generating the mask for the at least one of the clusters comprises assigning to contiguous portions within the corresponding cluster the same value of color and/or intensity.

S60. The system according to any of the preceding embodiments, wherein each mask is delimiting a part of the corresponding region.

S61. The system according to the preceding embodiment, wherein a part within each region of the at least one image corresponds to a mineral grain within the corresponding particle in the sample.

S62. The system according to any of the preceding embodiments, wherein the data-processing system (800), particularly the first segmentation component (820), is configured for determining one second scan location for each mask.

S63. The system according to the preceding embodiment, wherein each second scan location corresponds to a centroid of the respective mask.

S64. The system according to any of the preceding embodiments, wherein the data-processing system (800), particularly the first segmentation component (820), is further configured for correcting an over-segmentation error.

S65. The system according to the preceding embodiment, wherein the over-segmentation error comprises determining more than one second scan location for at least one of the masks.

S66. The system according to any of the two preceding embodiments, wherein the data-processing system (800), particularly the first segmentation component (820), is configured for merging the second scan locations for the at least one of the masks into one second scan location by means of a merging operator.

S67. The system according to any of the preceding embodiments, wherein the system, particularly the data-processing system (800), is configured for generating first data set(s) for the region(s) within the respective sub-image(s).

S68. The system according to the preceding embodiment, wherein a first data set comprises a list of the coordinates of the second scan location(s) relating to one of the regions.

S69. The system according to any of the preceding embodiments, wherein the data-processing system (800), particularly the data-storage component (810), is configured for providing at least one of the first data sets.

S70. The system according to any of the preceding embodiments, wherein the system, particularly the scanning microscope system (100), is configured for focusing the beam on at least one of the second scan locations of the at least one of the first data sets.

S71. The system according to any of the preceding embodiments, wherein the scanning microscope system (100), particularly the second detector (112), is configured for detecting the second emissions from the corresponding second scan location(s) of the first data set(s) upon irradiation of the sample with the beam.

S72. The system according to any of the preceding embodiments, wherein the system is further configured for determining the second scan location(s) of the sub-images and detecting the second emissions from the at least one of the second scan locations of the first data sets in parallel for the case of more than one sub-image (i.e. first data set) being provided.

S73. The system according to any of the preceding embodiments and with the features of S1, wherein the system, particularly the data-processing system (800), is configured for generating the first spectrum(-a) based on the second emissions (i.e. number of photons) detected at each of the second scan location(s) of the at least one sub-image (i.e. first data set).

S74. The system according to any of the preceding embodiments, wherein the data-processing system (800), particularly the data-storage component (810), is configured for providing the first spectrum(-a).

S75. The system according to any of the preceding embodiments, wherein each first spectrum corresponds to an X-ray spectrum.

S76. The system according to the preceding embodiment, wherein the X-ray spectrum comprises at least one or a plurality of spectral lines.

S77. The system according to any of the preceding embodiments and with the features of S75 and S76, wherein the X-ray spectrum comprises the number of detected X-ray photons (i.e. spectral line intensity) at the respective energies.

S78. The system according to the preceding embodiment, wherein each spectral line corresponds to an electronic transition of a chemical element.

S79. The system according to any of the preceding embodiments, wherein each mineral grain of the sample comprises at least one or a plurality of chemical elements.

S80. The system according to any of the preceding embodiments, wherein the X-ray spectrum comprises information about the chemical composition (e.g. mineral composition) of the corresponding mineral grain relating to the respective second scan location.

S81. The system according to any of the preceding embodiments, wherein the data-processing system (800) further comprises a first spectral analysis component (840).

S82. The system according to any of the preceding embodiments, wherein the data-processing system (800), particularly the first spectral analysis component (840), is configured for analyzing each first spectrum from the respective second scan location of the at least one of the regions (i.e. first data sets).

S83. The system according to the preceding embodiment, wherein analyzing each first spectrum comprises comparing the respective first spectrum with at least one or a plurality of reference spectra.

S84. The system according to the preceding embodiment, wherein each reference spectrum comprises a plurality of pre-defined spectral lines relating to a known mineral grain.

S85. The system according to any of the preceding embodiments, wherein the first spectral analysis component comprises a first line assignment component, wherein the first line assignment component is configured for assigning the spectral line(s) of each first spectrum to the pre-defined spectral lines of the reference spectrum(-a).

S86. The system according to any of the preceding embodiments, wherein the data-processing system (800), particularly the first spectral analysis component (840), is configured for matching each first spectrum to one of the known mineral grains based on a result of the first line assignment component.

S87. The system according to any of the preceding embodiments and with features of S1, wherein the data-processing system (800), particularly the first spectral analysis component (840) is configured for calculating the confidence score for every first spectrum, wherein the confidence score corresponds to the level of agreement between the first spectrum and the corresponding matched reference spectrum.

S88. The system according to any of the preceding embodiments, wherein the classification confidence score describes the probability of the respective first spectrum belonging to one of the known mineral grains.

S89. The system according to any of the preceding embodiments, wherein the confidence score corresponds to a numeric value, wherein the numeric value ranges from 0 to at most 1 and is assigned to each first spectrum.

S90. The system according to any of the preceding embodiments and with the featured of S1, wherein the system is configured for pre-setting the threshold value for the confidence score.

S91. The system according to any of the preceding embodiments and with the features of S90, wherein a high confidence score (above or equal to the threshold value) corresponds to a reliable identification of the chemical composition of the respective mineral grain based on the corresponding first spectrum.

S92. The system according to any of the preceding embodiments and with the features of S90, wherein a low confidence score (below the threshold value) corresponds to a partial identification of the chemical composition of the respective mineral grain based on the corresponding first spectrum.

S93. The system according to any of the preceding embodiments, wherein a mineral grain of low confidence score comprises a similar chemical composition with at least another mineral grain.

S94. The system according to the preceding embodiment, wherein the mineral grains of a similar chemical composition comprise at least one or a plurality of common chemical elements.

S95. The system according to any of the preceding embodiments, wherein the mineral grains of a similar chemical composition comprise the same chemical elements with a different elemental ratio (e.g. $Fe_2O_3$ and $Fe_3O_4$).

S96. The system according to any of the preceding embodiments and with the features of S94, wherein the mineral grains of a similar chemical composition correspond to similar first spectra, wherein the similar first spectra comprise at least one or a plurality of common spectral lines.

S97. The system according to any of the preceding embodiments and with the features of S95, wherein the similar first spectra comprise the same spectral lines (at the same energies) with different intensity ratios.

S98. The system according to any of the preceding embodiments and with the features of S92, wherein the low confidence score results from a low spectral quality of the respective first spectrum.

S99. The system according to the preceding embodiment, wherein the low spectral quality results from spectral lines of the respective first spectrum comprising an insufficient spectral line intensity, wherein the insufficient line intensity results from an insufficient number of photons detected during the second dwell period (i.e. number of detected photons per time).

S100. The system according to any of the preceding embodiments, wherein the system, particularly the data-processing system (800), is configured for estimating an intrinsic photon count rate based on the number of photons detected during the second dwell period (i.e. number of detected photons per time).

S101. The system according to any of the preceding embodiments and with the features of S100, wherein the intrinsic photon count rate depends on the chemical composition of the corresponding part (i.e. mineral grain).

S102. The system according to any of the preceding embodiments and with the features of S100, wherein the intrinsic photon count rate depends on the sample properties, such as crystal properties (e.g. orientation, size, depth), of the corresponding part (i.e. mineral grain).

S103. The system according to any of the preceding embodiments, wherein the system, particularly the data-processing system (800), is further configured for generating at least one or a plurality of second data set(s), wherein each second data set comprises a list of the coordinates of the second scan location(s) relating to the mineral grain(s) of low confidence score of at least one or more regions (i.e. sub-images) of the at least one image.

S104. The system according to any of the preceding embodiments, wherein the data-processing system (800), particularly the data-storage component (810), is configured for providing the second data set(s).

S105. The system according to any of the preceding embodiments, wherein the system is further configured for detecting the second emissions from the second scan locations of the first data set(s) and providing the first spectra in parallel.

S106. The system according to any of the preceding embodiments, wherein the system is further configured for detecting the second emissions from the second scan locations of the first data set(s) and analyzing the first spectra in parallel.

S107. The system according to any of the preceding embodiments, wherein the data-processing system (800) comprises a one-pass classification component (850*a*).

S108. The system according to any of the preceding embodiments, wherein the data-processing system (800) comprises a two-pass classification component (850*b*).

S109. The system according to any of the preceding embodiments, wherein the system, particularly the data-processing system (800), is configured for executing the one-pass and/or the two-pass classification component based on a result of the first spectral analysis component (840).

S110. The system according to any of the preceding embodiments, wherein the system, particularly the data-processing system (800), is configured for executing the one-pass and/or the two-pass classification component after the second detector (112) has completed detecting the second emissions from the second scan location(s) of at least some or all of the first data set(s) of the at least one image.

S111. The system according to any of the preceding embodiments, wherein the system, particularly the scanning microscope system (100), is configured for focusing the beam on at least one of the second scan location(s) of the second data set(s).

S112. The system according to the preceding embodiment, wherein the scanning microscope system (100), particularly the second detector (112), is configured for detecting the second emissions from each second scan location of the second data set(s) upon irradiation of the sample with the beam.

S113. The system according to any of the preceding embodiments and with features of S1, wherein the scanning microscope system (100), particularly the second detector (112), is configured for detecting the second emissions for the duration time of the third dwell period from the at least one second scan location of the second data set(s).

S114. The system according to any of the preceding embodiments, wherein the third dwell period is higher than the second dwell period for the at least one second scan location.

S115. The system according to any of the preceding embodiments, wherein the third dwell period is lower than or equal to the second dwell period for the at least one second scan location.

S116. The system according to any of the preceding embodiments and with the features of S100, wherein the data-processing system (800), particularly the one-pass classification component (850*a*), is configured for determining the third dwell period for the at least one second scan location of the second data set(s) based on the calculated confidence score of the respective first spectrum and the intrinsic photon count rate of the corresponding mineral grain.

S117. The system according to any of the preceding embodiments, wherein the data-processing system (800), particularly the one-pass classification component (850*a*), is configured for adding the number of photons (e.g. X-ray photons) detected within the second dwell period to the number of photons (e.g. X-ray photons) detected within the third dwell period at the respective second scan location of the second data set.

S118. The system according to any of the preceding embodiments and with the features of S117, wherein the data-processing system (800), particularly the one-pass classification component (850*a*), is further configured for generating at least one or a plurality of second spectra, wherein each second spectrum comprises the total number of detected photons (e.g. X-ray photons) at the corresponding second scan location of the second data set(s).

S119. The system according to any of the preceding embodiments, wherein the data-processing system (800), particularly the data-storage component (810), is configured for providing the second spectra in groups, wherein each group comprises the second spectra obtained from the at least one or more images.

S120. The system according to any of the preceding embodiments, wherein each second spectrum corresponds to an X-ray spectrum.

S121. The system according to any of the preceding embodiments and with the features of S119, wherein the data-processing system (800), particularly the one-pass classification component (850*a*), is configured for correcting an image generation error for the case that a group comprises the second spectra obtained from at least two images, wherein the at least two images show neighboring sections of the sample.

S122. The system according to the preceding embodiment, wherein the at least two images contain at least two parts belonging to one of the mineral grains of low confidence score.

S123. The system according to any of the preceding embodiments and with the features of S121, wherein correcting the image generation error comprises stitching the at least two parts of the at least two images.

S124. The system according to any of the preceding embodiments and with the features of S123, wherein data-processing system (800), particularly the one-pass classification component (850*a*), is configured for summing the second spectra of the parts belonging to the same mineral grain of low confidence score by means of another merging operator.

S125. The system according to any of the preceding embodiments, wherein the data-processing system (800), particularly the one-pass classification component (850*a*) comprises a second spectral analysis component.

S126. The system according to any of the preceding embodiments, wherein the one-pass classification component (850*a*), particularly the second spectral analysis component, is configured for analyzing the second spectra of each group individually.

S127. The system according to any of the preceding embodiments, wherein the data-processing system (800), particularly the second spectral analysis component, is configured for matching each second spectrum to at least two known mineral grains based on a result of a second line assignment component.

S128. The system according to any of the preceding embodiments, wherein the data-processing system (800), particularly the second spectral analysis component, is configured for calculating at least two or a plurality of new confidence scores for every second spectrum, wherein each new confidence score corresponds to the level agreement between the second spectrum and the corresponding matched reference spectrum.

S129. The system according to any of the preceding embodiments and with the features of S128, wherein the one-pass classification component is configured for selecting the highest new confidence score out of the at least two new confidence scores for every second spectrum.

S130. The system according to any of the preceding embodiments and with the features of S129, wherein the highest new confidence scores of at least some of the second spectra correspond to a high confidence score (above or equal to the threshold value).

S131. The system according to any of the preceding embodiments and with the features of S130, wherein the data-processing system (800), particularly the one-pass classification component (850*a*), is configured for normalizing the data quality of at least some of the mineral grains of (initial) low confidence score.

S132. The system according to any of the preceding embodiments, wherein the system is configured for detecting the second emissions from the second scan location(s) of the second data sets and analyzing the first spectra in parallel.

S133. The system according to any of the preceding embodiments, wherein the system, particularly the data-processing system (800), is configured for executing the second spectral analysis component after the first spectral analysis component has completed analyzing at least some or all of the first spectra relating to the at least one or more images.

S134. The system according to any of the preceding embodiments and with the features of S132 and S133, wherein the system is configured for detecting the second emissions from the second scan location(s) of the second data sets and analyzing the second spectra in parallel.

S135. The system according to the preceding embodiment, wherein the system is configured for analyzing a first group of second spectra relating to first image(s) while in parallel detecting the second emissions from second scan locations relating to second image(s).

S136. The system according to any of the preceding embodiments, wherein at least one or more of the mineral grain(s) of low confidence score relating to the second data set(s) correspond to specific mineral grains.

S137. The system according to any of the preceding embodiments, wherein at least one of the specific mineral grains is depicted with the same intensity (i.e. gray level intensity) on the at least one image of as at least one other specific mineral grain (e.g. $Fe_2O_3$ and $Fe_3O_4$).

S138. The system according to any of the preceding embodiments, wherein the at least one specific mineral grain is indistinguishable from the at least one other specific mineral grain on the at least one image.

S139. The system according to any of the preceding embodiments, wherein the part(s) of the selected second scan locations relating to the specific mineral grain(s) correspond to specific part(s) of the respective sub-image.

S140. The system according to any of the preceding embodiments, wherein the system, particularly the data-processing system (800), is configured for executing the two-pass classification component (850*b*) on the selected second scan locations of the second data set(s) relating to the specific part(s) of the corresponding sub-images.

S141. The system according to any of the preceding embodiments, wherein the system is configured for pre-setting and/or controlling the contrast and brightness values of a corresponding image (e.g. the at least one image or sections thereof) by adjusting operational settings of the first detector (111) prior to the detection of the corresponding first emissions.

S142. The system according to any of the preceding embodiments, wherein adjusting the operational settings of the first detector (111) comprises adjusting the gain factor of at least one or more amplifier(s) integrated within the first detector (111).

S143. The system according to any of the preceding embodiments, wherein adjusting the operational settings of the first detector (111) comprises adjusting the code width of an analog to digital converter (AD converter) integrated within the first detector (111).

S144. The system according to any of the preceding embodiments, wherein the system, particularly the scanning microscope system (100), is configured for focusing the beam on the first scan locations within the specific part(s).

S145. The system according to any of the preceding embodiments, wherein the scanning microscope system (100), particularly the first detector (111), is configured for re-detecting the first emissions from the first scan locations of the corresponding specific part(s).

S146. The system according to any of the preceding embodiments and with the features of S145, wherein the data-processing system (800), particularly the two-pass classification component (850*b*), is configured for generating at least one or a plurality of new sub-image(s), wherein each new sub-image is based on the first emissions re-detected at each specific part.

S147. The system according to any of the preceding embodiments and with the features of S1 and S141-S143, wherein the system is further configured for acquiring the new sub-image(s) with the adjusted contrast and brightness values by pre-adjusting accordingly the operational settings of the first detector (111).

S148. The system according to any of the preceding embodiments, wherein the data-processing system (800), particularly the data-storage component (810), is configured for providing the new sub-image(s).

S149. The system according to any of the preceding embodiments and with the features of S1, wherein the new image(s) correspond(s) to the new sub-image(s).

S150. The system according to any of the preceding embodiments and with the features of S1, wherein the part(s) delimited by the new image(s) correspond to the specific part(s) delimited by the new sub-image(s).
S151. The system according to any of the preceding embodiments, wherein the data-processing system (800), particularly the two-pass classification component (850b), is further configured for revealing and/or detecting at least two or a plurality of new parts within at least one of the new sub-images by means of the adjusted contrast and brightness values of the respective new sub-image.
S152. The method according to any of the preceding embodiments and with the features of S151, wherein each new part corresponds to a section of the specific part within the respective new sub-image.
S153. The system according to any of the preceding embodiments, wherein the data-processing system (800), particularly the two-pass classification component (850b) is configured for identifying at least two mineral grains within the at least one new sub-image based on the different intensity (e.g. gray level intensity) between the respective new parts, wherein the at least two mineral grains are indistinguishable on the at least one image (and sub-image) and wherein one of the mineral grains corresponds to the specific mineral grain of the specific part.
S154. The system according to any of the preceding embodiments, wherein the two-pass classification component (850b) further comprises a second segmentation component.
S155. The system according to the preceding embodiment, wherein the two-pass classification component (850b), particularly the second segmentation component, is configured for processing the new sub-images individually for the case of more than one new sub-image being provided.
S156. The system according to any of the preceding embodiments, wherein the two-pass classification component (850b), particularly the second segmentation component, is configured for generating a new second scan location for each of the new parts within the at least one new sub-image by means of the k-means clustering algorithm and the flood fill algorithm.
S157. The system according to any of the two preceding embodiments, wherein the two-pass classification component (850b), particularly the second segmentation component, is configured for determining each new second scan location for the duration time of another segmentation period.
S158. The system according to any of the preceding embodiments, wherein the data-processing system (800), particularly the two-pass classification component (850b), is configured for generating third data sets, wherein each of the third data sets comprises a list of the coordinates of the new second scan locations relating to one of the new sub-images.
S159. The system according to any of the preceding embodiments, wherein the data-processing system (800), particularly the data-storage component (810), is configured for providing at least one of the third data sets.
S160. The system according to any of the preceding embodiments, wherein the system, particularly the scanning microscope system (100), is configured for focusing the beam on at least one of the new second scan locations of the at least one third data set.
S161. The system according to the preceding embodiment, wherein the scanning microscope system (100), particularly the second detector (112), is configured for detecting the second emissions from the new second scan locations of the third data set(s) upon irradiation of the sample with the beam.
S162. The system according to any of the preceding embodiments, wherein the scanning microscope system (100), particularly the second detector (112), is configured for detecting the second emissions for the duration time of another third dwell period at every new second scan location of the third data set(s).
S163. The system according to any of the preceding embodiments, wherein the system is configured for determining the new second scan locations for the new sub-images and detecting the second emissions from the new second scan locations of the third data sets in parallel for the case of more than one new sub-image being provided.
S164. The system according to any of the preceding embodiments, wherein the system is configured for determining the new second scan locations of the third data sets and analyzing the first spectra in parallel.
S165. The system according to any of the preceding embodiments, wherein the system is configured for detecting the second emissions from the second scan locations of the third data set(s) and analyzing the first spectra in parallel.
S166. The system according to any of the preceding embodiments, wherein the data-processing system (800), particularly the two-pass classification component (850b) is further configured for generating at least one or a plurality of new spectra, wherein each new spectrum is based on the second emissions detected at the respective new second scan location of the at least one third data set.
S167. The system according to the preceding embodiment, wherein the data-processing system (800), particularly the data-storage component (810), is configured for providing the new spectra in other groups, wherein each other group comprises the new spectra obtained from the at least one or more images.
S168. The system according to any of the preceding embodiments and with the features of S121-S124, wherein the data-processing system (800), particularly the two-pass classification component (850b) is configured for correcting the image generation error as done by the one-pass classification component (850a).
S169. The system according to any of the preceding embodiments, wherein the two-pass classification component (850b) comprises another second spectral analysis component, wherein the other second spectral analysis component comprises analyzing the new spectra of each other group individually.
S170. The system according to any of the preceding embodiments, wherein the data-processing system (800), particularly the other second spectral analysis component, is configured for comparing each new spectrum to the reference spectra and calculating at least two or more other new confidence scores as done by the second spectral analysis component.
S171. The system according to any of the preceding embodiments, wherein the data-processing system (800), particularly the two-pass classification component, is configured for executing the other second spectral analysis component after the first spectral analysis component has essentially completed analyzing at least some or all of the first spectra relating to the at least one or more images.
S172. The system according to any of the preceding embodiments, wherein the system is configured for detecting the second emissions from the new second scan locations of the third data sets and analyzing the new spectra relating to the new second scan locations in parallel.
S173. The system according to the preceding embodiment, wherein the system is configured for analyzing a first other group of new spectra relating to first image(s) while in parallel detecting the second emissions from the new second scan locations relating to second image(s).

S174. The system according to any of the preceding embodiments, wherein the system, particularly the two-pass classification component (850b), is configured for identifying and classifying the at least two specific mineral grains within the same new sub-image based on a result of the second segmentation component and the other second spectral analysis component.

S175. The system according to any of the two preceding embodiments, wherein the third dwell period is longer than the first dwell period.

S176. The system according to any of the two preceding embodiments, wherein the other third dwell period is longer than the first dwell period.

S177. The system according to any of the preceding embodiments, wherein the data-processing system (800) further comprises a post-processing component (860).

S178. The system according to the preceding embodiment, wherein the data-processing system (800), particularly the post-processing component (860), is configured for acquiring other images from other sections of the sample and/or replicant samples with the localized contrast and brightness values of the at least one of the new sub-images.

S179. The system according to any of the preceding embodiments, wherein the data-processing system (800), particularly the post-processing component (860), is configured for applying a calibration model, wherein the calibration model is configured for relating the chemical composition of the mineral grain(s) (e.g. average atomic number) of the sample to the gray level intensity(-ies) of the corresponding parts on the respective other image.

S180. The system according to any of the preceding embodiments and with the features of S179, wherein the calibration model corresponds to a linear regression.

S181. The system according to any of the preceding embodiments, wherein the calibration model comprises the contrast and the brightness values as model parameters (i.e. fitting parameters).

S182. The system according to any of the preceding embodiments and with the features of S179, wherein applying the calibration model comprises using mineral grains of a known chemical composition and their corresponding gray level intensities in the respective other images to calibrate and further constrain the localized contrast and brightness values.

S183. The system according to any of the preceding embodiments and with the features of S182, wherein the data-processing system (800), particularly the post-processing component (860), is configured for determining the chemical composition of unknown mineral grain(s) relating to the other sections of the sample and/or the replicant samples by means of their detected gray level intensity(-ies) and the calibrated contrast and brightness values.

S184. The system according to any of the preceding embodiments, wherein the system is a system configured for material analysis and mineralogy.

S185. The system according to any of the preceding embodiments, wherein the sample comprises a plurality of particles embedded in an epoxy matrix.

S186. The system according to the preceding embodiment, wherein the size of each mineral grain comprises dimensions ranging from at least 1 µm to at most 500 µm.

S187. The system according to any of the preceding embodiments, wherein the scan point comprises dimensions of at most a micron.

S188. The system according to the preceding embodiment, wherein a portion (such as a pixel) of the at least one image comprises dimensions ranging from at least 10 nm to at most 1000 nm.

S189. The system according to any of the preceding embodiments, wherein the second dwell period ranges from at least 1 ms to at most 10 ms.

S190. The system according to any of the preceding embodiments, wherein the data-processing system (800), particularly the one-pass classification component (850a), is configured for calculating a high confidence score for at least some or all mineral grains within the sample by detecting on average at least $2 \times 10^3$ photons and at most $3 \times 10^3$ photons per second scan location.

S191. The system according to any of the preceding embodiments, wherein the system further comprises a control unit (115), wherein the control unit (115) is configured for controlling the power supply and the operation of some of the components of the scanning microscope system (100), such as a condensing lens (104), an objective lens (106), a scanning coil (105) and the movable stage (113).

S192. The system according to any of the preceding embodiments, wherein the system further comprises a vacuum system, wherein the vacuum system comprises a vacuum controller (116), a mechanical pumping system (117), an ultra-high vacuum pump (118) and a vacuum chamber (119).

S193. The system according to the preceding embodiment, wherein the mechanical pumping system (117) and the ultra-high vacuum pump (118) are configured for providing an ultra-high vacuum within the vacuum chamber (119).

S194. The system according to the preceding embodiment, wherein the vacuum chamber (119) is configured for containing a sample (108), the movable stage (113), the first detector (111), the second detector (112) or parts thereof, and a scanning electron microscope (101) or parts thereof.

Method Embodiments

Below, embodiments of a method will be discussed. The method embodiments are abbreviated by the letter "M" followed by a number. Whenever reference is herein made to the "method embodiments", these embodiments are meant.

M1. A method for determining the properties of a sample or sections thereof, comprising:
  providing at least one or a plurality of images of the sample or sections thereof based on first emissions detected within a first dwell period from a plurality of first scan locations;
  performing a first detection step, comprising detecting second emissions for a second dwell period from at least one or a plurality of second scan locations of at least one region of the at least one image, each second scan location relating to a part of the corresponding region;
  performing a first spectrum providing step, comprising providing at least one or a plurality of first spectra, wherein each first spectrum is based on the second emissions detected at each of the second scan location(s) of the at least one region;
  performing a first spectral analysis step, comprising calculating a confidence score for every first spectrum and selecting the second scan location(s) relating to the first spectrum(-a) with confidence score(s) below a threshold value;
  performing a classification step, comprising detecting the second emissions for a third dwell period from at least one of the selected second scan location(s) and/or providing at least one or a plurality of new image(s) delimiting part(s) relating to the selected second scan location(s) and determining new second scan locations within the corresponding new image(s) through modified contrast and brightness values thereof with respect to the at least one image.

M2. The method according to the preceding embodiment, wherein the method further comprises a first segmentation step, wherein the first segmentation step comprises determining the second scan location(s) of the region(s) of the at least one image.

M3. The method according to any of the preceding embodiments further comprising the step of focusing a beam of charged particles (such as electrons) to a scan point on the sample.

M4. The method according to any the preceding embodiments, wherein the method further comprises scanning the beam of charged particles over a plurality of scan locations in one or two dimensions.

M5. The method according to any of the preceding embodiments, wherein the scan locations correspond to the first scan locations.

M6. The method according to any of the preceding embodiments, wherein the scan locations correspond to the second scan locations.

M7. The method according to any of the preceding embodiments, wherein the method further comprises assigning a two-dimensional coordinate system to the sample.

M8. The method according to any of the preceding embodiments and with the features of M7, wherein the method further comprises assigning the two-dimensional coordinate system of the sample to the at least one image.

M9. The method according to any of the preceding embodiments and with the features of M4, wherein a result of scanning the beam of charged particles over the scan locations of the sample comprises an interaction of the beam with the sample.

M10. The method according to the preceding embodiment and with the features of M1, wherein a result of the interaction comprises the first and/or the second emissions.

M11. The method according to the preceding embodiment and with the features of M1 and M10, wherein the first emissions comprise emissions of particles (such as backscattered electrons).

M12. The method according to any of the preceding embodiments and with the features of M1 and M10, wherein the second emissions comprise emissions of photons (such as X-ray photons).

M13. The method according to any of the preceding embodiments, wherein the method further comprises detecting the first emissions from each first scan location.

M14. The method according to the preceding embodiment, wherein the method further comprises generating the at least one image based on the first emissions detected at each first scan location.

M15. The method according to any of the preceding embodiments, wherein the at least one image corresponds to a backscattered electron image.

M16. The method according to any of the preceding embodiments, wherein the at least one image shows intensity variations between the regions (and/or parts thereof) with different properties (such as chemical composition).

M17. The method according to the preceding embodiment, wherein the intensity variations comprise gray level variations.

M18. The method according to any of the preceding embodiments, wherein the at least one image comprises a contrast and a brightness value.

M19. The method according to any of the preceding embodiments, wherein each region of the at least one image corresponds to a particle in the sample.

M20. The method according to the preceding embodiment, wherein each particle in the sample comprises at least one or a plurality of mineral grain(s).

M21. The method according to any of the preceding embodiments, wherein the method further comprises detecting the first emissions for the duration time of the first dwell period at each first scan location.

M22. The method according to any of the preceding embodiments, wherein the first detection step further comprises detecting the second emissions for the duration time of the second dwell period at each second scan location.

M23. The method according to any of the preceding embodiments and with features of M1, wherein the second dwell period is longer than the first dwell period.

M24. The method according to any of the preceding embodiments, wherein the method further comprises detecting the first emissions and detecting the second emissions at different time intervals, wherein the different time intervals correspond to non-overlapping time intervals.

M25. The method according to any of the preceding embodiment and with features of M2, wherein the first segmentation step comprises determining each second scan location for the duration time of a segmentation period.

M26. The method according to any of the preceding embodiments, wherein the segmentation period is longer than the second dwell period.

M27. The method according to any of the preceding embodiments, wherein the segmentation period is shorter than or equal to the second dwell period.

M28. The method according to the preceding embodiment, wherein the segmentation period depends on image properties, such as the resolution and the magnification of the at least one image (or sections thereof).

M29. The method according to any of the preceding embodiments, wherein the segmentation period depends on the size of the mineral grain(s) and/or particle(s).

M30. The method according to any of the preceding method embodiments, wherein the method further comprises a pre-processing step.

M31. The method according to the preceding embodiment, wherein the pre-processing step comprises applying a thresholding algorithm.

M32. The method according to the preceding embodiment, wherein the thresholding algorithm comprises separating the at least one image into a background part and a foreground part based on a threshold intensity.

M33. The method according to any of the preceding embodiments, wherein the background part comprises background portions, wherein the background portions (e.g. pixels) comprise intensities lower than the threshold intensity (e.g. dark gray and/or black portions).

M34. The method according to any of the preceding embodiments, wherein the foreground part comprises foreground portions, wherein the foreground portions (e.g. pixels) comprise intensities higher than or equal to the threshold intensity (e.g. bright gray and/or white portions).

M35. The method according to any of the preceding embodiments, wherein the thresholding algorithm comprises delimiting/removing the background part.

M36. The method according to the preceding embodiment, wherein delimiting/removing the background part comprises assigning to the background portions the same value of color and/or intensity (e.g. black portions).

M37. The method according to any of the preceding embodiments, wherein the foreground part comprises at least some of the regions of the image.

M38. The method according to the preceding embodiment, wherein the pre-processing step comprises determining the boundaries of the corresponding regions of the at least one image by means of a contouring algorithm.

M39. The method according to the preceding embodiment, wherein the contouring algorithm comprises joining adjacent portions along the boundaries of the corresponding regions to curves.

M40. The method according to the preceding embodiment, wherein the adjacent portions along the boundaries of the corresponding regions are surrounded by the background portions (e.g. black portions).

M41. The method according to any of the preceding embodiments, wherein the pre-processing step further comprises applying a bounding box algorithm, wherein the bounding box algorithm comprises dividing the at least one image into at least one or a plurality of sub-images based on a result of the contouring algorithm.

M42. The method according to any of the preceding embodiments and with the features of M41, wherein a sub-image of the at least one image is delimiting one region.

M43. The method according to any of the preceding embodiments and with the features of M41, wherein the method comprises providing the sub-image(s).

M44. The method according to any of the preceding embodiments, wherein the first segmentation step comprises correcting a sub-image generation error.

M45. The method according to the preceding embodiment, wherein the sub-image generation error comprises generating at least one sub-image containing at least two neighboring regions.

M46. The method according to the preceding embodiment, wherein the at least two neighboring regions located within the one sub-image correspond to touching particles in the sample.

M47. The method according to any of the preceding embodiments, wherein at least one or more portions along the boundary of one of the neighboring regions are contiguous with at least one or more portions along the boundary of another of the neighboring regions.

M48. The method according to any of the preceding embodiments and with the features of M44, wherein correcting the sub-image generation error comprises processing each of the neighboring regions within the one sub-image individually.

M49. The method according to any of the preceding embodiments and with the features of M41, wherein the method further comprises performing the first segmentation step on the sub-images individually for the case of more than one sub-image being provided.

M50. The method according to any of the preceding embodiments, wherein the first segmentation step comprises assigning contiguous portions of the parts of the corresponding regions within the respective sub-images to clusters by means of a k-means clustering algorithm.

M51. The method according to any of the two preceding embodiments, wherein each region of the respective sub-image comprises at least one or a plurality of clusters.

M52. The method according to the preceding embodiment and with the features of M50, wherein the first segmentation step further comprises applying a flood fill algorithm, wherein the flood fill algorithm comprises generating a mask for at least one of the clusters.

M53. The method according to the preceding embodiment, wherein generating the mask for the at least one of the clusters comprises assigning to contiguous portions within the corresponding cluster the same value of color and/or intensity.

M54. The method according to any of the preceding embodiments, wherein each mask is delimiting a part of the corresponding region.

M55. The method according to the preceding embodiment, wherein a part within each region of the at least one image corresponds to a mineral grain within the corresponding particle in the sample.

M56. The method according to any of the preceding embodiments, wherein the first segmentation step further comprises determining one second scan location for each mask.

M57. The method according to the preceding embodiment, wherein each second scan location corresponds to a centroid of the respective mask.

M58. The method according to any of the preceding embodiments, wherein the method further comprises correcting an over-segmentation error.

M59. The method according to the preceding embodiment, wherein the over-segmentation error comprises determining more than one second scan location for at least one of the masks.

M60. The method according to any of the two preceding embodiments, wherein the method comprises merging the second scan locations for the at least one of the masks into one second scan location by means of a merging operator.

M61. The method according to any of the preceding embodiments, wherein the method further comprises generating first data set(s) for the region(s) within the respective sub-image(s).

M62. The method according to the preceding embodiment, wherein a first data set comprises a list of the coordinates of the second scan location(s) relating to one of the regions.

M63. The method according to any of the preceding embodiments, wherein the method further comprises providing at least one of the first data sets.

M64. The method according to any of the preceding embodiments, wherein the first detection step comprises focusing the beam on at least one of the second scan locations of the at least one of the first data sets.

M65. The method according to the preceding embodiment, wherein the first detection step further comprises detecting the second emissions from the corresponding second scan location(s) of the first data set(s) upon irradiation of the sample with the beam.

M66. The method according to any of the preceding embodiments, wherein the method further comprises performing the first segmentation step and the first detection step in parallel for the case of more than one sub-image (i.e. first data set) being provided.

M67. The method according to any of the preceding embodiments and with the features of M1, wherein the method comprises generating the first spectrum(-a) based on the second emissions (i.e. number of photons) detected at the corresponding second scan location(s) of the at least one sub-image (i.e. first data set).

M68. The method according to any of the preceding embodiments, wherein each first spectrum corresponds to an X-ray spectrum.

M69. The method according to the preceding embodiment, wherein the X-ray spectrum comprises at least one or a plurality of spectral lines.

M70. The method according to any of the preceding embodiments and with the features of M68 and M69, wherein the X-ray spectrum comprises the number of detected X-ray photons (i.e. spectral line intensity) at the respective energies.

M71. The method according to the preceding embodiment, wherein each spectral line corresponds to an electronic transition of a chemical element.

M72. The method according to any of the preceding embodiments, wherein each mineral grain of the sample comprises at least one or a plurality of chemical elements.

M73. The method according to any of the preceding embodiments, wherein the X-ray spectrum comprises information about the chemical composition (e.g. mineral composition) of the corresponding mineral grain relating to the respective second scan location.

M74. The method according to any of the preceding embodiments, wherein the first spectral analysis step comprises analyzing each first spectrum from the respective second scan location of the at least one of the regions (i.e. first data sets).

M75. The method according to the preceding embodiment, wherein analyzing each first spectrum comprises comparing the respective first spectrum with at least one or a plurality of reference spectra.

M76. The method according to the preceding embodiment, wherein each reference spectrum comprises a plurality of pre-defined spectral lines relating to a known mineral grain.

M77. The method according to any of the preceding embodiments, wherein the first spectral analysis step further comprises a first line assignment step, wherein the first line assignment step comprises assigning the spectral line(s) of each first spectrum to the pre-defined spectral lines of the reference spectrum(-a).

M78. The method according to any of the preceding embodiments, wherein the first spectral analysis step comprises matching each first spectrum to one of the known mineral grains based on a result of the first line assignment step.

M79. The method according to the preceding embodiment and with features of M1, wherein the confidence score corresponds to the level of agreement between the first spectrum and the corresponding matched reference spectrum.

M80. The method according to any of the preceding embodiments, wherein the confidence score corresponds to a numeric value, wherein the numeric value ranges from 0 to at most 1 and is assigned to each first spectrum.

M81. The method according to any of the preceding embodiments, wherein the confidence score describes the probability of the respective first spectrum belonging to one of the known mineral grains.

M82. The method according to any of the preceding embodiments and with the features of M1, wherein the method comprises pre-setting the threshold value for the confidence score.

M83. The method according to any of the preceding embodiments and with the features of M82, wherein a high confidence score (above or equal to the threshold value) corresponds to a reliable identification of the chemical composition of the respective mineral grain based on the corresponding first spectrum.

M84. The method according to any of the preceding embodiments and with the features of M82, wherein a low confidence score (below the threshold value) corresponds to a partial identification of the chemical composition of the respective mineral grain based on the corresponding first spectrum.

M85. The method according to any of the preceding embodiments, wherein a mineral grain of low confidence score comprises a similar chemical composition with at least another mineral grain.

M86. The method according to the preceding embodiment, wherein the mineral grains of a similar chemical composition comprise at least one or a plurality of common chemical elements.

M87. The method according to any of the preceding embodiments, wherein the mineral grains of a similar chemical composition comprise the same chemical elements with a different elemental ratio (e.g. $Fe_2O_3$ and $Fe_3O_4$).

M88. The method according to any of the preceding embodiments and with the features of M86, wherein the mineral grains of a similar chemical composition correspond to similar first spectra, wherein the similar first spectra comprise at least one or a plurality of common spectral lines.

M89. The method according to any of the preceding embodiments and with the features of M87, wherein the similar first spectra comprise the same spectral lines (at the same energies) with different intensity ratios.

M90. The method according to any of the preceding embodiments and with the features of M84, wherein the low confidence score results from a low spectral quality of the respective first spectrum.

M91. The method according to the preceding embodiment, wherein the low spectral quality results from spectral lines of the respective first spectrum comprising an insufficient spectral line intensity, wherein the insufficient line intensity results from an insufficient number of photons detected during the second dwell period.

M92. The method according to any of the preceding embodiments, wherein the method comprises estimating an intrinsic photon count rate based on the number of photons detected during the second dwell period (i.e. number of detected photons per time).

M93. The method according to any of the preceding embodiments and with the features of M92, wherein the intrinsic photon count rate depends on the chemical composition of the corresponding part (i.e. mineral grain).

M94. The method according to any of the preceding embodiments and with the features of M93, wherein the intrinsic photon count rate depends on the sample properties, such as crystal properties (e.g. orientation, size, depth), of the corresponding part (i.e. mineral grain).

M95. The method according to any of the preceding embodiments, wherein the method further comprises generating and providing at least one or a plurality of second data set(s), wherein each second data set comprises a list of the coordinates of the second scan location(s) relating to the mineral grain(s) of low confidence score of at least one or more regions (i.e. sub-images) of the at least one image.

M96. The method according to any of the preceding embodiments, wherein the method comprises performing the first detection step and the first spectrum providing step in parallel.

M97. The method according to any of the preceding embodiments, wherein the method comprises performing the first detection step and the first spectral analysis step in parallel.

M98. The method according to any of the preceding embodiments, wherein the classification step comprises a one-pass classification step and/or a two-pass classification step.

M99. The method according to any of the preceding embodiments, wherein the classification step comprises performing the one-pass and/or the two-pass classification step based on a result of the first spectral analysis step.

M100. The method according to any of the preceding embodiments, wherein the one-pass classification step comprises performing the one-pass and/or the two-pass classification step after the first detection step has been essentially performed on the corresponding image.

M101. The method according to any of the preceding embodiments, wherein the one-pass classification step comprises performing the one-pass and/or the two-pass classification step after the first detection step has been completed.

M102. The method according to any of the preceding embodiments, wherein the one-pass classification step comprises a second detection step, wherein the second detection step comprises focusing the beam on at least one of the second scan locations of the second data set(s).

M103. The method according to the preceding embodiment, wherein the second detection step further comprises detecting the second emissions from each second scan location of the second data set(s) upon irradiation of the sample with the beam.

M104. The method according to any of the preceding embodiments, wherein the second detection step comprises detecting the second emissions for the duration time of the third dwell period from the at least one second scan location (of the second data set(s).

M105. The method according to any of the preceding embodiments, wherein the third dwell period is higher than the second dwell period for the at least one second scan location.

M106. The method according to any of the preceding embodiments, wherein the third dwell period is lower than or equal to the second dwell period for the at least one second scan location.

M107. The method according to any of the preceding embodiments and with the features of M92, wherein the one-pass classification step comprises determining the third dwell period for the at least one second scan location of the second data set(s) based on the calculated confidence score of the respective first spectrum and the intrinsic photon count rate of the corresponding mineral grain.

M108. The method according to any of the preceding embodiments, wherein the one-pass classification step comprises adding the number of photons (e.g. X-ray photons) detected with the first detection step to the number of photons (e.g. X-ray photons) detected with the second detection step at the respective second scan location of the second data set(s).

M109. The method according to any of the preceding embodiments and with the features of M108, wherein the one-pass classification step further comprises generating at least one or a plurality of second spectra, wherein each second spectrum is based on the second emissions detected with the first and the second detection step at the respective second scan location of the second data set(s).

M110. The method according to any of the preceding embodiments and with the features of M109, wherein the method comprises a second spectrum providing step, wherein the second spectrum providing step comprises providing the second spectra in groups, wherein each group comprises the second spectra obtained from the at least one or more images.

M111. The method according to any of the preceding embodiments, wherein each second spectrum corresponds to an X-ray spectrum.

M112. The method according to any of the preceding embodiments and with the features of M110, wherein the one-pass classification step comprises correcting an image generation error for the case that a group comprises the second spectra obtained from at least two images, wherein the at least two images show neighboring sections of the sample.

M113. The method according to the preceding embodiment, wherein the at least two images contain at least two parts belonging to one of the mineral grains of low confidence score.

M114. The method according to any of the preceding embodiments and with the features of M112, wherein correcting the image generation error comprises stitching the at least two parts of the at least two images.

M115. The method according to any of the preceding embodiments and with the features of M114, wherein the one-pass classification step comprises summing the second spectra of the parts belonging to the same mineral grain of low confidence score by means of another merging operator.

M116. The method according to any of the preceding embodiments, wherein the one-pass classification step comprises a second spectral analysis step.

M117. The method according to any of the preceding embodiments, wherein the one-pass classification step comprises performing the second spectral analysis step on the second spectra of each group individually.

M118. The method according to any of the preceding embodiments, wherein the second spectral analysis step comprises matching each second spectrum to at least two known mineral grains based on a result of a second line assignment step.

M119. The method according to any of the preceding embodiments, wherein the second spectral analysis step comprises calculating at least two or a plurality of new confidence scores for every second spectrum, wherein each new confidence score corresponds to the level agreement between the second spectrum and the corresponding matched reference spectrum.

M120. The method according to any of the preceding embodiments and with the features of M119, wherein the one-pass classification step comprises selecting the highest new confidence score out of the at least two new confidence scores for every second spectrum.

M121. The method according to any of the preceding embodiments, wherein the highest new confidence scores of at least some of the second spectra correspond to a high confidence score (above or equal to the threshold value).

M122. The method according to any of the preceding embodiments and with the features of M121, wherein the one-pass classification step comprises normalizing the data quality of the mineral grains of (initial) low confidence score.

M123. The method according to any of the preceding embodiments, wherein the one-pass classification step comprises performing the second detection step and the first spectral analysis step in parallel.

M124. The method according to the preceding embodiment, wherein the one-pass classification step comprises performing the second spectral analysis step after the first spectral analysis step has been essentially performed on the at least one or more images.

M125. The method according to any of the preceding embodiments and with the features of M123 and M124, wherein the one-pass classification step comprises performing the second detection step and the second spectral analysis step in parallel.

M126. The method according to the preceding embodiment, wherein the one-pass classification step comprises performing the second spectral analysis step on a first group of second spectra relating to first image(s) while in parallel performing the second detection step on second scan locations relating to second image(s).

M127. The method according to any of the preceding embodiments, wherein at least one or more of the mineral grain(s) of low confidence score relating to the second data set(s) correspond to specific mineral grain(s).

M128. The method according to any of the preceding embodiments, wherein at least one of the specific mineral grains is depicted with the same or a similar intensity (i.e. gray level intensity) on the at least one image as at least one other specific mineral grain (e.g. $Fe_2O_3$ and $Fe_3O_4$).

M129. The method according to any of the preceding embodiments, wherein the at least one specific mineral grain is indistinguishable from the at least one other specific mineral grain on the at least one image.

M130. The method according to any of the preceding embodiments, wherein the part(s) of the selected second scan location(s) relating to the specific mineral grain(s) correspond to specific part(s) of the respective sub-image.

M131. The method according to any of the preceding embodiments, wherein the classification step further comprises performing the two-pass classification step on the selected second scan location(s) of the second data set(s) relating to the specific part(s) of the corresponding sub-images.

M132. The method according to any of the preceding embodiments, wherein the two-pass classification step comprises pre-setting and/or controlling the contrast and brightness values of a corresponding image (e.g. the at least one image or sections thereof) by means of adjusting operational settings of at least one or more system components prior to detecting the corresponding first emissions.

M133. The method according to any of the preceding embodiments, wherein the two-pass classification step further comprises focusing the beam on the first scan locations within the specific part(s).

M134. The method according to any of the preceding embodiments and with features of M131, wherein the two-pass classification step comprises re-detecting the first emissions from the first scan locations of the corresponding specific part(s) upon irradiation of the beam with the sample.

M135. The method according to any of the preceding embodiments, wherein the method comprises generating and providing at least one or a plurality of new sub-image(s), wherein each new sub-image is based on the first emissions re-detected at each specific part.

M136. The method according to any of the preceding embodiments and with the features of M1 and M132, wherein the two-pass classification step further comprises acquiring the new sub-image(s) with the adjusted contrast and brightness values by pre-adjusting accordingly the operational settings of the at least one system component.

M137. The method according to any of the preceding embodiments and with the features of M1, wherein the new image(s) correspond(s) to the new sub-image(s).

M138. The method according to any of the preceding embodiments and with the features of M1, wherein the part(s) delimited by the new image(s) correspond to the specific part(s) delimited by the new sub-image(s).

M139. The method according to any of the preceding embodiments, wherein the two-pass classification step further comprises revealing and/or detecting at least two or a plurality of new parts within at least one of the new sub-images by means of the adjusted contrast and brightness values of the respective new sub-image.

M140. The method according to any of the preceding embodiments and with the features of M139, wherein each new part corresponds to a section of the specific part within the respective new sub-image.

M141. The method according to any of the preceding embodiments and with the features of M139, wherein the two-pass classification step comprises identifying at least two mineral grains within the at least one new sub-image based on the different intensities (e.g. gray level intensities) between the respective new parts, wherein the at least two mineral grains are indistinguishable on the at least one image (and sub-image) and wherein one of the mineral grains corresponds to the specific mineral grain of the specific part.

M142. The method according to any of the preceding embodiments, wherein the two-pass classification step further comprises performing a second segmentation step on the new sub-images individually for the case of more than one new sub-image being provided.

M143. The method according to any of the preceding embodiments, wherein the second segmentation step comprises generating a new second scan location for each of the new parts within the at least one new sub-image by means of the k-means clustering algorithm and the flood fill algorithm.

M144. The method according to any of the two preceding embodiments, wherein the second segmentation step comprises determining each new second scan location for the duration time of another segmentation period.

M145. The method according to any of the preceding embodiments, wherein the two-pass classification step comprises generating third data sets, wherein each of the third data sets comprises a list of the coordinates of the new second scan locations relating to one of the new sub-images.

M146. The method according to any of the preceding embodiments, wherein the method further comprises providing at least one of the third data sets.

M147. The method according to any of the preceding embodiments, wherein the two-pass classification step comprises performing another second detection step on the new second scan locations of the at least one third data set.

M148. The method according to any of the preceding embodiments, wherein the other second detection step comprises focusing the beam on at least one of the new second scan locations of the at least one of the third data sets.

M149. The method according to the preceding embodiment, wherein the other second detection step further comprises detecting the second emissions from the corresponding new second scan locations upon irradiation of the sample with the beam.

M150. The method according to any of the preceding embodiments, wherein the other second detection step comprises detecting the second emissions for the duration time of another third dwell period at every new second scan location of the respective third data set.

M151. The method according to any of the preceding embodiments, wherein the two-pass classification step comprises performing the second segmentation step and the other second detection step in parallel for the case of more than one new sub-image being provided.

M152. The method according to any of the preceding embodiments, wherein the two-pass classification step comprises performing the second segmentation step and the first spectral analysis in parallel.

M153. The method according to any of the preceding embodiments, wherein the two-pass classification step comprises performing the other second detection step and the first spectral analysis in parallel M154. The method according to any of the preceding embodiments, wherein the two-pass classification step further comprises generating at least one or a plurality of new spectra, wherein each new spectrum is based on the second emissions detected with the other second detection step at the respective new second scan location of the at least one third data set.

M155. The method according to any of the preceding embodiments, wherein the method comprises a new spectrum providing step, wherein the new spectrum providing step comprises providing the new spectra in other groups, wherein each other group comprises the new spectra obtained from the at least one or more images.

M156. The method according to any of the preceding embodiments and with the features of M112-M115, wherein the two-pass classification step comprises correcting the image generation error as done in the one-pass classification step.

M157. The method according to any of the preceding embodiments, wherein the two-pass classification step comprises performing another second spectral analysis step on the new spectra of each other group individually.

M158. The method according to any of the preceding embodiments and with the features of M119-M121, wherein the other second spectral analysis step comprises comparing each new spectrum to the reference spectra and calculating at least two or more other new confidence scores as done in the second spectral analysis step of the one-pass classification step.

M159. The method according to any of the preceding embodiments, wherein the two-pass classification step comprises performing the other second spectral analysis step after the first spectral analysis has been essentially performed on the at least one or more images.

M160. The method according to any of the preceding embodiments, wherein the two-pass classification step comprises performing the other second detection step and the other second spectral analysis step in parallel.

M161. The method according to the preceding embodiment, wherein the two-pass classification step comprises performing the other second spectral analysis on a first other group of new spectra relating to first image(s) while in parallel performing the second detection step on new second scan locations relating to second image(s).

M162. The method according to any of the preceding embodiments, wherein the two-pass classification step comprises identifying and classifying the at least two specific mineral grains within the same new sub-image based on a result of the second segmentation step and the other second spectral analysis step.

M163. The method according to any of the two preceding embodiments, wherein the third dwell period is longer than the first dwell period.

M164. The method according to any of the two preceding embodiments, wherein the other third dwell period is longer than the first dwell period.

M165. The method according to any of the preceding embodiments, wherein the method further comprises a post-processing step.

M166. The method according to the preceding embodiment, wherein the post-processing step comprises acquiring other images from other sections of the sample and/or replicant samples with the localized contrast and brightness values of the at least one of the new sub-images.

M167. The method according to any of the preceding embodiments, wherein the post-processing step comprises applying a calibration model, wherein the calibration model comprises relating the chemical composition of the mineral grain(s) (e.g. average atomic number) of the sample to the gray level intensity(-ies) of the corresponding parts on the respective other image.

M168. The method according to any of the preceding embodiments and with the features of M167, wherein the calibration model corresponds to a linear regression.

M169. The method according to any of the preceding embodiments, wherein the calibration model comprises the contrast and the brightness values as model parameters (i.e. fitting parameters).

M170. The method according to any of the preceding embodiments and with the features of M167, wherein applying the calibration model comprises using mineral grains of a known chemical composition and their corresponding gray level intensities in the respective other images to calibrate and further constrain the localized contrast and brightness values.

M171. The method according to any of the preceding embodiments and with the features of M170, wherein the post-processing step comprises determining the chemical composition of mineral grain(s) relating to the other sections of the sample and/or the replicant samples by means of their detected gray level intensity(-ies) and the calibrated contrast and brightness values.

M172. The method according to any of the preceding method embodiments, wherein at least a part of the one-pass classification step and at least a part of the two-pass classification step are computer implemented.

M173. The method according to any of the preceding embodiments, wherein the pre-processing step, the first segmentation step, the first spectral analysis step and the post-processing step are computer implemented.

M174. The method according to any of the preceding embodiments, wherein the method is a method for material analysis and mineralogy.

M175. The method according to any of the preceding embodiments, wherein the sample comprises a plurality of particles embedded in an epoxy matrix.

M176. The method according to the preceding embodiment, wherein the size of each mineral grain comprises dimensions ranging from at least 1 μm to at most 500 μm.

M177. The method according to any of the preceding embodiments, wherein the scan point comprises dimensions of at most a micron.

M178. The method according to the preceding embodiment, wherein a portion (such as a pixel) of the at least one image comprises dimensions ranging from at least 10 nm to at most 1000 nm.

M179. The method according to any of the preceding embodiments, wherein the second dwell period ranges from at least 1 ms to at most 10 ms.

M180. The method according to any of the preceding embodiments, wherein the one-pass classification step comprises calculating a high confidence score for at least some or all mineral grains within the sample by detecting on average at least $2\times10^3$ photons and at most $3\times10^3$ photons per second scan location.

M181. The method according to any of the preceding method embodiments, wherein the method comprises using the system according to any of the system embodiments.

S195. The system according to any of the preceding system embodiments, wherein the system is configured for performing the method according to any of the preceding method embodiments.

Below, embodiments of a computer program product will be discussed. These embodiments are abbreviated by the letter "C" followed by a number. Whenever reference is herein made to the "computer program product embodiments", these embodiments are meant.

C1. A computer program product comprising instructions which, when the program is executed by a computer, cause the scanning microscope system to carry out the steps of the method according to any of the method embodiments.

C2. A computer program product comprising instructions which, when the program is executed by a data-processing system (800), cause the data-processing system (800) to perform the steps for which the data-processing system (800) of the system according to any of the system embodiments is configured.

REFERENCE SIGNS

100 scanning microscope system
101 scanning electron microscope
102 electron source
103 anode
104 condensing lens
105 scanning coil
106 objective lens
107 electron beam
108 sample
109 first emissions
110 second emissions
111 first detector
112 second detector
113 movable stage
114 center line of the second detector
115 control unit
116 vacuum controller
117 mechanical pumping system
118 ultra-high vacuum pump
119 vacuum chamber
200 particle
201 epoxy matrix
202 first scan location
203 dashed line
300 image
301 region
302 sub-image
303 (specific) part of the sub-image
304 second scan location
305 spectrum
306 spectral line
400 new sub-image
401 new part of the new sub-image
402 new second scan location
S1 image providing step
S2 first detection step
S3 first spectrum providing step
S4 first spectral analysis step
S5 classification step
500 first data set
501 second data set
600-625 steps of a method embodiment illustrated in a flowchart of FIG. 6
700a-710a steps of a one-pass classification process (step 621a in FIG. 6) illustrated in a flowchart of FIG. 7a
700b-719b steps of a two-pass classification process (step 621b in FIG. 6) illustrated in a flowchart of FIG. 7b
800 data-processing system
810 data-storage component
820 first segmentation component
830 pre-processing component
840 first spectral analysis component
850a one-pass classification component
850b two-pass classification component
860 post-processing component

The invention claimed is:

1. A system configured for material analysis and mineralogy, comprising a scanning microscope system, the scanning microscope system comprising a first detector and a second detector, and further comprising a data-processing system, the data-processing system comprising a data-storage component, and a first spectral analysis component;
   wherein the data-storage component is configured for providing at least one or a plurality of images of a sample or sections thereof based on first emissions detected by the first detector within a first dwell period from a plurality of first scan locations;
   wherein the second detector is configured for detecting second emissions for a second dwell period from at least one or a plurality of second scan locations of at least one region of the at least one image, each second scan location relating to a part of the corresponding region;
   wherein the data-storage component is configured for providing at least one or a plurality of first spectra, wherein each first spectrum is based on the second emissions detected at each of the second scan location(s) of the at least one region;
   wherein the first spectral analysis component is configured for calculating a confidence score for every first spectrum and selecting the second scan location(s) relating to the first spectrum (-a) with confidence score(s) below a threshold value;
   wherein the second detector is configured for detecting second emissions for a third dwell period from at least one of the selected second scan location(s); and
   wherein the data-processing system is configured for determining the third dwell period for the at least one of the selected second scan location(s) based on the calculated confidence score of the respective first spectrum.

2. The system according to claim 1, wherein the data-processing system comprises a first segmentation component, wherein the first segmentation component is configured for determining the second scan location(s) of the region(s) of the at least one image, wherein a region corresponds to a particle in the sample, wherein a part in a region corresponds to a mineral grain in the respective particle.

3. The system according claim 1, wherein the scanning microscope system is configured for generating the first emissions and the second emissions, wherein the first emissions comprise emissions of particles (e.g. backscattered electrons), wherein the second emissions comprise emissions of photons (e.g. X-ray photons).

4. The system according to claim 1, wherein the data-storage component is configured for providing at least one or a plurality of new image(s) delimiting part(s) relating to the selected second scan location(s) and determining new second scan locations within the respective new image(s) through modified contrast and brightness values thereof with respect to the at least one image.

5. The system according to claim 4, wherein the data-processing system is configured for generating the at least one image and the new image(s) based on the first emissions detected at each first scan location, and/or the at least one image corresponds to a backscattered electron image and/or the new image(s) correspond to backscattered electron image(s).

6. The system according to claim 4, wherein the data-processing system is configured for revealing and/or detecting at least two or a plurality of new parts within at least one of the new images by means of the adjusted contrast and brightness values of the respective new image, wherein the new parts correspond to mineral grains comprising the same or a similar intensity on the at least one image, (i.e. indistinguishable mineral grains).

7. The system according to claim 6, wherein the second detector, is configured for detecting the second emissions from the new second scan locations of the new parts for the duration time of another third dwell period.

8. The system according to claim 1, wherein the data-processing system, is configured for generating the first spectrum (-a) based on the second emissions detected at each of the second scan location(s) of the region(s), wherein each first spectrum corresponds to an X-ray spectrum.

9. The system according to claim 1, wherein the data-processing system, is configured for generating at least one or a plurality of second spectra, wherein each second spectrum comprises the total number of photons (e.g. X-ray photons) detected during the second and the third dwell period at the corresponding selected second scan location.

10. The system according to claim 9, wherein the data-processing system is configured for calculating at least two or a plurality of new confidence scores for every second spectrum, wherein the highest new confidence scores of at least some of the second spectra correspond to a high confidence score (above or equal to the threshold value).

11. A method for determining the properties of a sample or sections thereof, comprising:
   providing at least one or a plurality of images of the sample or sections thereof based on first emissions detected within a first dwell period from a plurality of first scan locations;
   performing a first detection step, comprising detecting second emissions for a second dwell period from at least one or a plurality of second scan locations of at least one region of the at least one image, each second scan location relating to a part of the corresponding region;
   performing a first spectrum providing step, comprising providing at least one or a plurality of first spectra, wherein each first spectrum is based on the second emissions detected at each of the second scan location(s) of the at least one region;
   performing a first spectral analysis step, comprising calculating a confidence score for every first spectrum and selecting the second scan location(s) relating to the first spectrum (-a) with confidence score(s) below a threshold value;
   determining a third dwell period for at least one of the selected second scan location(s) based on the calculated confidence score of the respective first spectrum,
   performing a classification step, comprising detecting the second emissions for the third dwell period from the at least one of the selected second scan location(s).

12. The method according to claim 11, wherein the method further comprises a first segmentation step, wherein the first segmentation step comprises determining the second scan location(s) of the region(s) of the at least one image, wherein a region corresponds to a particle in the sample (108), wherein a part in a region corresponds to a mineral grain in the respective particle.

13. The method according to claim 11, further comprising providing at least one or a plurality of new image(s) delimiting part(s) relating to the selected second scan location(s) and determining new second scan locations within the corresponding new image(s) through modified contrast and brightness values thereof with respect to the at least one image.

14. The method according to claim 13, wherein the method comprises generating the at least one image and the new image(s) based on the first emissions detected at each first scan location, and/or the at least one image corresponds to a backscattered electron image and/or the new image(s) correspond to backscattered electron image(s).

15. The method according to claim 13, wherein the classification step comprises a two-pass classification step, wherein the two-pass classification step comprises revealing and/or detecting at least two or a plurality of new parts within at least one of the new images by means of the adjusted contrast and brightness values of the respective new image, wherein the new parts correspond to mineral grains comprising the same or a similar intensity on the at least one image, (i.e. indistinguishable mineral grains).

16. The method according to claim 15, wherein the two-pass classification step comprises detecting the second emissions from the new second scan locations of the new parts for the duration time of another third dwell period.

17. The method according to claim 11, wherein the method comprises generating the first spectrum (-a) based on the second emissions detected at each of the second scan location(s) of the region(s), wherein each first spectrum corresponds to an X-ray spectrum.

18. The method according to claim 11, wherein the confidence score(s) below the threshold value correspond to low confidence score(s), wherein a low confidence score corresponds to a partial identification of the chemical composition of the respective mineral grain based on the corresponding first spectrum, wherein a mineral grain of low confidence score comprises a similar chemical composition with at least another mineral grain.

19. The method according to claim 11, wherein the classification step comprises a one-pass classification step, wherein the one-pass classification step comprises generating at least one or a plurality of second spectra, wherein each second spectrum comprises the total number of photons (e.g. X-ray photons) detected during the second and the third dwell period at the corresponding selected second scan location.

20. The method according to claim 19, wherein the one-pass classification step comprises calculating at least two or a plurality of new confidence scores for every second spectrum, wherein the highest new confidence scores of at least some of the second spectra correspond to a high confidence score (above or equal to the threshold value).

* * * * *